(12) United States Patent
Ikuma et al.

(10) Patent No.: US 8,023,712 B2
(45) Date of Patent: Sep. 20, 2011

(54) MEDICAL SYSTEM AND METHOD FOR GENERATING MEDICAL GUIDE IMAGE

(75) Inventors: Soichi Ikuma, Hachioji (JP); Tomonao Kawashima, Hachioji (JP); Masahiko Komuro, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 504 days.

(21) Appl. No.: 12/342,872

(22) Filed: Dec. 23, 2008

(65) Prior Publication Data

US 2009/0175518 A1 Jul. 9, 2009

(30) Foreign Application Priority Data

Dec. 27, 2007 (JP) ................. 2007-337659

(51) Int. Cl.
*A61B 1/00* (2006.01)
*A61B 8/00* (2006.01)
*A61B 8/13* (2006.01)
*G06K 9/00* (2006.01)

(52) U.S. Cl. ........ 382/131; 382/128; 600/103; 600/424; 600/440; 600/443

(58) Field of Classification Search .......... 382/128–134; 128/922; 600/101, 103, 118, 407, 424, 437, 600/440, 443, 447, 459, 462, 463

See application file for complete search history.

(56) References Cited

U.S. PATENT DOCUMENTS

| 6,661,571 | B1 * | 12/2003 | Shioda et al. ................. 359/372 |
| 7,837,616 | B2 * | 11/2010 | Tsuji et al. ..................... 600/117 |
| 2007/0239009 | A1 * | 10/2007 | Kawashima et al. ......... 600/437 |
| 2008/0300453 | A1 * | 12/2008 | Aoki et al. .................... 600/103 |
| 2009/0299142 | A1 * | 12/2009 | Uchiyama et al. ............ 600/118 |

FOREIGN PATENT DOCUMENTS

JP 2006-149481 6/2006

* cited by examiner

*Primary Examiner* — David Mis

(74) *Attorney, Agent, or Firm* — Scully, Scott, Murphy & Presser, P.C.

(57) ABSTRACT

A medical system includes: an image signal acquiring portion for acquiring a signal to generate an image corresponding to a picture of a subject; an image generating portion for generating a real-time image of an inside of the test subject based on the acquired signal; a detecting portion for outputting a position and an orientation of an image position and orientation detecting element as a detection value; a reference image data storage portion for storing reference image data made up of anatomical images of the test subject; a guide image generating portion for generating a guide image to provide guide information about at least one of an anatomical position and orientation within the test subject of the real-time image, based on the detection value and the reference image data; and a detection state notification information generating portion for generating information to notify a detection state of the detection value.

14 Claims, 32 Drawing Sheets

FIG.10A
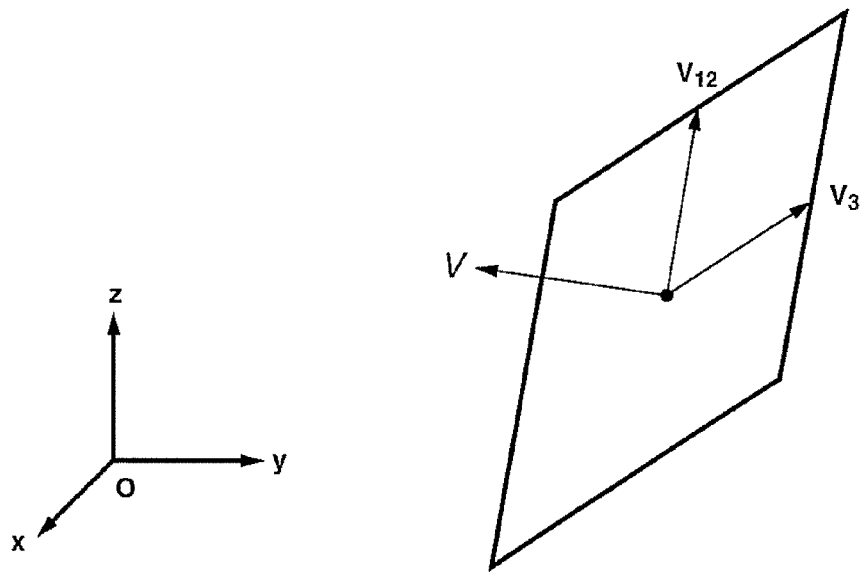
MAPPING AND MARKER GENERATION
IMAGE INDICATOR DATA
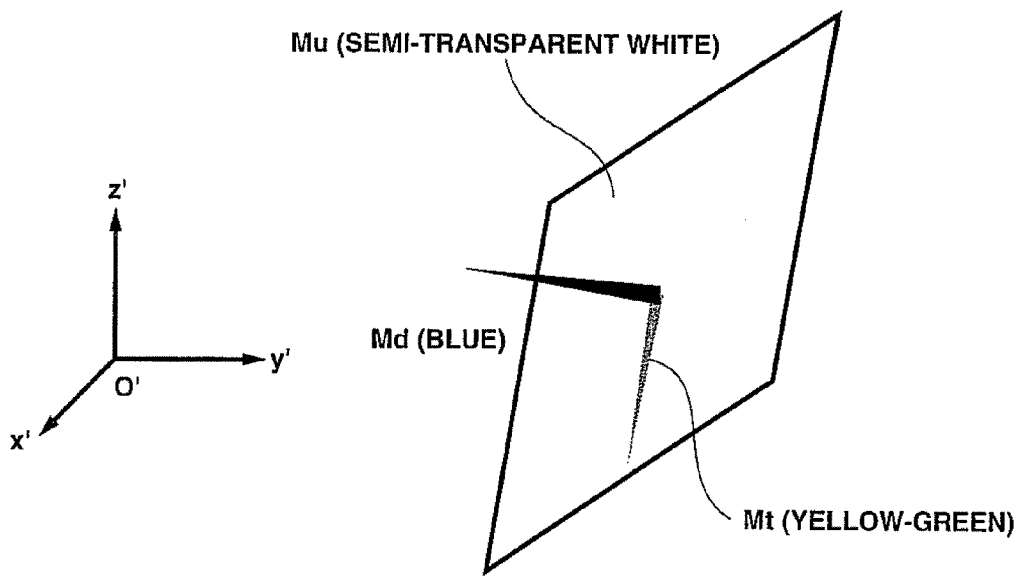

FIG.10B
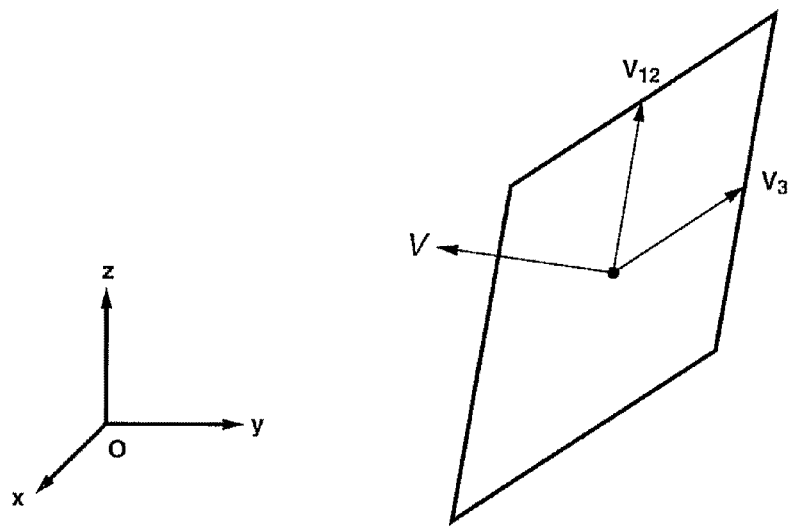
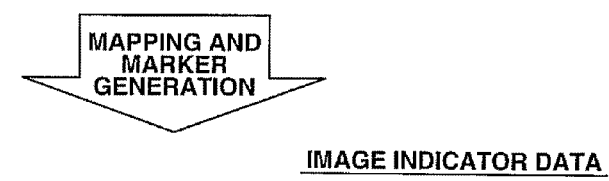
MAPPING AND MARKER GENERATION
IMAGE INDICATOR DATA
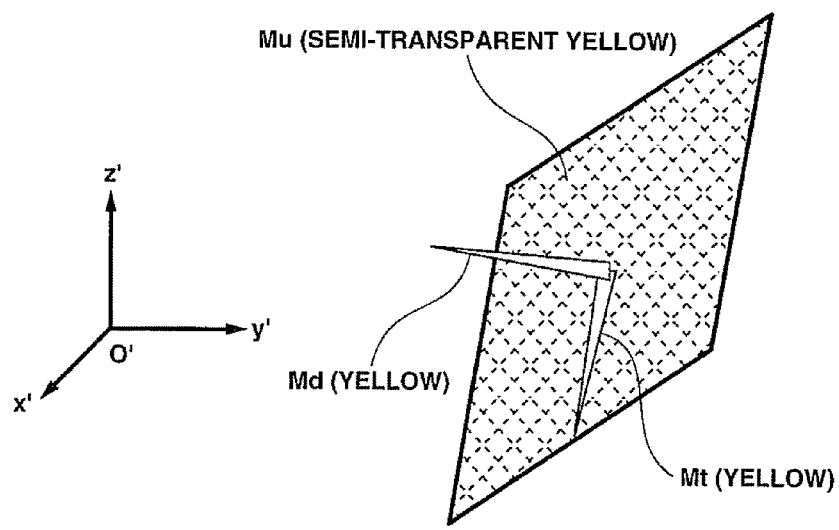

FIG.10C
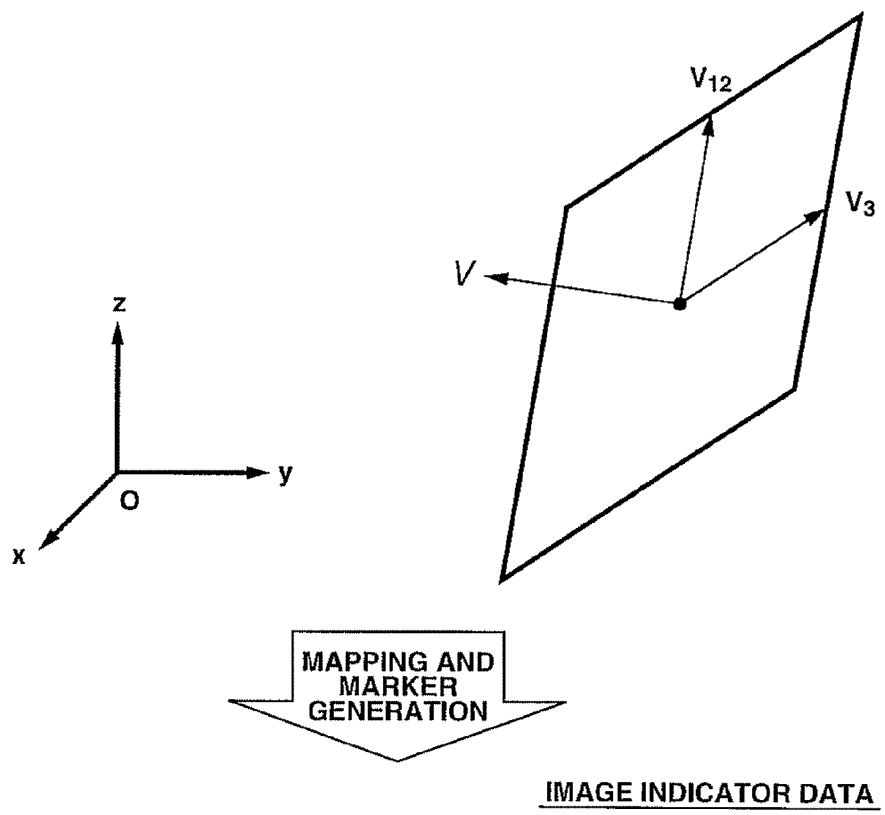
MAPPING AND MARKER GENERATION
IMAGE INDICATOR DATA
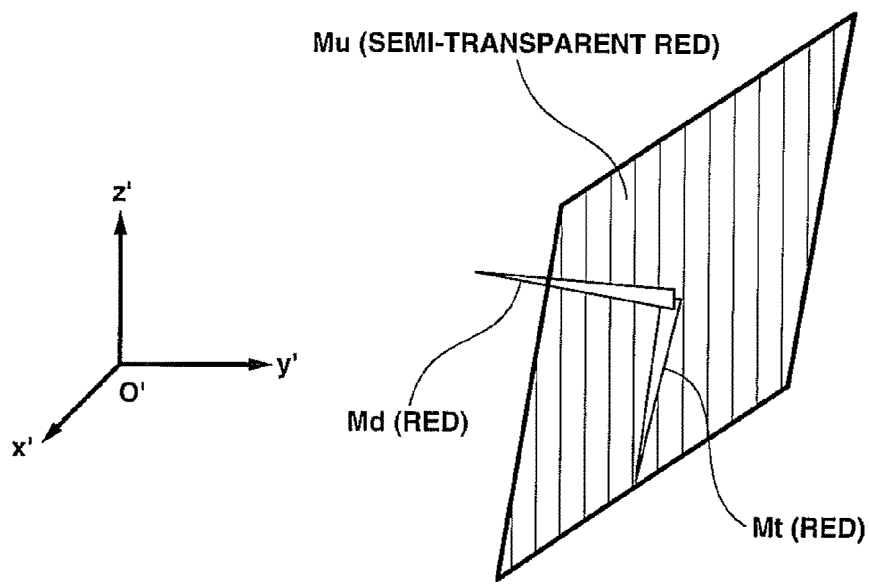

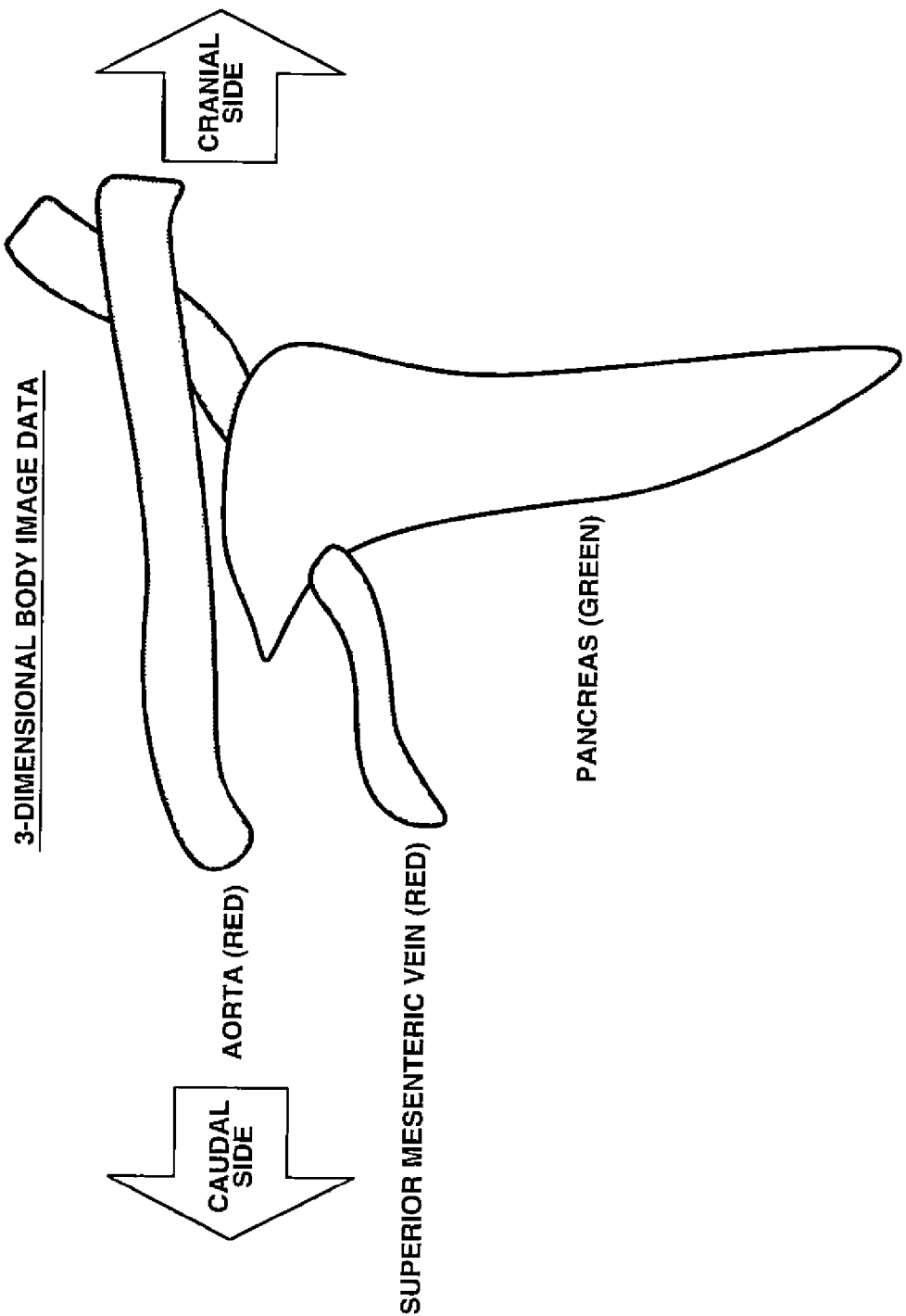

3-DIMENSIONAL GUIDE IMAGE DATA
(OBSERVED FROM CAUDAL SIDE OF TEST SUBJECT)
(ULTRASOUND TOMOGRAPHIC IMAGE MARKER: NON-SQUARELY-FACE NON-TRANSPARENT DISPLAY)

MEDICAL SYSTEM AND METHOD FOR GENERATING MEDICAL GUIDE IMAGE

CROSS REFERENCE TO RELATED APPLICATION

This application claims benefit of Japanese Application No. 2007-337659 filed on Dec. 27, 2007, the contents of which are incorporated herein by reference.

BACKGROUND OF THE INVENTION

1. Field of the Invention

The present invention relates to a medical system and a method for generating a medical guide image, and in particular to a medical system capable of acquiring information relating to an anatomical position and/or orientation of a medical image and the medical guide image generating method used in the medical system.

2. Description of the Related Art

Body cavity probes such as endoscopes capable of acquiring optical images of a test subject and ultrasound endoscopes capable of acquiring a tomographic image of the test subject are configured to allow insertion into body cavities such as the alimentary tract, the bronchia, the pancreas and bile ducts and blood vessels. Conventionally, such endoscopes have been widely used in the observation of the body cavities, diagnosis of disease, and the like.

When it is difficult to deliver the body cavity probe to a desired site in the body cavity using only the information contained in the optical image and the tomographic image, a guide image is sometimes used to allow the distal end portion of the body cavity probe to be guided easily to the desired site.

Guide images are also used as means to help an operator estimate an anatomical position of an ultrasound tomographic image obtained by the ultrasound endoscope or an ultrasound diagnosis apparatus which forms ultrasound tomographic images by passing an ultrasound probe over the body surface.

An example of apparatus including a function for generating a guide image of the above-described type is described in Japanese Patent Application Laid-Open Publication No. 2006-149481.

Japanese Patent Application Laid-Open Publication No. 2006-149481 describes an ultrasound diagnostic apparatus capable of generating a guide image for showing an anatomical position and/or orientation in an ultrasound tomographic image based on the ultrasound tomographic image and reference images stored in advance as anatomical image data.

SUMMARY OF THE INVENTION

The medical system of the present invention includes: an image signal acquiring portion for acquiring a signal to generate an image corresponding to a picture of a subject within a test subject; an image generating portion for generating a real-time image of an inside of the subject body based on the signal acquired by the image signal acquiring portion; a detecting portion for detecting at least a position and an orientation of an image position and orientation detecting element in a position which is fixed relative to the image signal acquiring portion, and outputting a detection result as a detection value; a reference image data storage portion for storing reference image data made up of a plurality of anatomical images of the test subject; a guide image generating portion for generating a guide image to provide guide information about at least one of an anatomical position and orientation within the test subject of the real-time image, based on the detection value detected by the detecting portion and the reference image data; and a detection state notification information generating portion for generating detection state notification information to notify a detection state of the detection value detected by the detecting portion.

A medical guide image generating method of the present invention includes steps of: acquiring a signal to generate an image corresponding to a picture of a subject existing within a test subject; generating a real-time image of an inside of the test subject based on the acquired signal; after detecting at least a position and orientation of the image position and orientation detecting element in a fixed position, outputting a detection result as a detection value; and generating a guide image to provide guide information about at least one of an anatomical position and orientation within the test subject of the real-time image based on the detected detection value and reference image data made up of a plurality of anatomical images of the test subject; and generating detection state notification information to notify a detection state of the detection value.

BRIEF DESCRIPTION OF THE DRAWINGS

FIG. 10A is a diagram for explanation showing a manner in which image indicator data is generated by an image indicator generating circuit when a judgment of "normal" is returned by a position and orientation calculating apparatus;

FIG. 10B is a diagram for explanation showing a manner in which the image indicator data is generated by the image indicator generating circuit when a judgment of "low accuracy" is returned by the position and orientation calculating apparatus;

FIG. 10C is a diagram for explanation showing a manner in which the image indicator data is generated by the image indicator generating circuit when a judgment of "undetectable" is returned by the position and orientation calculating apparatus;

FIG. 12 is a diagram for explanation showing 3-dimensional body image data;

DETAILED DESCRIPTION OF THE PREFERRED EMBODIMENTS

The following describes embodiments of the invention with reference to the accompanying drawings.

First Embodiment

Figure 1:
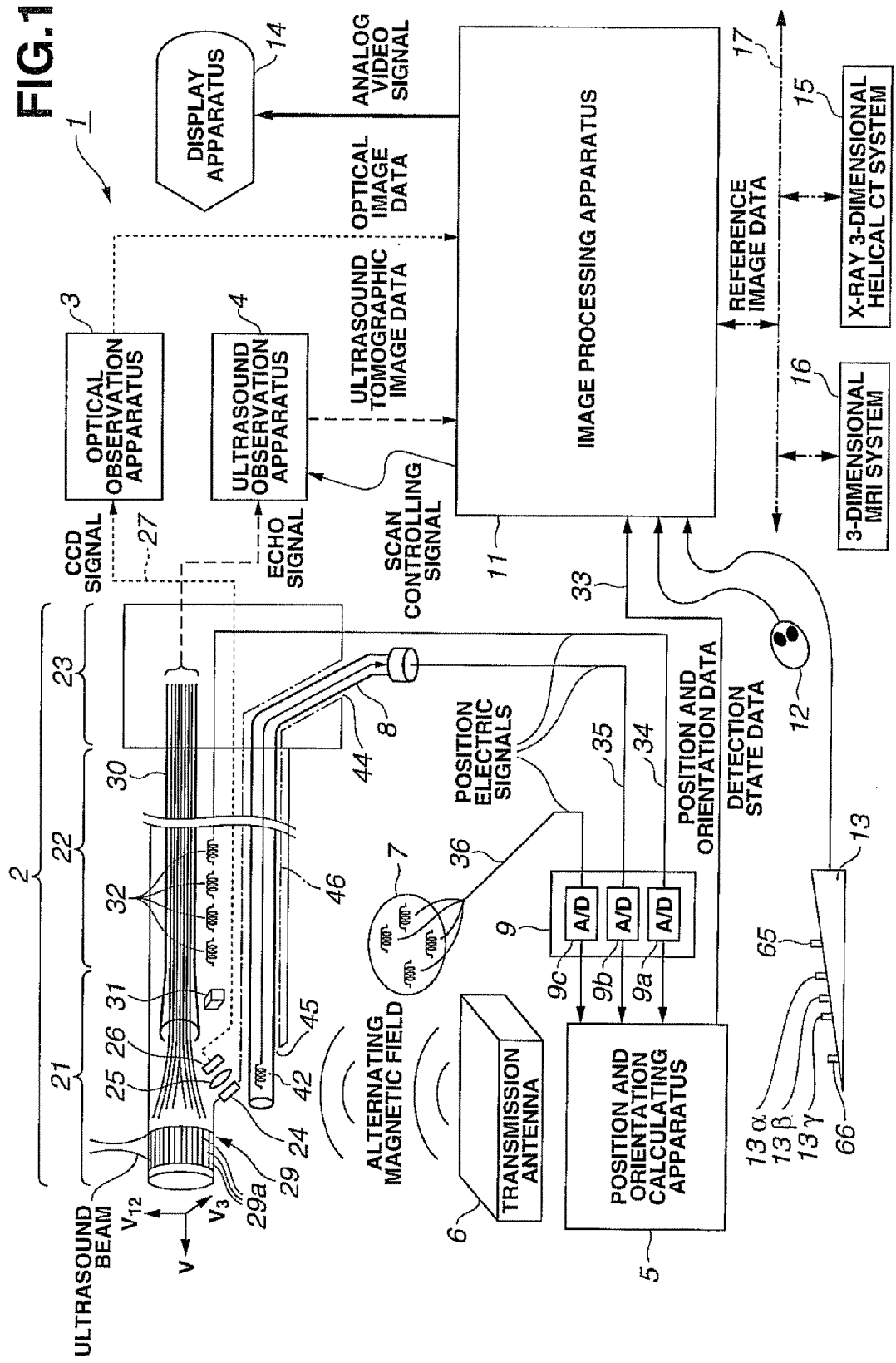
FIG. 1 is an overall configuration view showing a body cavity probe apparatus of a first embodiment of the invention.
Figure 2:
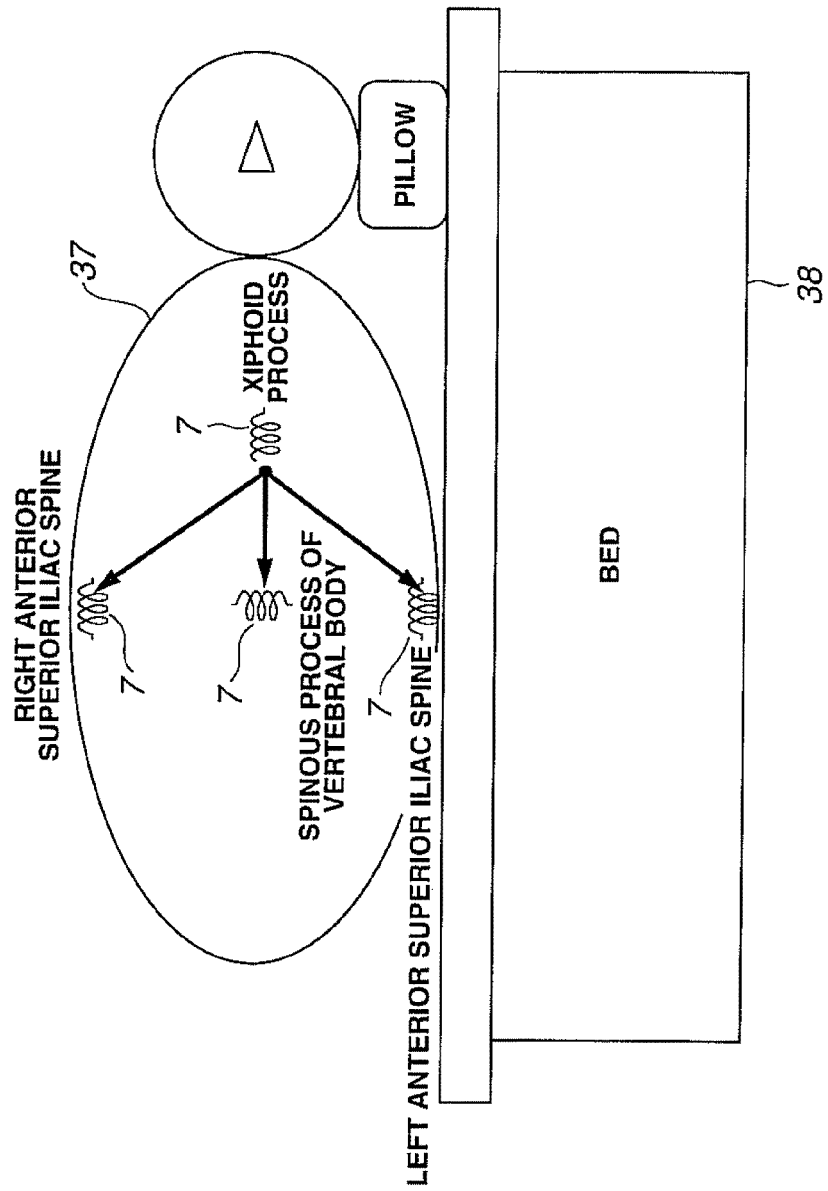
FIG. 2 is a diagram schematically showing an example of body surface detecting coils in use.
Figure 3:
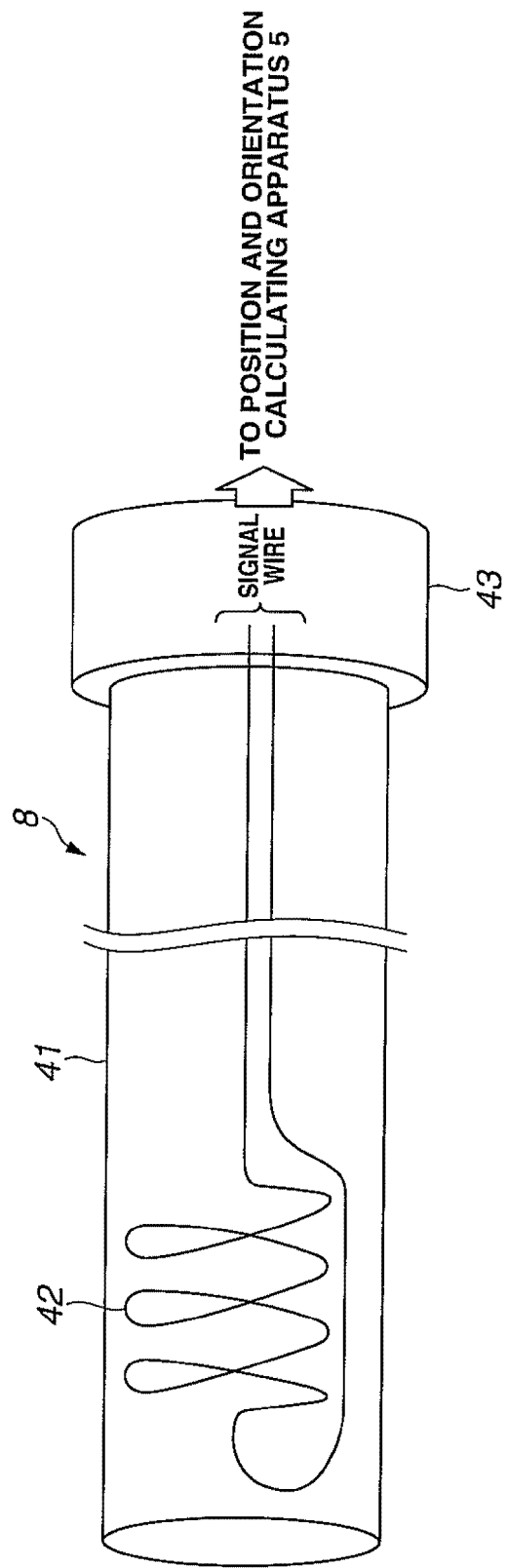
FIG. 3 is side view of a body cavity contacting probe.
Figure 4:
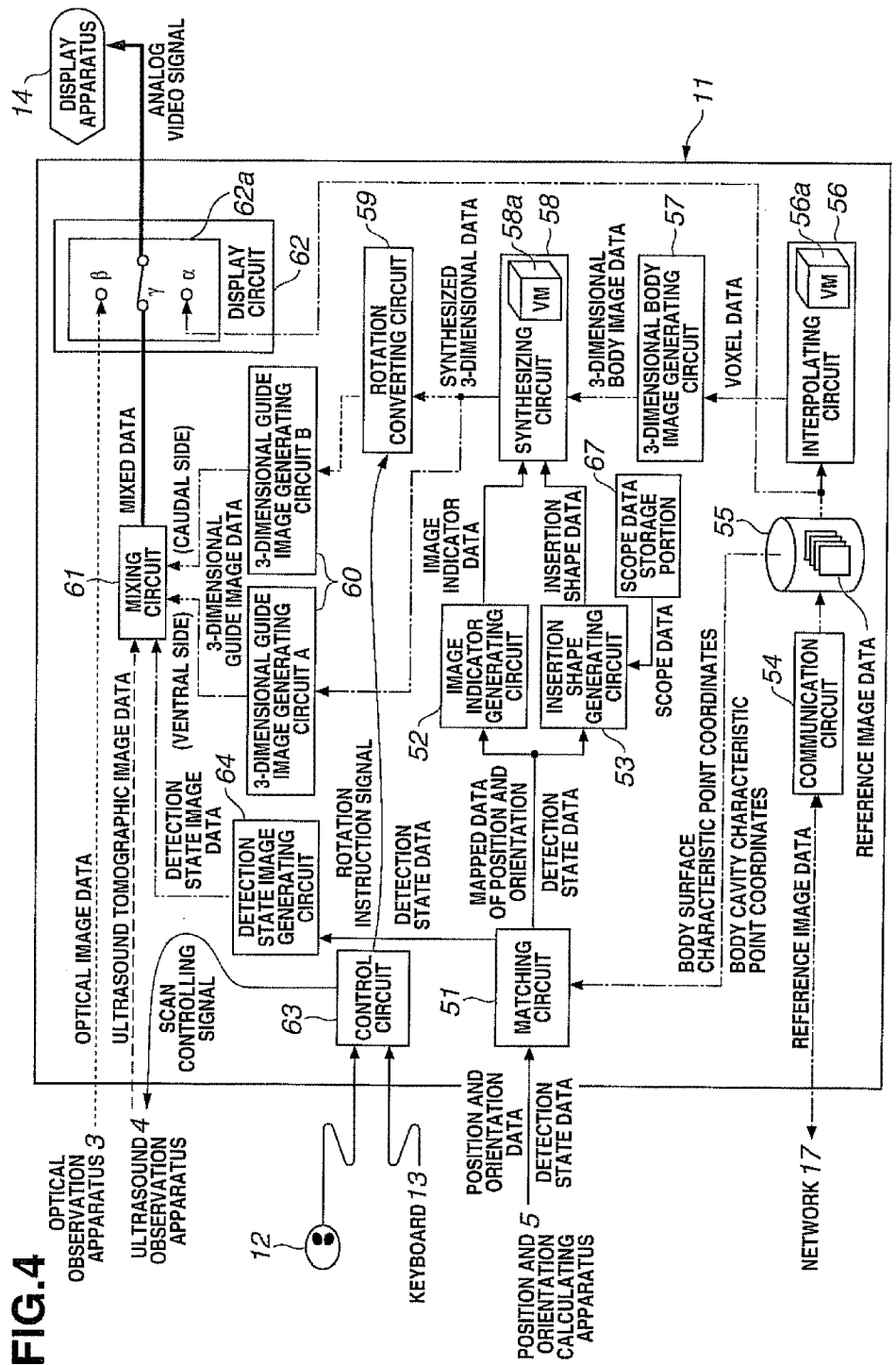
FIG. 4 is a block diagram showing a configuration of an image processing apparatus.
Figure 5:
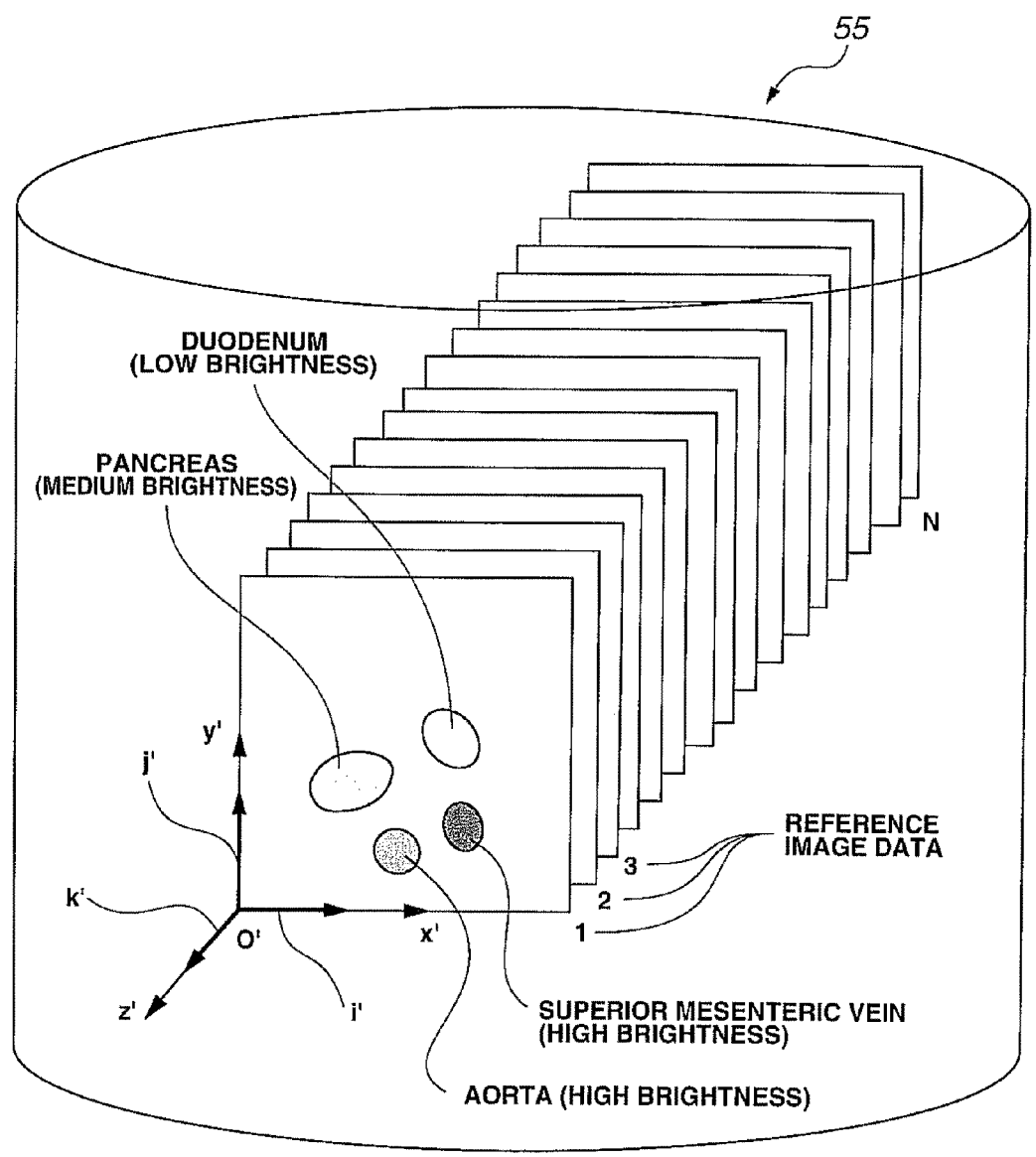
FIG. 5 is a diagram for explanation showing reference image data stored in a reference image storage portion.

FIGS. 1 to 21 relate to the first embodiment of the invention. FIG. 1 is an overall configuration view showing a body cavity probe apparatus of the first embodiment of the invention. FIG. 2 is a diagram showing an example of uses of body surface detecting coils. FIG. 3 is a diagram showing a body cavity contacting probe. FIG. 4 is a diagram showing a configuration of an image processing apparatus. FIG. 5 is a diagram showing reference image data stored in a reference image storage portion.

Figure 6:
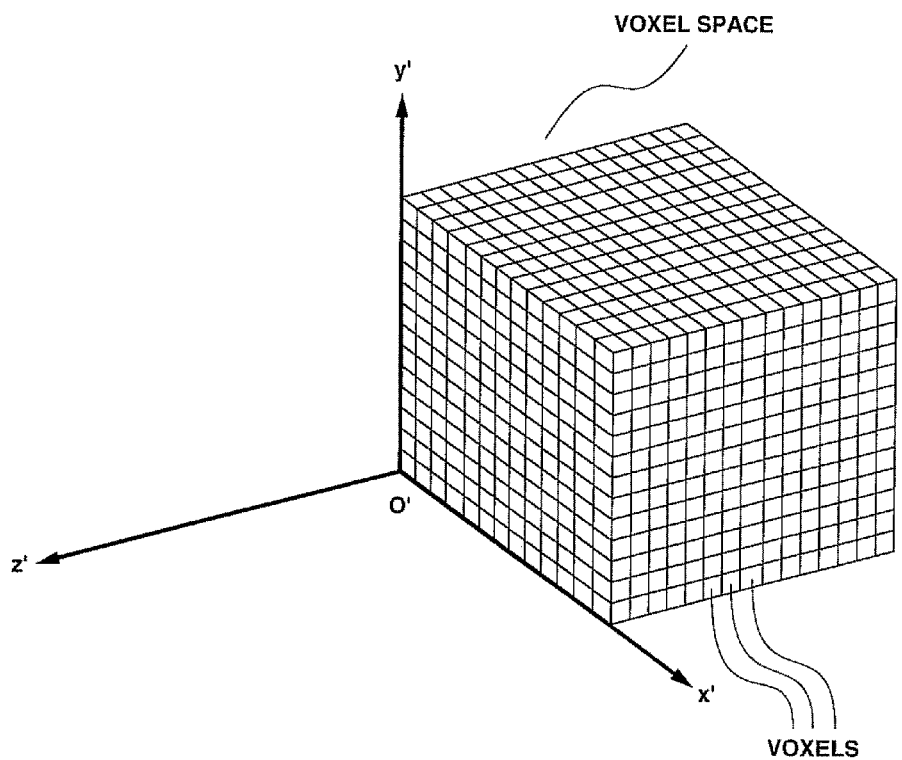
FIG. 6 is a diagram for explanation showing a voxel space.
Figure 7:
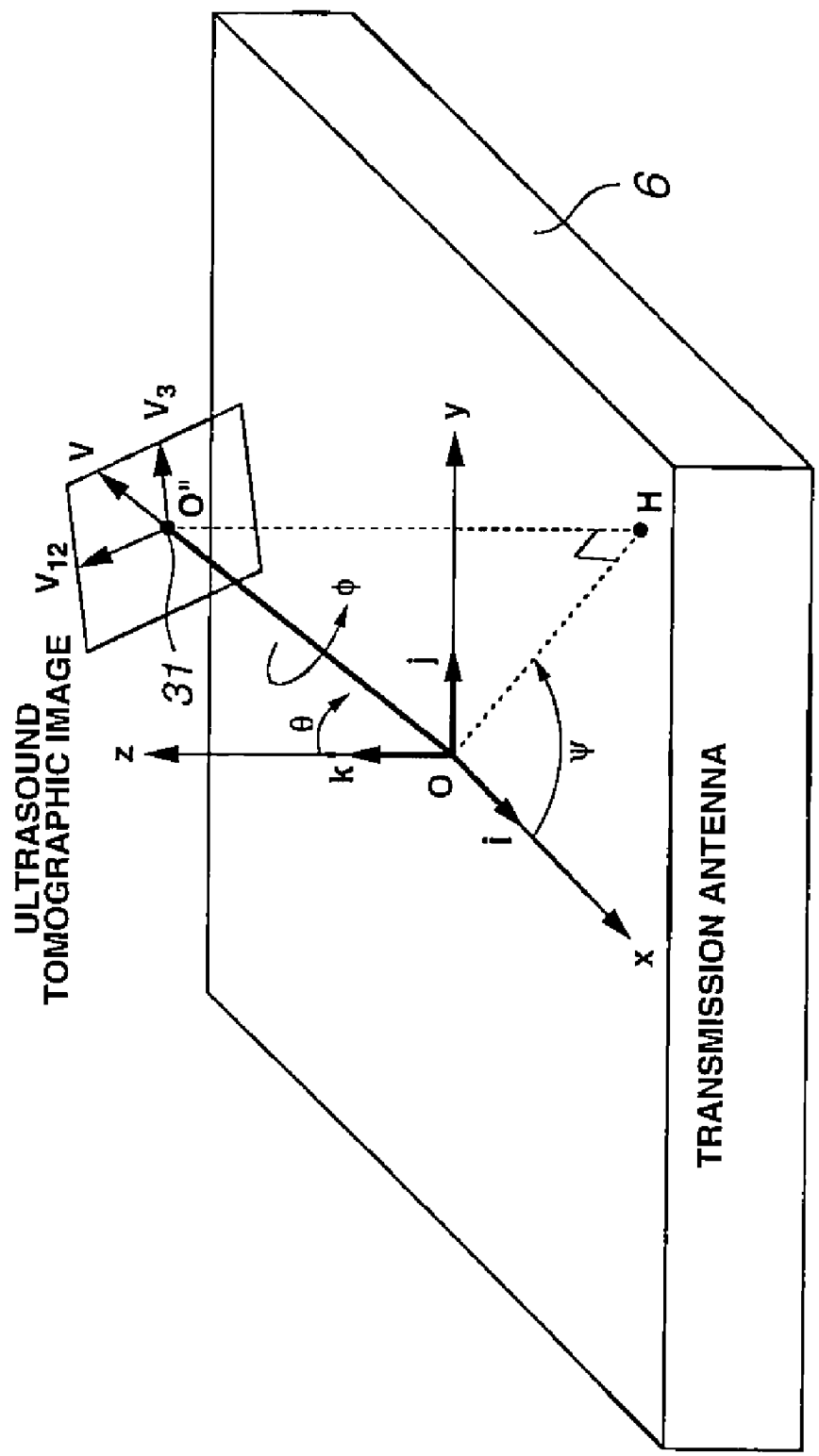
FIG. 7 is a diagram showing an orthonormal basis with an origin on a transmission antenna for expressing position and orientation data.
Figure 8:
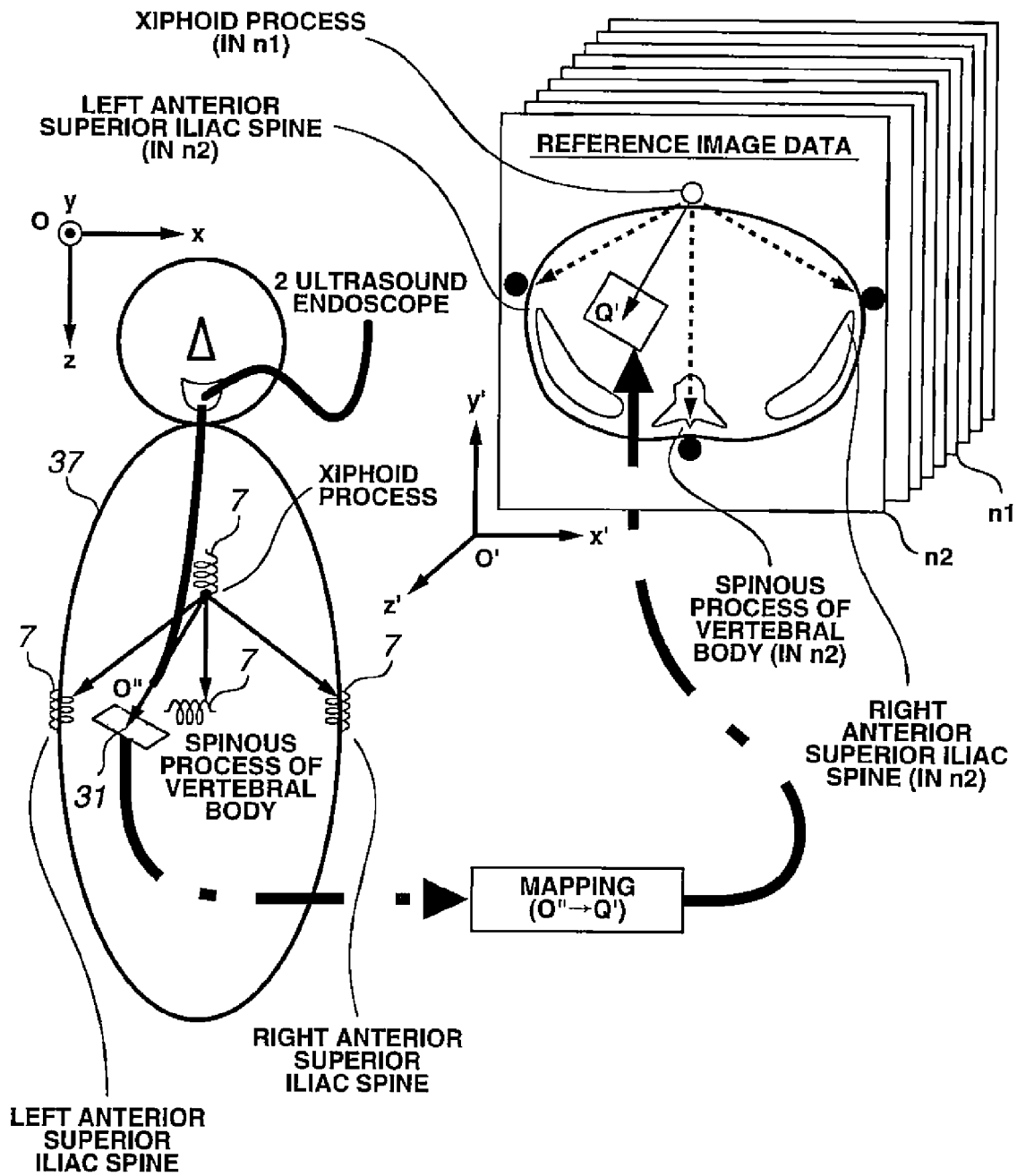
FIG. 8 is a diagram for explanation showing a manner in which a center of an ultrasound tomographic image on a test subject-side is mapped into voxel space.
Figure 9:
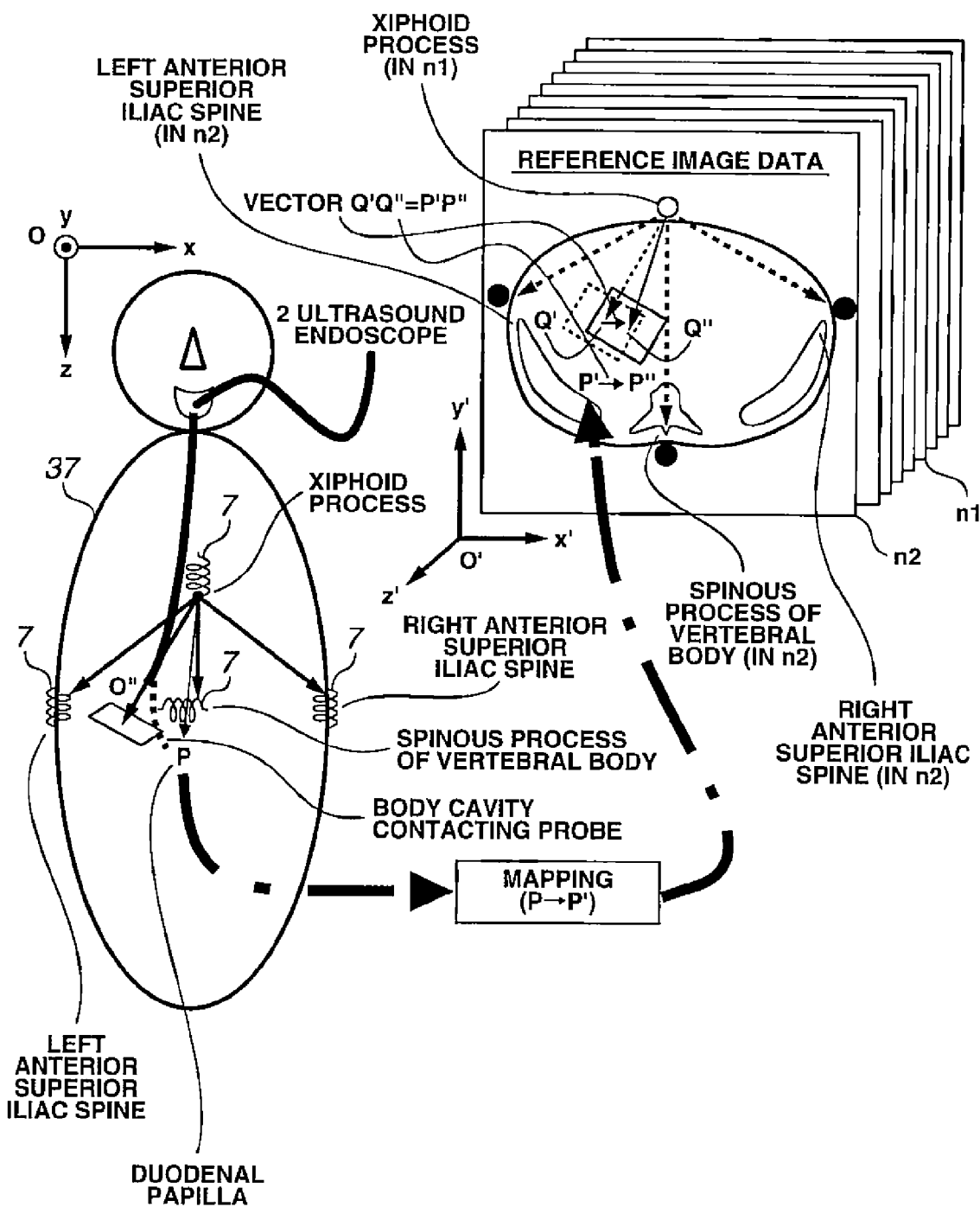
FIG. 9 is a diagram for explanation showing a manner in which a body cavity characteristic point on the test subject side is mapped into voxel space.

FIG. 6 is a diagram showing voxel space. FIG. 7 is a diagram showing an orthonormal basis with an origin on a transmission antenna for expressing position and orientation data. FIG. 8 is a diagram for explanation showing a manner in which a center of an ultrasound tomographic image on a test subject side is mapped into voxel space. FIG. 9 is a diagram showing a manner in which a body cavity characteristic point on a test subject side is mapped into voxel space. FIG. 10A is a diagram showing a manner in which image indicator data is generated by an image indicator generating circuit when a judgment of "normal" is returned by a position and orientation calculating apparatus. FIG. 10B is a diagram showing a manner in which the image indicator data is generated by the image indicator generating circuit when a judgment of "low accuracy" is returned by the position and orientation calculating apparatus. FIG. 10C is a diagram showing a manner in which the image indicator data is generated by the image indicator generating circuit when a judgment of "undetectable" is returned by the position and orientation calculating apparatus.

Figure 11A:
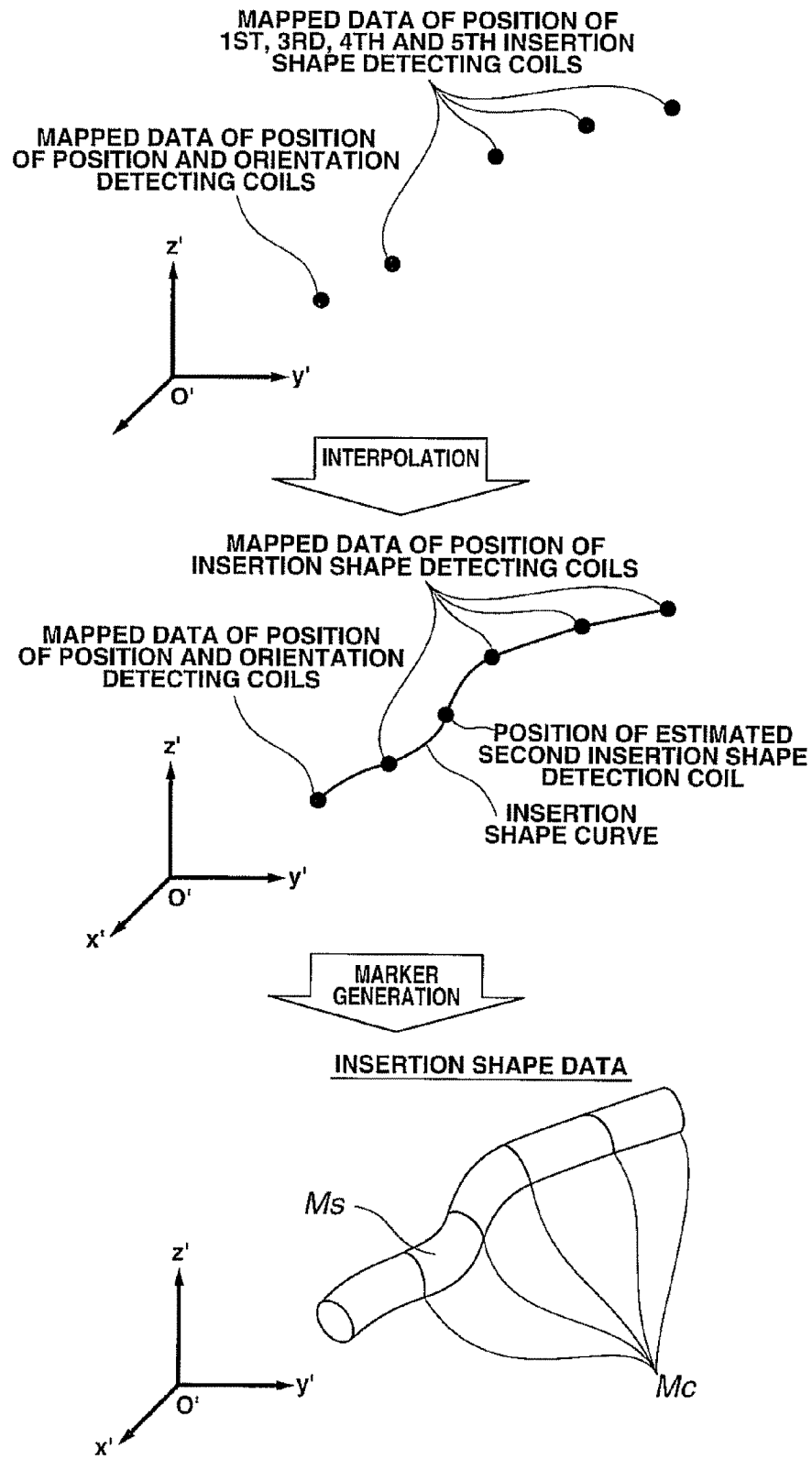
FIG. 11A is diagram for explanation showing a manner in which insertion shape data is generated by an insertion shape generating circuit.
Figure 11B:
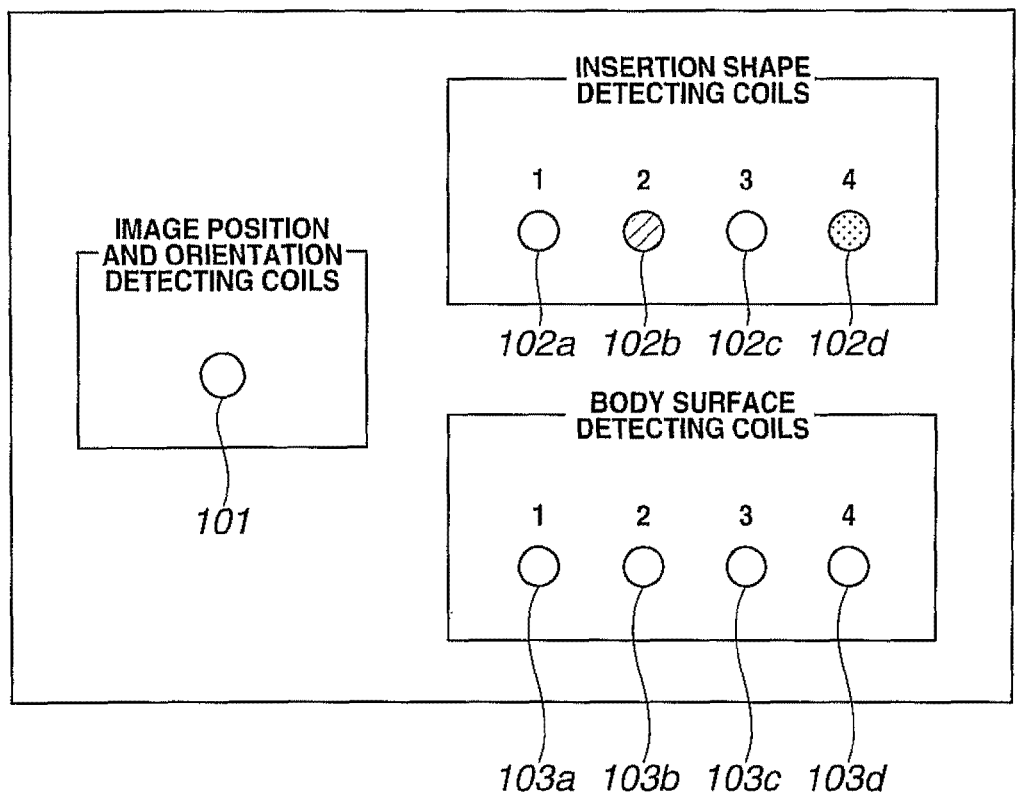
FIG. 11B is a diagram showing an example of a detection state image generated by a detection state image generating circuit.
Figure 13:
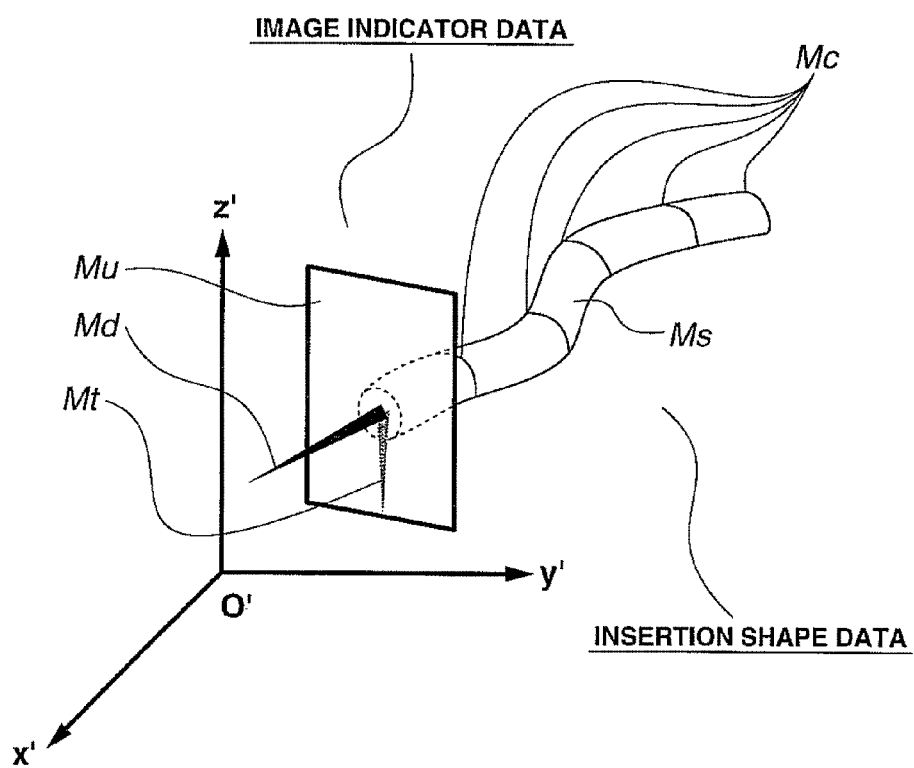
FIG. 13 is a diagram for explanation showing a manner in which the image indicator data and the insertion shape data are embedded in voxel space in synthesis memory by a synthesizing circuit.
Figure 14:
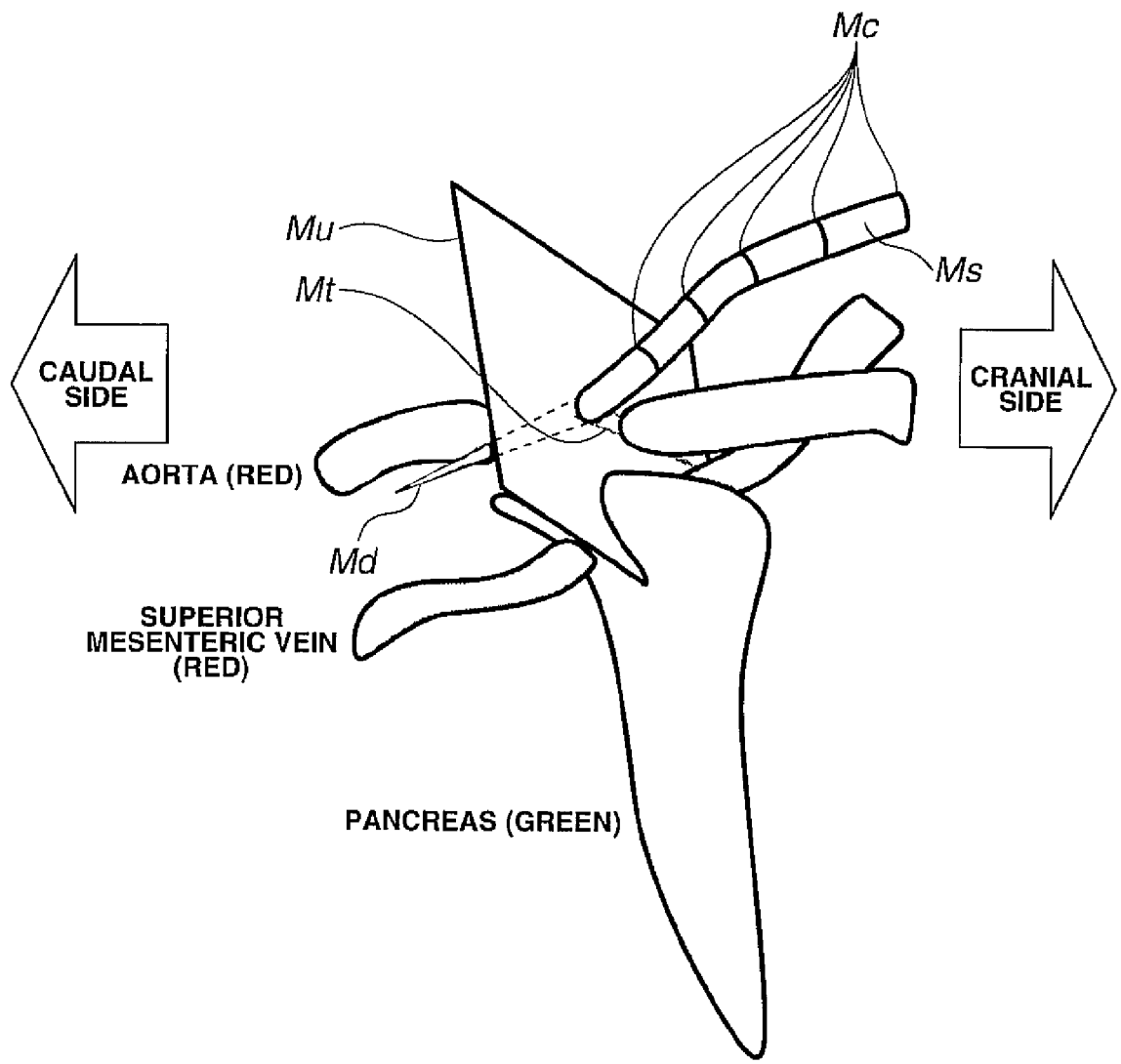
FIG. 14 is a diagram for explanation showing 3-dimensional guide image data for a case in which the test subject is observed from a ventral side.
Figure 15:
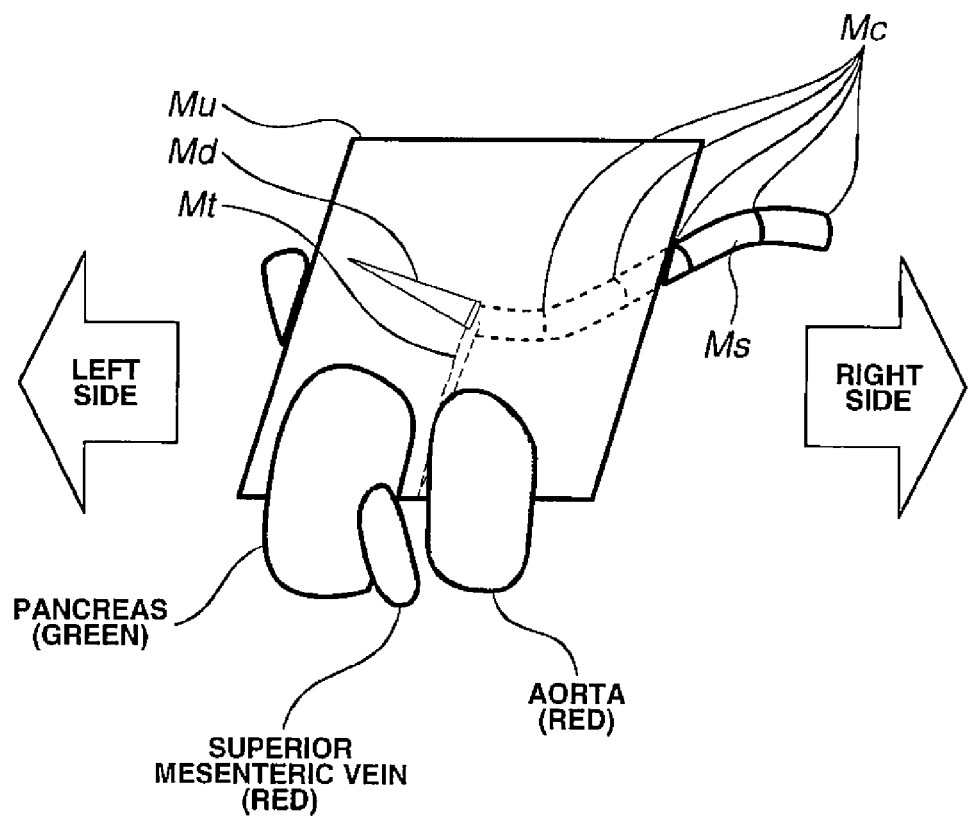
FIG. 15 is a diagram for explanation showing the 3-dimensional guide image data for a case in which the test subject is observed from a caudal side.

FIG. 11A is diagram showing a manner in which insertion shape data is generated by an insertion shape generating circuit. FIG. 11B is a diagram showing an example of a detection state image generated by a detection state image generating circuit. FIG. 12 is a diagram showing 3-dimensional body image data. FIG. 13 is a diagram showing a manner in which the image indicator data and the insertion shape data are embedded in voxel space in synthesis memory by a synthesizing circuit. FIG. 14 is a diagram showing the 3-dimensional guide image data for a case in which the test subject is observed from a ventral side. FIG. 15 is a diagram showing the 3-dimensional guide image data for a case in which the test subject is observed from a caudal side.

Figure 16:
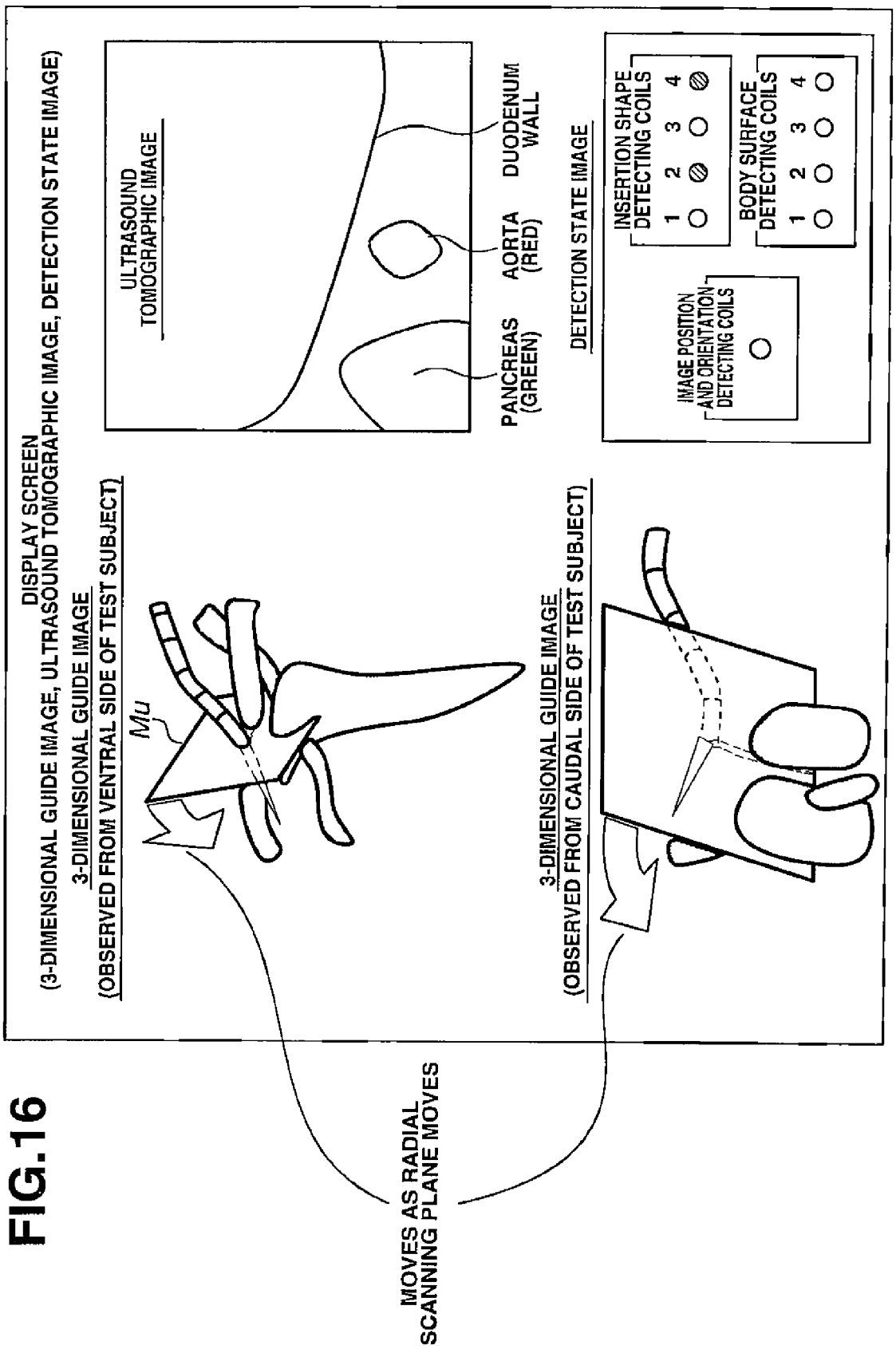
FIG. 16 is a diagram showing the 3-dimensional guide image, the ultrasound tomographic image, and the detection state image displayed on a display apparatus.
Figure 17:
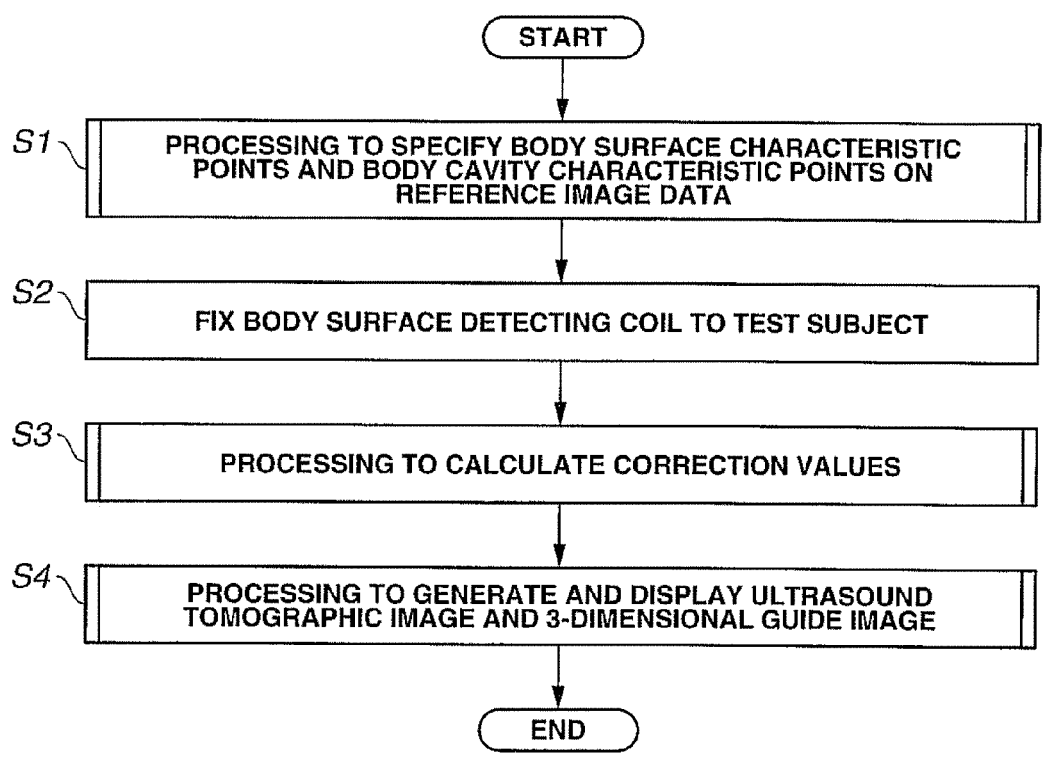
FIG. 17 is a flowchart showing overall processing of the present embodiment.
Figure 18:
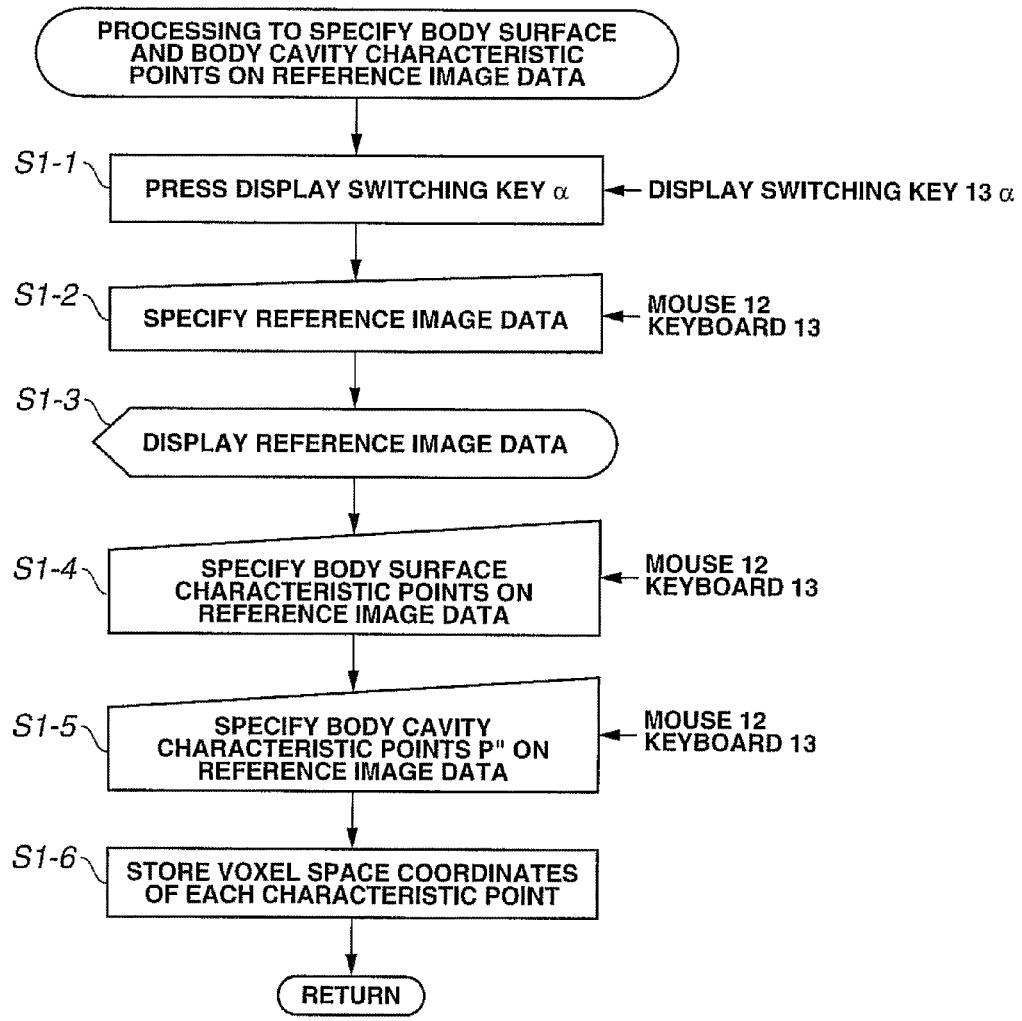
FIG. 18 is a flowchart showing specific processing corresponding to the processing for specifying body surface characteristic points and a body cavity characteristic point on the reference images shown in FIG. 17.
Figure 19:
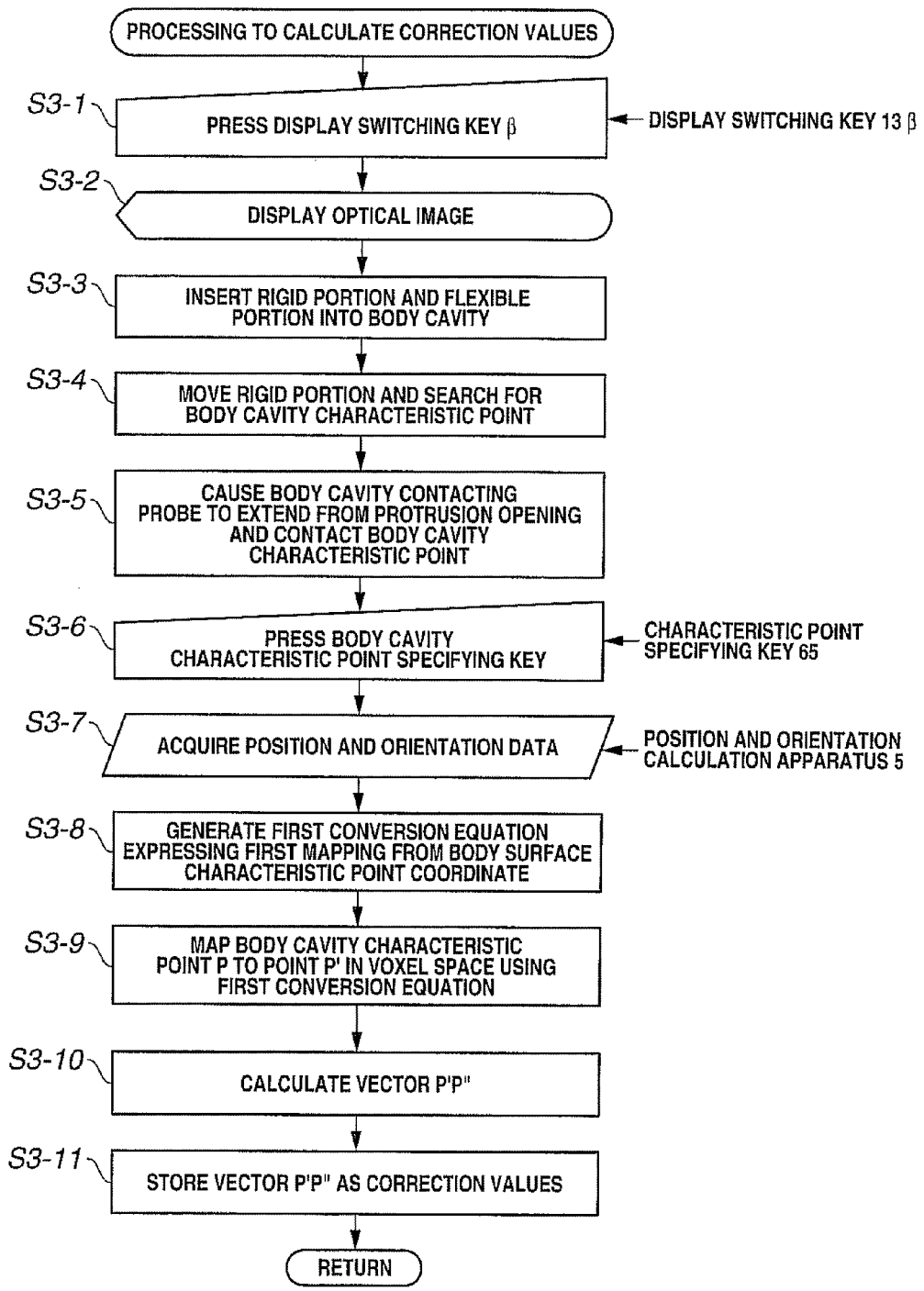
FIG. 19 is a flowchart showing specific processing corresponding to correction value calculation processing in FIG. 17.
Figure 20:
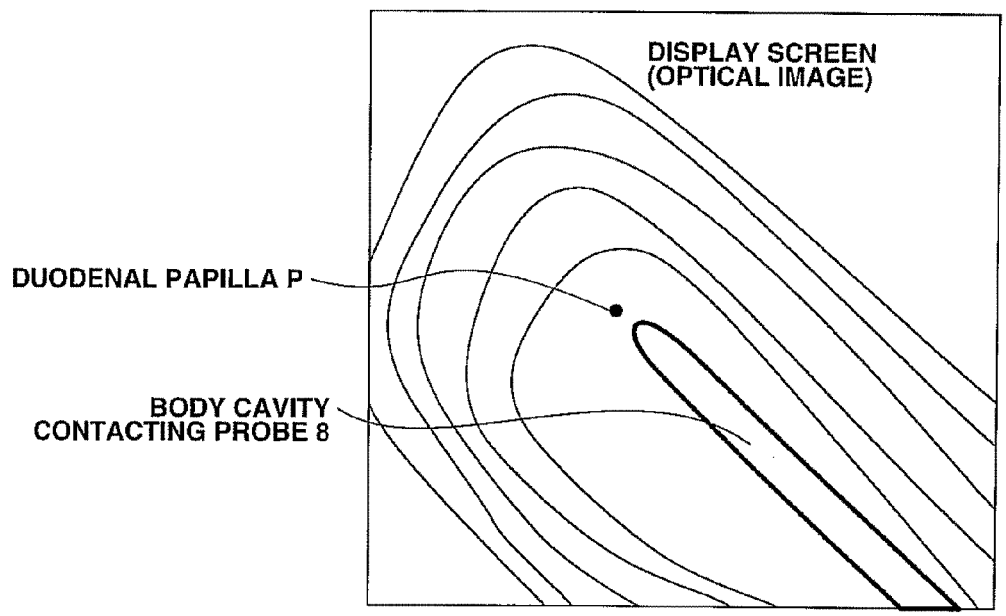
FIG. 20 is a diagram for explanation of the processing in FIG. 19.
Figure 21:
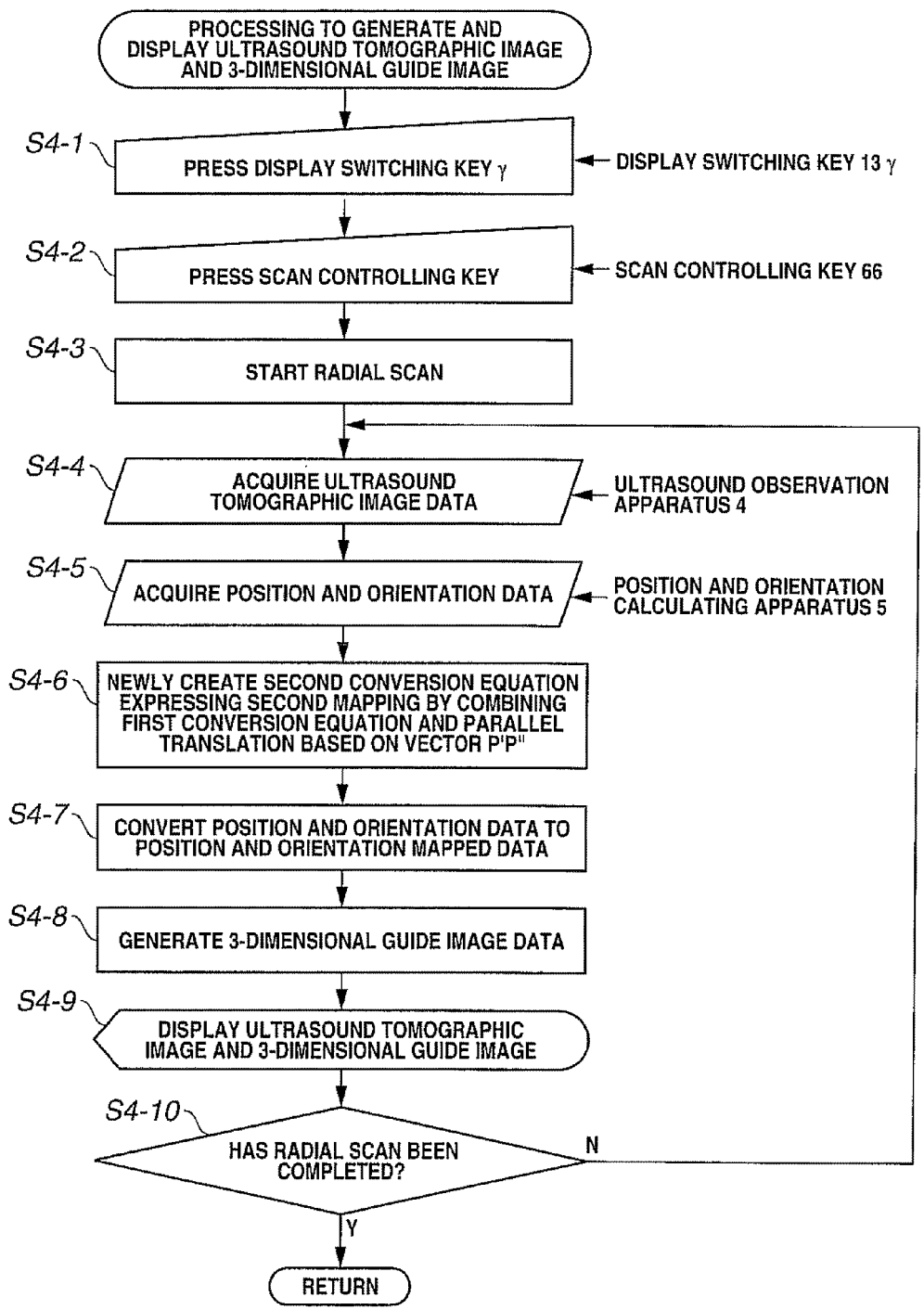
FIG. 21 is a flowchart showing specific processing corresponding to the processing in FIG. 17 for generating and displaying the ultrasound tomographic image and a 3-dimensional guide image.

FIG. 16 is a diagram showing the 3-dimensional guide image, the ultrasound tomographic image, and the detection state image displayed on a display apparatus. FIG. 17 is a flowchart showing overall processing of the present embodiment. FIG. 18 is a flowchart showing specific processing corresponding to the processing for specifying body surface characteristic points and a body cavity characteristic point on the reference images shown in FIG. 17. FIG. 19 is a flowchart showing specific processing corresponding to the correction value calculation processing in FIG. 17. FIG. 20 is a diagram for explaining the processing in FIG. 19. FIG. 21 is a flowchart showing specific processing corresponding to the processing in FIG. 17 for generating and displaying the ultrasound tomographic image and 3-dimensional guide image.

First, the configuration of a body cavity probe apparatus 1 of the first embodiment of the invention is described.

As shown in FIG. 1, the body cavity probe apparatus 1 as the medical system includes an electronic radial-scanning type ultrasound endoscope 2 as a body cavity probe, an optical observation apparatus 3, an ultrasound observation apparatus 4, a position and orientation calculating apparatus 5, a transmission antenna 6, body surface detecting coils 7, a body cavity contacting probe 8, an A/D unit 9, an image processing apparatus 11, a mouse 12, a keyboard 13 and a display apparatus 14. Each portion of the body cavity probe apparatus 1 is connected by signal wires.

An X-ray 3-dimensional helical computer tomography system 15 and a 3-dimensional magnetic resonance imaging system 16 are provided externally to the body cavity probe apparatus 1. An image processing apparatus 11 of the body cavity probe apparatus 1, the X-ray 3-dimensional helical computer tomography system 15 and the 3-dimensional magnetic resonance imaging system 16 are connected via a high-speed network 17 such as an optical communication, an ADSL network or the like.

The ultrasound endoscope 2 is configured to allow insertion into the esophagus, the stomach, the duodenum, or the like, and includes a rigid portion 21 which is provided at a distal most end and formed from a rigid material such as stainless steel, an elongated flexible portion 22 which is connected to a proximal end side of the rigid portion 21 and formed from a flexible material, and an operation portion 23 which is connected to the proximal end side (near side) of the flexible portion 22 and is formed from a rigid material. Note that the insertion portion in the ultrasound endoscope 2 is configured of the rigid portion 21 and the flexible portion 22.

The rigid portion 21 of the ultrasound endoscope 2 contains an image signal acquiring portion which optically picks up a picture of a subject and acquires an image signal corresponding to the picture of the subject in the manner described below.

An optical observation window 24 formed using cover glass is provided in the rigid portion 21. Further, an object lens 25 for forming an optical image and an image pickup device, such as a CCD (charge coupled device) camera 26, positioned at the image formation position of the object lens 25 are provided on the proximal side of the optical observation window 24. An illumination light output window (illumination window), which is not shown in the drawings, for emitting illumination light supplied from a light source (not shown) towards the subject within the body cavity is provided next to the optical observation window 24.

The CCD camera 26 is connected to the optical observation apparatus 3 via a signal wire 27. The illumination window (not shown) is configured so that the body cavity is lit by the illumination light. An image of a surface of the body cavity, which is the subject, passes through the optical observation window 24 and the object lens 25 and forms on the CCD camera 26. Then, the CCD signal outputted from the CCD camera 26, which corresponds to the image of the body cavity surface, passes through the signal wire 27 and is outputted to the optical observation apparatus 3, which is an image generating portion for generating a real-time optical image.

The rigid portion 21 of the ultrasound endoscope 2 also contains an image signal acquiring portion for acoustic imaging of the subject. The image signal acquiring portion acquires an echo signal as an image signal that corresponds to the picture of the subject.

The cylindrical distal end section, for example, of the rigid portion 21 is divided to form narrow rectangular sections. A group of ultrasound transducers is also provided on the distal end section in a ring-form array around an insertion axis. The group of ultrasound transducers forms an ultrasound transducer array 29.

Ultrasound transducers 29a which form the ultrasound transducer array 29 are each connected to a corresponding signal wire 30. The signal wires 30 are each connected via the operation portion 23 to the ultrasound observation apparatus 4, which is an image generating portion for generating real-time images from ultrasound. Note that center of the ring of the ultrasound transducer array 29 is the center of rotation of an ultrasound beam of a radial scan which is described in a later section.

Here, a standard orthonormal basis (unit vectors in each direction) made up of the vectors $V$, $V_3$ and $V_{12}$ and fixed at the rigid portion 21 is defined as shown in FIG. 1.

Thus, the vector $V$ which is parallel to the longitudinal direction (insertion axis direction) of the rigid portion 21 is, as described in a later section, a normal direction vector of the ultrasound tomographic image. Further, the vector $V_3$ is a three o'clock direction vector in the ultrasound tomographic image. Moreover, the vector $V_{12}$ is a twelve o'clock direction vector of the ultrasound tomographic image.

The rigid portion 21 further includes an image position and orientation detecting coil 31 as an image position and orientation detecting element for the ultrasound transducer array 29. The image position and orientation detecting coil 31 are fixed in a location near to the center of the ring formed by the ultrasound transducer array 29. Further, the image position and orientation detecting coil 31 includes integrally formed coils which are wound in two axes direction so as to orient in two directions (axes) of the vectors $V$ and $V_3$ to enable detection in the directions of both vector $V$ and vector $V_3$. With this configuration, the image position and orientation detecting coil 31 is able to detect the position and orientation (direction) of the image signal acquiring portion which makes use of ultrasound.

The flexible portion 22 includes a plurality of insertion shape detecting coils 32 along the insertion axis (of the flexible portion 22). The insertion shape detecting coils 32 may, for instance, be provided at fixed intervals.

As shown in FIG. 1, the insertion shape detecting coils 32 are all wound around single axis direction, and fixed within the flexible portion 22 in such a way that the direction of each winding axis matches the direction of the insertion axis of the flexible portion 22. The position of the rigid portion 21 can then be detected based on the positions of the image position and orientation detecting coil 31.

Hence, to be more exact, the insertion shape detecting element is configured from the image position and orientation detecting coil 31 provided within the rigid portion 21 and the plurality of insertion shape detecting coils 32 provided within the flexible portion 22.

For the sake of simplicity, the present embodiment will be described with reference to an example in which five insertion shape detecting coils 32 are provided within the flexible portion 22. Further, the plurality of insertion shape detecting coils 32 as part of the insertion shape detecting element may, for instance, only be provided in a distal end section of the flexible portion 22 of the ultrasound endoscope 2 in order to detect the insertion shape of the distal end section of the insertion portion. Moreover, when a bendable bending portion is provided in proximity to the distal end of the flexible portion 22, the plurality of insertion shape detecting coils 32 may only be provided in proximity to the bending portion.

The body cavity probe apparatus 1 of the present embodiment is configured to detect the insertion shape using a magnetic field. In the detection, the body cavity probe apparatus 1 employs the plurality of insertion shape detecting coils 32 as the insertion shape detecting element. With this arrangement, the body cavity probe apparatus 1 of the present embodiment is able to detect the insertion shape of the ultrasound endoscope 2 without exposing the operator or the patient (test subject) to radiation.

The position and orientation calculating apparatus 5 configures a detecting portion for detecting a position, orientation, and the like of the image position and orientation detecting coil 31. The position and orientation calculating apparatus 5 is connected via signal wires to a transmission antenna 6, a plurality of A/D units 9a, 9b and 9c which make up the A/D unit 9, and the image processing apparatus 11 which includes an insertion shape generating portion, a 3-dimensional image generating portion, a synthesizing portion, an image indicator generating portion and the like. The position and orientation calculating apparatus 5 and the image processing apparatus 11 are connected via a cable 33 of the RS-233C standard or the like.

The transmission antenna 6 is equipped with a plurality of transmission coils (not shown) with winding axes of differing orientation which are, for instance, contained within a box-like casing. The transmission coils provided within the transmission antenna 6 are each connected to the position and orientation calculating apparatus 5.

The A/D unit 9$i$ (where i=a to c) is made up of an amplifier (not shown) which amplifies an inputted analog signal and an analog to digital converting circuit (not shown) which samples the amplified analog signal and generates digital data.

The A/D unit 9$a$ is separately connected to the image position and orientation detecting coil 31 and to each of the insertion shape detecting coils 32. The A/V unit 9$b$ is connected to the elongated body cavity contacting probe 8 via a signal wire 35. The A/D unit 9$c$ is connected separately to each of the plurality of body surface detecting coils 7 via signal wires 36.

Note that the arrows in FIG. 1 and the later-described FIG. 4 show the flow of signals and data which are described below.

(a) Firstly, a dotted line indicates a flow of signals or data relating to the optical image.

(b) Secondly, a dashed line indicates a flow of signals or data relating to an ultrasound tomographic image.

(c) Thirdly, a solid line indicates a flow of signals or data relating to position, or data processed and generated from such signals or data.

(d) Fourthly, a line composed of long and short dashes indicates a flow of reference image data, or data processed and generated from such data.

(e) Fifthly, a thick solid line indicates a flow of signals or data relating to a final display of the synthesized ultrasound tomographic image data (described later) and the 3-dimensional guide image data (described later).

(f) Sixthly, a curved line indicates a flow of signals or data relating to other control functions.

FIG. 2 shows the body surface detecting coils 7 which form a test subject detecting element.

The body surface detecting coils 7 include four coils, each of which is wound around a different axis direction. The coils of the body surface detecting coils 7 are removably fixed to characteristic points of the body surface, specifically around the abdomen (hereinafter simply referred to as body surface characteristic points) of the test subject 37 with removable tape, belts, bands or the like, and magnetic fields generated at the body surface characteristic points are used in position detection.

Note that in upper endoscopy, the test subject 37 normally lies left-side down on the bed 38 in what is known as the left lateral position and the endoscope is inserted into the mouth. For this reason, FIG. 2 is drawn to schematically show the test subject 37 in the left lateral position.

Note that in the present embodiment, four body surface characteristic points are used. The four body surface characteristic points are the "xiphoid process" which characterizes the top of the spine, the "left anterior superior iliac spine" of the left side of the pelvis, the "right anterior superior iliac spine" of the right side of the pelvis and the "spinous process of vertebral body" on the spine between the left and right anterior superior iliac spines.

The positions of the above-described four points which are the body surface characteristic points can be specified by palpation of the test subject 37 by the operator. The above-described four points are not coplanar, and three vectors pointing towards the other characteristic points from the xiphoid process form basis vectors of an un-orthogonal reference frame with the xiphoid process as the origin. The un-orthogonal reference frame may, for instance, have the form shown by thick lines in FIG. 2.

FIG. 3 shows the body cavity contacting probe 8. The body cavity contacting probe 8 includes a cylindrical housing 41 which is constructed from a flexible material. A body cavity detecting coil 42 is provided fixed within a distal end portion of the cylindrical housing 41. Further, a connector 43 is provided at a proximal end portion of the cylindrical housing 41.

As shown in FIG. 3, the body cavity detecting coil 42 is made up of a coil wound around a single axis direction and fixed to the distal end portion of the body cavity contacting probe 8. The body cavity detecting coil 42 is fixed in such a way that the winding axis direction matches an insertion axis direction of the body cavity contacting probe 8. The body cavity detecting coil 8 is used for detecting the position of sites of interest touched by the tip of the body cavity contacting probe 8 within the body cavity.

As shown in FIG. 1, the ultrasound endoscope 2 has a tubular treatment instrument channel 46 which starts at the operation portion 23, passes through the flexible portion 22, and ends at the rigid portion 21. The treatment instrument channel 46 includes, in the operation portion 23, a treatment instrument insertion opening 44 (hereinafter referred to as the forceps opening for simplicity) which is a first opening and, in the rigid portion 21, a protrusion opening 45, which is a second opening. Forceps and the like can be introduced to the forceps opening 44 and (the distal end of) the forceps or the like can be caused to protrude from the protrusion opening 45.

Thus the body cavity contacting probe 8 can be inserted into the forceps opening 44 of the treatment instrument channel 46 and the distal end of the body cavity contacting probe 8 can be caused to protrude from the protrusion opening 45. The protrusion opening 45 is orientated in a way which ensures that the body cavity contacting probe 8 is positioned within the optical field of view of the optical observation window 24 when the body cavity contacting probe 8 protrudes from the protrusion opening 45.

FIG. 4 shows the image processing apparatus 11 which includes the insertion shape generating portion, the 3-dimensional image generating portion, the synthesizing portion, the image indicator generating portion, and the like.

The image processing apparatus 11 includes a matching circuit 51, an image indicator generating circuit 52, an insertion shape generating circuit 53, a communication circuit 54, a reference image storage portion 55, an interpolating circuit 56, a 3-dimensional body image generating circuit 57, a synthesizing circuit 58, a rotation converting circuit 59, a 3-dimensional image generating circuit 60 which generates 3-dimensional guide images corresponding to two differing viewing directions, a mixing circuit 61, a display circuit 62, a control circuit 63, a detection state image generating circuit 64, and a scope data storage portion 67. Note that the 3-dimensional image generating circuit 60 is made up of a 3-dimensional guide image generating circuit A and a 3-dimensional guide image generating circuit B as shown in FIG. 4. Thus, in the following, the two 3-dimensional guide image generating circuits included in the 3-dimensional image generating circuit 60 are described separately.

The matching circuit 51 receives input of position and orientation data and detection state data from the position and orientation calculating apparatus 5 which configures the detecting portion for detecting the position and orientation of the insertion shape detecting elements and the like. Note that the position and orientation data and the detection state data are described in a later section.

The matching circuit 51 calculates new position and orientation data in a 0'-x'y'z' orthogonal coordinate system by mapping the position and orientation data calculated in a 0-xyz orthogonal coordinate system in accordance with a predetermined conversion equation. This conversion equation is described in a later section.

The matching circuit 51 then outputs the new position and orientation data as position and orientation mapped data to the image indicator generating circuit 52 which generates the image indicator data and to the insertion shape generating circuit 53 which generates the insertion shape data.

The communication circuit 54 includes a high-capacity and high-speed communication modem and is connected, via a network 17, to the X-ray 3-dimensional helical computer tomography system 15 and the 3-dimensional MRI system 16 which generate 3-dimensional data of the body.

The reference image storage portion 55 is a hard disc drive or the like with a large data storing capacity. The reference image storage portion 55 has stored therein a plurality of reference image data as anatomical image information.

The reference image data is section image data of the test subject 37 of the type shown in FIG. 5. The reference image data is initially acquired by the X-ray 3-dimensional helical computer tomography system 15 and the 3-dimensional magnetic resonance imaging system 16, and is inputted to the reference image storage portion 55 via the network 17 and the communication circuit 54.

Note that the reference image data of the present embodiment is image data for sections perpendicular to the body axis of the test subject 37 (axis going through the head and the feet). The section images are rectangular with side lengths of several decimeters, and are taken at intervals of anywhere between 0.5 min and a few mm.

When obtaining the section images of the test subject 37, it is possible to reduce or eliminate the exposure of the test subject 37 to X-rays by repeated use of the 3-dimensional magnetic resonance imaging system 16 in place of the X-ray 3-dimensional helical computer tomography system 15.

In the following description, the reference image data shown in FIG. 5 in the reference image storage portion 55 are denoted using the numbers "1" to "N".

Here, as shown in FIG. 5, the plurality of reference image data are defined in an orthogonal coordinate system 0'-x'y'z' with an orthonormal basis (unit vectors i', j' and k' pointing along respective axes) with the origin 0' positioned in the bottom left corner of the $1^{st}$ reference image data.

As shown in FIG. 4, the interpolating circuit 56 and the synthesizing circuit 58 each include volume memories VM. In the following explanations the volume memory VM provided in the interpolating circuit 56 is referred to as interpolating memory 56a and the volume memory VM provided in the synthesizing circuit 58 is referred to as synthesizing memory 58a.

The volume memories VM are configured to allow storage of large volumes of data. Voxel space is allocated to part of the available storage areas in each volume memory VM. As shown in FIG. 6, the voxel space is made up of memory cells (hereinafter referred to as voxels), each of which has an address based on the orthogonal coordinate system 0'-x'y'z'.

The 3-dimensional body image generating circuit 57 which generates the 3-dimensional body images and the rotation converting circuit 59 which performs rotational conversions each include a high-speed processor (not shown) capable of performing with high speed image processing, such as extraction of voxels and pixels based on brightness, rotational conversion similarity transformation, and parallel translation.

The display circuit 62 includes a switch 62a for switching between inputs. The switch 62a has an input terminal α, an input terminal β, an input terminal γ, and a single output terminal. The input terminal α is connected to the reference image storage portion 55. The input terminal β is connected to an output terminal (not shown) of the optical observation apparatus 3 and the input terminal γ is connected to the mixing circuit 61. The output terminal of the switch 62a is connected to the display apparatus 14 which is a display portion capable of displaying the optical image, the ultrasound tomographic image, the 3-dimensional guide image and the like.

The control circuit 63 is connected to the various portions and circuits of the image processing apparatus 11 via signal wires (not shown) so as to be able to output instructions to the various portions and circuits. The control circuit 63 is also connected via control wires directly to the ultrasound observation apparatus 4, the mouse 12 and the keyboard 13.

As shown in FIG. 1, the keyboard 13 is equipped with a body cavity characteristic point specifying key 65, a scan controlling key 66, a display switching key 13a, a display switching key 13β, and a display switching key 13γ.

When any of the display switching keys 13α, 13β or 13γ is pressed, the control circuit 63 outputs, to the display circuit 62, an instruction to switch the switch 62a to the corresponding input terminal α, β or γ. Thus, the switch 62a is switched to the input terminal α when the display switching key 13α is pressed, to the input terminal β when the display switching key 13β is pressed and to the input terminal γ when the display switching key 13γ is pressed.

The following descriptions relate to the signals and data corresponding to the headings (a) to (f) (firstly to sixthly) used in an earlier section.

(a) First, the operations of the present embodiment are described by following the flow of the first signals and data indicated by the dotted lines in the drawings. These signals and data are related to the first optical image.

Illumination light supplied form the light source (not shown) is emitted through the illumination light window (not shown) of the rigid portion 21 into the optical field of view. The CCD camera 26 picks up an image of matter (subject) in the optical field of view, generates a CCD signal by photoelectric conversion, and outputs the generated CCD signal to the optical observation apparatus 3.

The optical observation apparatus 3 generates real-time image data for the optical field of view based on the inputted CCD signal, and outputs the data as optical image data to the input terminal β of the switch 62a of the display circuit 62 in the image processing apparatus 11.

(b) Next, the operations of the present embodiment are described by following the flow of the second signals and data relating to the ultrasound tomographic image.

When the scan controlling key 66 is pressed by the operator, the control circuit 63 outputs a scan controlling signal to the ultrasound observation apparatus 4 to instruct the ultrasound observation apparatus 4 to switch a radial scan on and off. The radial scan is described in a later section.

The ultrasound observation apparatus 4 selects a part and plurality of ultrasound transducers 29a which make up the ultrasound transducer array 29 and transmits an excitation signal in the form of voltage pulses.

The part and plurality of ultrasound transducers 29a receive the excitation signal and convert the excitation signal to ultrasound waves which are compressional waves in the medium.

During this process, the ultrasound observation apparatus 4 adds delays to the excitation signal so that the excitation signals arrive at the ultrasound transducers 29a at different times. The delay values (length of delay) is adjusted so that the ultrasounds wave excited in each ultrasound transducer 29a are combined in the test subject 37 to form a single ultrasound beam.

After being emitted from the ultrasound endoscope 2, the ultrasound beam is reflected from internal portions of the test subject 37. The reflected wave resulting from the reflection of the ultrasound beam enters the ultrasound transducers 29a along a path which is the direct opposite of the ultrasound beam.

Each ultrasound transducer 29a converts the incident reflected wave to an electronic echo signal and then outputs the echo signal to the ultrasound observation apparatus 4 on a path which is the direct opposite of the path taken by the excitation signal.

The ultrasound observation apparatus 4 reselects the ultrasound transducers 29a which contribute to forming the ultrasound beam so that the ultrasound beam rotates in a plane (hereinafter referred to as a radial scanning plane) which is perpendicular to the rigid portion 21 and the flexible portion 22 and includes the center of the ring of the ultrasound transducer array 29. After the reselection, the ultrasound observation apparatus 4 transmits further excitation signals. As the above-described operation is being performed in the ultrasound observation apparatus 4, the transmission angle of the ultrasound beam changes gradually. The so-called radial scan is then realized by continuous repetition of the above-described operations in the ultrasound observation apparatus 4.

The ultrasound observation apparatus 4 generates, as a real-time image, ultrasound tomographic image data for a single section perpendicular to the insertion axis of the rigid portion 21, and outputs the ultrasound tomographic image data to the mixing circuit 61 of the image processing apparatus 11. Here, the single section corresponds to a single radial scan by the ultrasound transducer array 29 and is based on the echo signals resulting from conversion of the reflected wave by the ultrasound transducers 29a. Note also that, as part of the generation, the ultrasound observation apparatus 4 performs processing to give the ultrasound tomographic image data a rectangular form.

As described above, in the present embodiment, the ultrasound observation apparatus 4 reselects the plurality of ultrasound transducers 29a which make a contribution to forming the ultrasound beam, and then transmits further excitation signals. As a result, a 12 o'clock direction in the rectangular ultrasound tomographic image is determined by which ultrasound transducers 29a the ultrasound observation apparatus 4 selects as the 12 o'clock direction to transmit the excitation signals.

The vector V which is normal to the ultrasound tomographic image, the vector $V_3$ pointing in the 3 o'clock direction and vector $V_{12}$ pointing in the 12 o'clock direction are defined with this type of operation. Note also that the ultrasound observation apparatus 4 generates ultrasound tomographic image data corresponding to a view in a direction −V which is the opposite direction to the normal direction vector V.

The radial scanning by the ultrasound transducer array 29, the generation of the ultrasound tomographic image data by the ultrasound observation apparatus 4 and the output of the generated ultrasound tomographic image data to the mixing circuit 61 are performed in real time. Hence, in the present embodiment, the ultrasound tomographic image of the internal portion of the test subject is generated as a real-time image.

(c) The following describes the operations of the present embodiment by following the flow of The third signals and data relating to position and the flow of data generated by processing the third signals and data relating to position.

The position and orientation calculating apparatus 5 excites the transmission coil (not shown) provided in the transmission antenna 6. As a result, the transmission antenna 6 generates an alternating magnetic field in the space therein. The coil portion wound around the direction of the vector V included in the image position and orientation detecting coil 31, the coil portion wound around the direction of the vector $V_3$ included in the image position and orientation detecting coil 31, each of the insertion shape detecting coils 32, the body cavity detecting coil 42 as the test subject detecting element, and the body surface detecting coils 7 each detect the alternating magnetic field generated by the transmission antenna 6. The detected alternating magnetic fields are converted to position electric signals which indicate the positions of each coil, and the position electric signals are outputted to the A/D units 9a, 9b and 9c.

The A/D units 9a, 9b and 9c amplify the position electric signals using amplifiers, convert the amplified analog data to digital data by sampling using the analog to digital converting circuit, and output the resulting digital data to the position and orientation calculating apparatus 5.

The position and orientation calculating apparatus 5 then calculates the positions of the image position and orientation detecting coil 31 and the directions of the perpendicular winding axes therein, that is, the vectors V and $V_3$ based on the digital data from the A/D unit 9a. Next, the position and orientation calculating apparatus 5 calculates the remaining perpendicular direction, which is the vector $V_{12}$ pointing towards 12 o'clock, by calculating the cross product of the vectors V and $V_3$ that correspond to the directions of the perpendicular winding axes. In this way, the position and orientation calculating apparatus 5 calculates the vectors V, $V_3$ and $V_{12}$ which point in the three perpendicular directions.

The position and orientation calculating apparatus 5 then calculates, based on the digital data from the A/D units 9a to 9c, the positions of each of the five insertion shape detecting coils 32, the positions of each of the body surface detecting coils 7, and the position of the body cavity detecting coil 42.

The position and orientation calculating apparatus 5 also makes a judgment about the detection states for the position and orientation of the image position and orientation detecting coil 31, the positions of each of the five insertion shape detecting coils 32 and the positions of each of the body surface detecting coils 7.

Specifically, the position and orientation calculating apparatus 5 issues a judgment of "undetectable" (the position of the coil cannot be detected) for any of the above-described coils for which a signal level of the inputted digital data is too low to allow the position to be detected (e.g. a level at which the signal is lost in environmental noise). Further, the position and orientation calculating apparatus 5 issues a judgment of "low accuracy" (i.e. the accuracy of the detection of coil position is low) for any of the above-described coils for which the calculation of position is performed at a signal/noise ratio of the inputted digital data which does not exceed a given level. A same judgment is issued when a distance between a calculated position and a position of the transmission antenna 6 is greater than or equal to a predetermined value. The position and orientation calculating apparatus issues a judgment of "normal" (i.e. the accuracy of the detection of coil position is high) for any of the above-described coils for which the position calculation is performed at a signal/noise ratio of the inputted digital data which exceeds the given level and the distance between the calculated position and the position of the transmission antenna 6 is less than the predetermined value.

Next, the position and orientation calculating apparatus 5 outputs the position and orientation of the image position and orientation detecting coil 31, the positions of each of the five insertion shape detecting coils 32, the positions of each of the four body surface detecting coils 7 and the position of the body cavity detecting coil 42 to the matching circuit 51 of the image processing apparatus 11 as the position and orientation data.

The position and orientation calculating apparatus 5 also outputs the detection state judgments for the position and orientation of the image position and orientation detecting coil 31, the positions of each of the five insertion shape detecting coils 32, and the positions of each of the body surface detecting coils 7 to the matching circuit 51 of the image processing apparatus 11 as detection state data.

The following describes the position and orientation data in detail.

In the present embodiment, an origin 0 is defined on the transmission antenna 6, and an orthogonal coordinate system 0-xyz and an orthonormal basis (i.e. the unit vectors pointing in the directions of the axes) i, j, and k are defined in the space in which the operator is actually testing the test subject 37, as shown in FIG. 7. The position of the image position and orientation detecting coil 31 is defined as 0".

The image position and orientation detecting coil 31 is fixed in proximity to the center of the ring of the ultrasound transducer array 29. Hence, the position 0" matches the center of the radial scan and the center of the ultrasound tomographic image.

Here, the position and orientation data are defined as follows.

The directional components of a position vector 00" of the position 0" of the image position and orientation detecting coil 31 in the orthogonal coordinate system 0-xyz are:

(x0, y0, z0)

The angular components of an Eulerian angle which indicates the orientation of the image position and orientation detecting coil 31 with respect to the orthogonal coordinate system 0-xyz are:

($\phi$, $\theta$, $\phi$)

The directional components of the position vectors of each of the insertion shape detecting coils 32 in the orthogonal coordinate system 0-xyz are:

(xi, yi, zi) where "i" is a natural number from 1 to 5.

The directional components of the position vectors of each of the four body surface detecting coils 7 in the orthogonal coordinate system 0-xyz are:

(xa, ya, za), (xb, yb, zb), (xc, yc, zc), (xd, yd, zd)

The directional components of the position vector of the body cavity detecting coil 42 in the orthogonal coordinate system 0-xyz are:

(xp, yp, zp)

Here, the Eulerian angle is an angle where, as a result of rotations made around the z-axis, the y-axis and for a second time the z-axis in the orthogonal coordinate system 0-xyz of FIG. 7, which are performed in the stated order, the directions of each axis area as described below.

After the rotations, $i = V_3$, $j = V_{12}$, and $k = V$.

Note that $\phi$ denotes the angle of first rotation around the z-axis, $\theta$ denotes the angle of rotation around the y-axis, and $\phi$ denotes the angle of second rotation around the z-axis.

Note also that the point "H" in FIG. 7 is the point at which a line normal to the xy-plane dropped from the position 0" intersects with the xy-plane. The Eulerian angle angular components ($\phi$, $\theta$, $\phi$) give the orientation of the image position and orientation detecting coil 31 which corresponds to the orientation of the ultrasound tomographic image data.

The matching circuit 51 calculates, from first, second, third and fourth data groups described below, a conversion equation for mapping the position and orientation expressed in the orthogonal coordinate system 0-xyz to a position and orientation in the voxel space expressed in the orthogonal coordinate system 0'-x'y'z'. The calculation method is described in a later section.

The position and orientation data described below for the first and second data groups change with body movement of the test subject 37. Thus, the conversion equation is newly generated when the test subject 37 moves. The calculation method used to newly generate the conversion equation in this way is also described in a later section.

The first data group is made up of the directional components (xa, ya, za), (xb, yb, zb), (xc, yc, zc), and (xd, yd, zd) of the position vectors, in the orthogonal coordinate system 0-xyz, of the body surface detecting coils 7 respectively attached to the xiphoid process, the left anterior superior iliac spine, the right anterior superior iliac spine, and the spinous process of vertebral body of the test subject 37, among the position and orientation data. FIG. 8 shows the body surface detecting coils 7 in a state of being attached in the above-described positions.

The second data group is made up of the directional components (xp, yp, zp) of the position vector of the body cavity detecting coil 42 in the orthogonal coordinate system 0-xyz, among the position and orientation data.

In FIG. 9, the body cavity contacting probe 8 which has the body cavity detecting coil 42 fixed at a tip thereof is shown as a thick broken line.

The third data group is made up of coordinates, in the orthogonal coordinate system 0'-x'y'z', of pixels in each of the xiphoid process, the left anterior superior iliac spine, the right anterior superior iliac spine and the spinous process of vertebral body. Each of above-described pixels may exist in any of the $1^{st}$ to $N^{th}$ reference image data and is the pixel which is nearest to the body surface in the respective anatomical portion. The pixels' coordinates are (xa', ya', za'), (xb', yb', zb'), (xc', yc', zc') and (xd', yd', zd'), respectively.

The pixels are specified in advance in any of the $1^{st}$ to $N^{th}$ reference image data by the operator. The specifying method is described in a later section.

In FIG. 9, the pixels are indicated by black circles ● and a white circle ○. The coordinates (xa', ya', za'), (xb', yb', zb'), (xc', yc', zc') and (xd', yd', zd') are read from the reference image storage portion 55 to the matching circuit 51 as the body surface characteristic point coordinates as shown in FIG. 4.

The fourth data group are the coordinates in the orthogonal coordinate system 0'-x'y'z' of the pixel corresponding to the duodenal papilla in any of the $1^{st}$ to $N^{th}$ reference image data.

The coordinates of the fourth data group are (xp", yp", zp") and are specified in advance in any of the $1^{st}$ to $N^{th}$ reference image data by the operator. The specifying method is described in a later section.

In FIG. 9, the pixel (of coordinates (xp", yp", zp") in the orthogonal coordinate system 0'-x'y'z') is denoted by "P". The coordinates (xp", yp", zp") are read from the reference image storage portion 55 to the matching circuit 51 as the body cavity characteristic point coordinates, as shown in FIG. 4.

Next, matching circuit 51 calculates new position and orientation data in the orthogonal coordinate system 0'-x'y'z' by mapping the position and orientation data calculated in the orthogonal coordinate system 0-xyz in accordance with the conversion equation described above.

Next, the matching circuit 51 outputs the new position and orientation data to the image indicator generating circuit 52 and the insertion shape generating circuit 53 as position and orientation mapped data, and outputs the above-described detection state data to the image indicator generating circuit 52, the insertion shape generating circuit 53 and the detection state image generating circuit 64.

The image indicator generating circuit 52 generates image indicator data based on the position and orientation mapped data and the detection state data, and outputs the generated image indicator data to the synthesizing circuit 58. Here, the position and orientation mapped data has a total of six degrees of freedom and is the mapped version of the position and orientation data made up of the directional components (x0, y0, z0) of the position vector 00" of the position 0" of the image position and orientation detecting coil 31 in the orthogonal coordinate system 0-xyz and the angular components ($\phi$, $\theta$, $\varphi$) of the Eulerian angle which indicates the orientation of the image position and orientation detecting coil 31 with respect to the orthogonal coordinate system 0-xyz.

The generation of the image indicator data is illustrated in FIGS. 10A to 10C. Specifically, FIGS. 10A to 10C each show image indicator data of the type shown in the lower part of each drawing being generated from the position and orientation mapped data in the upper part of each drawing.

The above-described image indicator data is image data in the orthogonal coordinate system 0'-x'y'z' superimposed with a parallelogram ultrasound tomographic image marker Mu, an arrow-like distal end direction marker Md and an arrow-like 6 o'clock direction marker Mt. The ultrasound tomographic image marker Mu, the distal end direction marker Md and the 6 o'clock direction marker Mt are each colored in accordance with detection state data of the image position and orientation detecting coil 31.

Specifically, when the detection state data of the image position and orientation detecting coil 31 indicates that detection is "normal", the image indicator generating circuit 52 allocates semi-transparent white to the ultrasound tomographic image marker Mu, blue to the distal end direction marker Md, and light green to the 6 o'clock direction marker Mt (, as shown in FIG. 10A, for example). Further, when the detection state data of the image position and orientation detecting coil 31 indicates that detection is of "low accuracy", the image indicator generating circuit 52 allocates semi-transparent yellow to the ultrasound tomographic image marker Mu, yellow to the distal end direction marker Md, and yellow to the 6 o'clock direction marker Mt (, as shown in FIG. 10B, for example). Further, when the detection state data of the image position and orientation detecting coil 31 indicates that the coil is "undetectable", the image indicator generating circuit 52 allocates semi-transparent red to the ultrasound tomographic image marker Mu, red to the distal end direction marker Md, and red to the 6 o'clock direction marker Mt (, as shown in FIG. 10C, for example).

The insertion shape generating circuit 53 generates insertion shape data based on the position and orientation mapped data and the detection state data (using interpolation and marker generating processing), and outputs the generated insertion shape data to the synthesizing circuit 58. Here, the position and orientation mapped data is the mapped version of the position and orientation data made up of the directional components (x0, y0, z0) of the position vector 00" for the position 0" of the image position and orientation detecting coil 31 and the directional components (xi, yi, zi) of the position vectors for the plurality of insertion shape detecting coils 32 in the orthogonal coordinate system 0-xyz.

The insertion shape data is image data in the orthogonal coordinate system 0'-x'y'z' where an string-like insertion shape marker Ms obtained by sequentially connecting and interpolating between the positions of the image position and orientation detecting coil 31 and each of the five insertion shape detecting coils 32 is superimposed onto coil position markers Mc indicating the position of each of the coils.

Here, to describe specific operations of the insertion shape generating circuit 53, an example is used in which the detection state data for the image position and orientation detecting coil 31 and the first, third, and fifth insertion shape detecting coils 32 from the distal end indicates that the detection is "normal", the detection state data for the second insertion shape detecting coil 32 from the distal end indicates that the coil is "undetectable", and the detection state data of the fourth insertion shape detecting coil 32 from the distal end indicates that the detection is of "low accuracy". This state is shown in FIG. 11A.

The data shown in the upper level of FIG. 11A, which is the position and orientation mapped data in the orthogonal coordinate system 0'-x'y'z' for the image position and orientation detecting coil 31 and the first, third, fourth and fifth insertion shape detecting coils 32 from the distal end is inputted to the insertion shape generating circuit 53.

When generating the insertion shape data, the insertion shape generating circuit 53 first reads scope data which has been stored in advance in the scope data storage portion 67.

Note that the scope data stored in advance in the scope data storage portion 67 includes values for a distance l1 from the image position and orientation detecting coil 31 to the insertion shape detecting coil 32 located at the distal most end, a distance l2 from the insertion shape detecting coil 32 located at the distal most end to the second insertion shape detecting coil 32, a distance l3 from the second insertion shape detecting coil 32 to the third insertion shape detecting coil 32, a distance l4 from the third insertion shape detecting coil 32 to the fourth insertion shape detecting coil 32, a distance l5 from the fourth insertion shape detecting coil 32 to the fifth insertion shape detecting coil 32, and a diameter "r" of the flexible portion 22 (and/or a diameter of the rigid portion 21). Note also that the distances l1 to l5 are the distances measured when the rigid portion 21 and the flexible portion 22 of the ultrasound endoscope 2 are in a straight-line state.

Next, the insertion shape generating circuit 53 generates, in the orthogonal coordinate system 0'-x'y'z', an insertion shape curve to join the image position and orientation detecting coil 31 and the insertion shape detecting coils which are not "undetectable" (i.e. the first, third, fourth and fifth insertion shape detecting coils 32 from the distal end) in order staring at the distal end.

The insertion shape generating circuit 53 then estimates the position of the insertion shape detecting coil 32 which was "undetectable" (i.e. the position of the second insertion shape detecting coil 32 from the distal end) based on the distances l2 and l3. Specifically, the insertion shape generating circuit 53 estimates that the second insertion shape detecting coil 32 from the distal end is positioned in a section between the first and third insertion shape detecting coils 32 from the distal end at a location that divides the section in a ratio of 12:13 in the insertion shape curve.

In the present embodiment, when there is an "undetectable" insertion shape detecting coil at a more proximal position than the most proximal coil of the insertion shape detecting coils which are not "undetectable", for example (though it is an example different from the one shown in FIG. 11A), the insertion shape generating circuit 53 does not perform an estimation of the position of the "undetectable" insertion shape detecting coil.

The insertion shape generating circuit 53 generates the insertion shape marker Ms based on the insertion shape curve and the diameter "r". The insertion shape generating circuit 53 generates the coil position markers Mc which indicate each coil position based on the mapped positions of each of the insertion shape detecting coils 32 so that the coil position markers Mc are superimposed on the insertion shape marker Ms. An example of the insertion shape data generated in this way is shown in the lower level of FIG. 11A.

Note that when generating the coil position markers Mc, the insertion shape generating circuit 53 allocates red to markers for coils which are "undetectable", yellow to markers for coils for which the detection is of "low accuracy", and black to markers for coils for which the detection is "normal".

The detection state image generating circuit 64, which is a detection state notification information generating portion generates a detection state image shown in FIG. 11B, for example, which can visually notify the operator as to the detection states for the positions of the image position and orientation detecting coil 31, the five insertion shape detecting coils 32 and the body surface detecting coils 7 based on the detection state data, and outputs corresponding detection state image data to the mixing circuit 61.

The above-described detection state image includes a marker 101 which indicates the detection state for the position of the image position and orientation detecting coil 31, markers 102a, 102b, 102c and 102d which indicate the detection states for the positions of each of the five insertion shape detecting coils 32, and markers 103a, 103b, 103c and 103d which indicate the detection state for the positions of each of the body surface detecting coils 7. Based on the detection state data inputted from the matching circuit 51, markers for coils which are "undetectable" are colored red, markers for coils for which the detection is of "low accuracy" are colored yellow, and markers for coils for which the detection is "normal" are colored green.

(d) The following describes operations of the present embodiment by following a flow of the fourth reference image data and data generated by processing the reference image data.

The operator acquires reference image data of the entire ventral portion of the test subject 37 using the X-ray 3-dimensional helical computer tomography system 15 and/or the 3-dimensional magnetic resonance imaging system 16 before performing observations using the ultrasound endoscope 2.

The operator instructs acquisition of the reference image data by pressing predetermined keys on the keyboard 13 or selecting from on-screen menus using a mouse 12. At this point, the operator further indicates the acquisition source for the reference image data. Based on the above-described instructions, the control circuit 63 instructs the communication circuit 54 to acquire the reference image data from the acquisition source.

For instance, when the acquisition source of the reference image data is the X-ray 3-dimensional helical computer tomography system 15, the communication circuit 54 acquires a plurality of 2-dimensional CT images from the network 17 as the reference image data, and stores the acquired 2-dimensional CT images in the reference image storage portion 55.

When performing imaging using the X-ray 3-dimensional helical computer tomography system 15, an operator injects a X-ray contrast medium into a blood vessel of the test subject 37 before imaging so that blood vessels such as the aorta and the superior mesenteric vein (i.e. the vascular system) and organs which have many blood vessels appear with high or medium brightness on the 2-dimensional CT images. By this method, it is easy to generate differences in brightness between blood vessels (and organs having many blood vessels) and surrounding tissue.

When the acquisition source of the reference image data is the 3-dimensional magnetic resonance imaging system 16, the communication circuit 54 acquires a plurality of 2-dimensional MRI images from the network 17 as the reference image data, and stores the acquired 2-dimensional MRI images in the reference image storage portion 55.

When performing imaging using the 3-dimensional magnetic resonance imaging system 16, an operator injects a magnetic contrast medium with a high sensitivity to nuclear magnetic resonance into a blood vessel of the test subject 37 before imaging so that blood vessels such as the aorta and the superior mesenteric vein and organs which have many blood vessels appear with high or medium brightness on the 2-dimensional MRI images. By this method, it is easy to generate differences in brightness between blood vessels (and organs having many blood vessels) and surrounding tissue.

Note that the operations are substantially the same whether the X-ray 3-dimensional helical computer tomography system 15 or the 3-dimensional magnetic resonance imaging system 16 is selected as the acquisition source. For this reason, the following only describes the operations for the case in which the X-ray 3-dimensional helical computer tomography system 15 is selected as the acquisition source, and the communication circuit 54 acquires the plurality of 2-dimensional CT images as the reference image data.

FIG. 5 shows an example of the reference image data stored in the reference image storage portion 55. As a result of the action of the X-ray contrast medium, blood vessels such as the aorta and the superior mesenteric vein show up with a high brightness, organs having many peripheral blood vessels such as the pancreas show up with medium brightness, and duodenum and the like show up with low brightness.

The interpolating circuit 56 reads all the reference image data (from the $1^{st}$ to $N^{th}$ images) from the reference image storage portion 55. Next, the interpolating circuit 56 embeds the read reference image data in the voxel space in the interpolating memory 56a.

Specifically, the interpolating circuit 56 outputs a brightness of each pixel in the reference image data to a voxel which has an address corresponding to the pixel. The interpolating circuit 56 embeds data into empty voxels by interpolating based on brightness values in the adjacent reference image data. In this way, all the voxels of the voxel space are filled with data (hereinafter referred to as voxel data) based on the reference image data.

The 3-dimensional body image generating circuit 57 extracts the voxels having high brightness values (mainly blood vessels) and the voxels having medium brightness values (mainly organs having many peripheral blood vessels, such as the pancreas) from the interpolating circuit 56 separately according to brightness value ranges, and assigns a different color to each brightness value range.

Next, the 3-dimensional body image generating circuit 57 embeds the extracted voxels in the voxel space of the synthesizing memory 58a of the synthesizing circuit 58 as 3-dimensional body image data. During this process, the 3-dimensional body image generating circuit 57 embeds the extracted voxels so that the addresses of corresponding voxels are the same in the voxel space in the interpolating memory 56*a* and in the voxel space in the synthesizing memory 58*a*.

FIG. 12 shows an example of 3-dimensional body image data. The 3-dimensional body image data of the example shown in FIG. 12 is the result of extracting the aorta and the superior mesenteric vein, which are blood vessels having high brightness, and the pancreas which is an organ having medium brightness. More specifically, in the 3-dimensional body image data of the example shown in FIG. 12 the blood vessels are colored red, and the pancreas is colored green. The view is from the ventral side with the cranial side of the test subject 37 on the right-hand side and the caudal side of the test subject 37 on the left-hand side.

Thus the 3-dimensional body image generating circuit 57 functions as an extracting portion for extracting organs, blood vessels, and the like. Note that the extracting portion may be provided with a 3-dimensional guide image generating circuit A and a 3-dimensional guide image generating circuit B. When generating the 3-dimensional guide image, the extracting portion may be configured to allow selection of the organs and blood vessels using the 3-dimensional guide image generating circuit A and the 3-dimensional guide image generating circuit B.

The synthesizing circuit 58 then embeds the image indicator data and the insertion shape data in the voxel space of the synthesizing memory 58*a*. This state is shown in FIG. 13.

It is to be noted that the 3-dimensional body image data existing in the voxel space is simplified in FIG. 13 for clarity (see FIG. 14 and other drawings for non-simplified versions of the 3-dimensional body image data). Thus, the synthesizing circuit 58 embeds the 3-dimensional body image data, the image indicator data, and the insertion shape data of the same voxel space in the same synthesizing memory to synthesize combined data (hereinafter referred to as synthesized 3-dimensional data).

After reading the synthesized 3-dimensional data from the synthesizing circuit 58, the rotation converting circuit 59 performs rotation processing on the synthesized 3-dimensional data in accordance with the rotation instruction signal from the control circuit 63.

The 3-dimensional guide image generating circuit A performs rendering processing for hidden surface removal and shading on the synthesized 3-dimensional data to generate image data (hereinafter referred to as 3-dimensional guide image data) which can be displayed on a screen.

Note that the default orientation of the 3-dimensional guide image data is a view from the ventral side of the body. Hence, the 3-dimensional guide image generating circuit A generates the 3-dimensional guide image data as a view from the ventral side of the test subject 37. Note, however, that the 3-dimensional guide image generating circuit A is not limited to generating image data which is a view from the ventral side of the body as the default orientation of the 3-dimensional guide image data, and may, for instance, generate image data for a view from the dorsal side or data which is a view from another direction.

The 3-dimensional guide image generating circuit A outputs the 3-dimensional guide image data showing the test subject 37 from the ventral side to the mixing circuit 61. The 3-dimensional guide image data is shown in FIG. 14. In FIG. 14, the cranial side of the test subject 37 is on the right-hand side and the caudal side of the test subject 37 is on the left-hand side.

In the 3-dimensional guide image data of FIG. 14, the ultrasound tomographic image marker Mu is semi-transparent to allow the 6 o'clock direction marker Mt and the distal end direction marker Md of the image indicator data, and the insertion shape marker Ms and the coil position markers Mc of the insertion shape data to be seen through the ultrasound tomographic image marker Mu.

In the 3-dimensional guide image data of FIG. 14, the ultrasound tomographic image marker Mu is non-transparent with respect to the other organs so that portions of the organs behind the ultrasound tomographic image marker Mu are not visible. Note also that the markers in FIG. 14 which are located behind and overlapped by the ultrasound tomographic image marker Mu are shown using broken lines.

The 3-dimensional guide image generating circuit B performs rendering processing for hidden surface removal and shading on the synthesized 3-dimensional data which has undergone rotation processing to generate 3-dimensional guide image data which can be displayed on the screen.

In the present embodiment, as an example, the instruction based on input from the mouse 12 or the keyboard 13 is for a view from the caudal side of the test subject 37, which is a view in which the 3-dimensional guide image data has been rotated by 90 degrees according to a rotation instruction signal from the control circuit 63.

Hence, the 3-dimensional guide image generating circuit B generates the 3-dimensional guide image data showing the test subject 37 from the caudal side.

The 3-dimensional guide image generating circuit B outputs the 3-dimensional guide image data showing the test subject 37 from the caudal side to the mixing circuit 61. The 3-dimensional guide image data is shown in FIG. 15. In FIG. 15, the right side of the test subject 37 is on the right-hand side and the left side of the test subject 37 is on the left-hand side.

In the 3-dimensional guide image data of FIG. 15, the ultrasound tomographic image marker Mu is semi-transparent to allow The 6 o'clock direction marker Mt and the distal end direction marker Md of the image indicator data, and the insertion shape marker Ms and the coil position markers Mc of the insertion shape data to be seen through the ultrasound tomographic image marker Mu.

Further, in the 3-dimensional guide image data of FIG. 15, the ultrasound tomographic image marker Mu is non-transparent with respect to the other organs so that portions of the organs behind the ultrasound tomographic image marker Mu are not visible. Note also that the markers in FIG. 15 which are located behind and overlapped by the ultrasound tomographic image marker Mu are shown using broken lines.

Further, in the display of the ultrasound tomographic image marker Mu in FIG. 15, the normal of the ultrasound tomographic image marker Mu does not match the observation direction (i.e. the normal to the screen of the display apparatus 14). This type of display is referred to hereinafter as non-squarely-face display.

(e) The following describes operations of the present embodiment by following the flow of the fifth signals and data relating to the final display screen which is synthesized from the ultrasound tomographic image data and the 3-dimensional guide image data.

The mixing circuit 61 shown in FIG. 4 generates mixed data for display from the ultrasound tomographic image data from the ultrasound observation apparatus 4, the 3-dimensional guide image data showing the test subject 37 from the ventral side from the 3-dimensional guide image generating circuit A, 3-dimensional guide image data showing the test subject 37 from the caudal side from the 3-dimensional guide image generating circuit B, and the detection state image from the detection state image generating circuit 64.

The display circuit 62 converts the mixed data to an analog video signal and outputs the analog video signal to the display apparatus 14.

Based on the analog video signal, the display apparatus 14 displays, as shown in FIG. 16 for example, the ultrasound tomographic image, the 3-dimensional guide image showing the test subject 37 from the caudal side, the 3-dimensional guide image showing the test subject 37 from the ventral side, and the detection state image, side by side, in a manner which allows comparison.

As shown in FIG. 16, the display apparatus 14 displays the organs appearing in the 3-dimensional guide image in different colors by assigning colors depending on the brightness values in the reference image data.

In the display example of FIG. 16, the pancreas is displayed in green, and the aorta and superior mesenteric vein are displayed in red. Note also that the markers in FIG. 16 which are located behind and overlapped by the ultrasound tomographic image marker Mu are shown using broken lines.

Moreover, as shown by the outlined arrows in FIG. 16, the two 3-dimensional guide images move as the radial scanning plane moves.

(f) Sixthly, the following describes operations of the present embodiment by following the flow of signals and data relating to control.

The matching circuit 51, the image indicator generating circuit 52, the insertion shape generating circuit 53, the communication circuit 54, the reference image storage portion 55, the interpolating circuit 56, the 3-dimensional body image generating circuit 57, the synthesizing circuit 58, the rotation converting circuit 59, the 3-dimensional guide image generating circuit A, the 3-dimensional guide image generating circuit B, the mixing circuit 61, the display circuit 62, the detection state image generating circuit 64 and the scope data storage portion 67 of the image processing apparatus 11 shown in FIG. 4 are all controlled by instructions from the control circuit 63. Note that details of the control are described in a later section.

The following describes the overall operations of the image processing apparatus 11, the keyboard 13, the mouse 12, and the display apparatus 14 of the present embodiment when used by the operator. FIG. 17 is a flowchart showing the overall operations. The processing of steps S1 to S4 in FIG. 17 is executed in numerical order.

First, step S1 is processing to specify body surface characteristic points and a body cavity characteristic point in the reference image data. In other words, for the reference image data, processing to specify characteristic points on the surface of the body and in the body cavity is performed in step S1 of FIG. 17.

Next, in step S2, the operator fixes the body surface detecting coils 7 to the test subject 37. The operator has the test subject 37 lie on their left side in what is known as the left lateral position. The operator palpates the test subject 37 and fixes the body surface detecting coils 7 on the body surface in the four positions nearest to the xiphoid process, the left anterior superior iliac spine, the right anterior superior iliac spine, and the spinous process of vertebral body, which are the four body surface characteristic points.

Step S3 is correction value calculation processing.

In step S3, the image processing apparatus 11 acquires position and orientation data of the body cavity characteristic point, calculates a conversion equation for mapping the position and orientation data expressed in the orthogonal coordinate system 0-xyz to the position and orientation mapped data in the voxel space which is expressed in the orthogonal coordinate system 0'-x'y'z'. The image processing apparatus 11 then performs processing to calculate correction values for the conversion equation based on the position and orientation data of the body cavity characteristic point.

Next, in step S4, the image processing apparatus 11 performs processing to generate and display the ultrasound tomographic image and the 3-dimensional guide image. In other words, step S4 is processing for generating the ultrasound tomographic image and the 3-dimensional guide image and displaying the generated images.

The following describes in detail the processing of step S1 of FIG. 17 which is the processing to specify the body surface characteristic points and the body cavity characteristic point in the reference image data.

FIG. 18 is a flowchart showing the detailed processing of step S1 from FIG. 17 for specifying the body surface characteristic points and the body cavity characteristic point in the reference image data.

First, in step S1-1, the operator presses the display switching key 13a. In response, the control circuit 63 issues an instruction to the display circuit 62. The switch 62a of the display circuit 62 switches to the input terminal α as a result of the instruction from the control circuit 63.

Next, in step S1-2, the operator uses the mouse 12 or the keyboard 13 to specify any of the $1^{st}$ to $N^{th}$ images in the reference image data.

Next, in step S1-3, the control circuit 63 causes the display circuit 62 to read the specified reference image data from among the $1^{st}$ to $N^{th}$ reference image data stored in the reference image storage portion 55.

The display circuit 62 converts the reference image data from the reference image storage portion 55 to an analog video signal, and outputs the reference image data to the display apparatus 14. As a result, the reference image data specified by the operator is displayed on the display apparatus 14.

Next, in step S1-4, the operator specifies the body surface characteristic points on the reference image data using the mouse 12 or the keyboard 13. Specifically, the operator does the following.

The operator checks that at least one of the xiphoid process, the left anterior superior iliac spine, the right anterior superior iliac spine, and the spinous process of vertebral body, which correspond to the four body surface characteristic points of the test subject 37, appears in the reference image data displayed on the display apparatus 14. If none of these anatomical points appear, the image processing apparatus 11 returns to step S1-2 and has the operator specify different reference image data. The operator then continues to select reference image data until reference image data containing at least one of the above-described four body surface characteristic points is selected.

The operator specifies pixels corresponding to the points on the body surface in the displayed reference data that are nearest to the xiphoid process, the left anterior superior iliac spine, the right anterior superior iliac spine and the spinous process of vertebral body which are the four points on the body surface of the test subject 37, using the mouse 12 or the keyboard 13.

In FIGS. 8 and 9, the specified points are represented by black circles ● and a white circle ○. In the present embodiment, to enable a clear description, it is assumed that the xiphoid process (○) appears in the $n1^{th}$ ($1 \leq n1 \leq N$) reference image data and the left anterior superior iliac spine, the right anterior superior iliac spine and the spinous process of vertebral body (all ●) appear in the $n2^{th}$ ($1 \leq n2 \leq N$) reference image data.

Note that in FIG. 8 and FIG. 9, the position of the xiphoid process in the n2$^{th}$ reference image data is marked by a ○ to enable a clear description.

Next, in step S1-5, the operator uses the mouse 12 or the keyboard 13 to specify a body cavity characteristic point P"'. In the present embodiment, as an example, the duodenal papilla (an opening to the common bile duct in the duodenum) is specified as the body cavity characteristic point p"'. Specifically, the operator does the following.

The operator uses the mouse 12 or the keyboard 13 to specify any of the 1$^{st}$ to N$^{th}$ reference image data.

The control circuit 63 controls the display circuit 62 to read the specified reference image data from among the 1$^{st}$ to N$^{th}$ reference image data stored in the reference image storage portion 55 via a signal wire not shown in the drawings.

The display circuit 62 outputs the read reference image data to the display apparatus 14. As a result the reference image specified by the operator is displayed on the display apparatus 14. If the duodenal papilla, which is the body cavity characteristic point of the test subject 37, does not appear in the displayed reference image data, the operator specifies different reference image data. Thus, the reading and displaying of the different reference data is repeated until reference image data in which the duodenal papilla appears is displayed.

The operator uses the mouse 12 or the keyboard 13 to specify the pixel corresponding to the duodenal papilla, which is the body cavity characteristic point, of the test subject 37 in the displayed reference image data. The point specified in this way is denoted by P"' in FIG. 9. Note that, in the present embodiment, it is assumed for convenience that the duodenal papilla P"' appears in the n2$^{th}$ (1≦n2≦N) reference image data.

Next, in step S1-6, the control circuit 63 calculates, based on the addresses in the reference image data, coordinates in the voxel space-spanning orthogonal coordinate system 0'-x'y'z' for the pixels corresponding to the body surface characteristic points specified in steps S1-4 and the pixel corresponding to the body cavity characteristic point P"' specified in steps S1-5, and outputs the calculated coordinates to the matching circuit 51.

Here, the calculated values of the coordinates in the orthogonal coordinate system 0'-x'y'z' of the pixels corresponding to the body surface characteristic points specified in step S1-4 are set as (xa', ya', za'), (xb', yb', zb'), (xc', yc', zc'), and (xd', yd', zd'). Further, the calculated values of the coordinates in the orthogonal coordinate system 0'-x'y'z' of the pixel corresponding to the body cavity characteristic point specified in the step S1-5 are set as (xp"', yp"', zp"').

The matching circuit 51 stores the above-described coordinates. When step S1-6 has been completed, the processing proceeds to step S2 of FIG. 17. Further, after completing the processing of step S2, the processing proceeds to the correction value calculation processing of step S3 in FIG. 17.

FIG. 19 is a flowchart showing the details of correction value calculation processing in step S3 of FIG. 17. As described above, step S3 of FIG. 17 is processing to acquire position and orientation data of the body cavity characteristic point, calculate the conversion equation for mapping the position and orientation data expressed in the orthogonal coordinate system 0-xyz to the position and orientation mapped data in the voxel space which is expressed in the orthogonal coordinate system 0'-x'y'z', and calculate correction values of the conversion equation based on the position and orientation data of the body cavity characteristic point.

First in step S3-1, the operator presses The display switching key 13β. As a result the control circuit 63 issues an instruction to the display circuit 62. The switch 62a of the display circuit 62 switches to the input terminal β as a result of the instruction from the control circuit 63.

Next, in step S3-2, the display circuit 62 converts the optical image data from the optical observation apparatus 3 to an analog video signal and outputs the optical image to the display apparatus 14. As a result, the optical image is displayed on the display apparatus 14.

Next, in step S3-3, the operator inserts the rigid portion 21 and the flexible portion 22 of the ultrasound endoscope 2 into the body cavity of the test subject 37.

Next, in step S3-4, the operator searches for the body cavity characteristic point by moving the rigid portion 21 while observing the optical image. Upon finding the body cavity characteristic point, the operator moves the rigid portion 21 to a position near to the body cavity characteristic point.

Next, in step S3-5, the operator inserts the body cavity contacting probe 8 into the forceps opening 44 and causes the body cavity contacting probe 8 to protrude from the protrusion opening 45 while observing the optical image. The operator then causes the tip of the body cavity contacting probe 8 to contact the body cavity characteristic point which is in the field of view of the optical image. This state is shown in FIG. 20.

FIG. 20 shows the optical image displayed on the display screen of the display apparatus 14. The optical image of FIG. 20 includes the duodenal papilla P as an example of the body cavity characteristic point, and the body cavity contacting probe 8.

In step S3-6, the operator presses the body cavity characteristic point specifying key 65.

Note here that, in the present embodiment, the following processing is performed in the control circuit 63 and the like in parallel with step S3-6.

The control circuit 63 reads the detection state data of the four body surface detecting coils 7 from the position and orientation calculating apparatus 5 via signal lines not shown in the drawings.

When one or more of the four body surface detecting coils 7 has been judged to be "undetectable" based on the detection state data of the body surface detecting coils 7, the control circuit 63 performs processing to generate a character string or the like to give the operator notification to the effect that the body cavity characteristic point specifying key 65 should be pressed a second time, and cause the display apparatus 14 to display the character string. The control circuit 63 then enters waiting state of step S3-6 in which the character string is displayed on the display apparatus 14 until the body cavity characteristic point specifying key 65 is pressed the second time.

When none of the four body surface detecting coils 7 has been judged to be "undetectable" based on the detection state data of the body surface detecting coils 7, and the detection has been judged to be of "low accuracy" for one or more coils based on the detection state data, the control circuit 63 performs processing to generate a character string or the like to cause the operator to select whether to proceed with the processing, and cause the display apparatus 14 to display the character string. When an instruction to the effect that processing should be continued is selected using the mouse 12 or the keyboard 13, the control circuit 63 proceeds to the processing of step S3-7. When, on the other hand, an instruction to the effect that processing should be stopped is selected using the mouse 12 or the keyboard 13, the control circuit 63 performs processing to generate a character string or the like to give the operator notification to the effect that the body cavity characteristic point specifying key 65 should be pressed a second time, and cause the display apparatus 14 to display the character string. The control circuit 63 then enters the waiting state of step S3-6 in which the character string is displayed on the display apparatus 14 until the body cavity characteristic point specifying key 65 is pressed a second time.

Note that when there are no coils for which a judgment of either "undetectable" or "low accuracy" has been made, the control circuit 63 proceeds directly to step S3-7.

In step S3-7, the control circuit 63 issues an instruction to the matching circuit 51. On receiving the instruction from the control circuit 63, the matching circuit 51 reads the position and orientation data from the position and orientation calculating apparatus 5 and stores the read position and orientation data. As described above, the position and orientation data includes two types of data made up of the directional components of the position vectors corresponding to the four body surface detecting coils 7 in the orthogonal coordinate system 0-xyz and the directional components of the position vector of the body cavity detecting coil 42 in the orthogonal coordinate system 0-xyz. In other words, the two types of data are the coordinates of the four body surface characteristic points in the orthogonal coordinate system 0-xyz, which are (xa, ya, za), (xb, yb, zb), (xc, yc, zc), and (xd, yd, zd), and the coordinates of the body cavity characteristic point, which is (xp, yp, zp), in the orthogonal coordinate system 0-xyz. Note that the two types of data are acquired from a total of five coils made up of the four body surface detecting coils 7 and the single body cavity detecting coil 42.

In step S3-8, the matching circuit 51 generates a first conversion equation which expresses a first mapping from the coordinates of the body surface characteristic points. Specifically, the matching circuit 51 does the following.

First, the matching circuit 51 stores the following content.

(1) The coordinates, in the orthogonal coordinate system 0'-x'y'z' of the voxel space, of the pixels corresponding to the body surface characteristic points specified in step S1:

(xa', ya', za'), (xb', yb', zb'), (xc', yc', zc'), (xd', yd', zd')

(2) The coordinates, in the orthogonal coordinate system 0'-x'y'z' of the voxel space, of the pixel corresponding to the body cavity characteristic point specified in step S1:

(xp'', yp'', zp'')

(3) The coordinates in the orthogonal coordinate system 0-xyz of the body surface characteristic points acquired in step S3-7:

(xa, ya, za), (xb, yb, zb), (xc, yc, zc), (xd, yd, zd)

(4) The coordinates in the orthogonal coordinate system 0-xyz of the body cavity characteristic point acquired in step S3-7:

(xp, yp, zp)

The matching circuit 51 generates the first conversion equation expressing a first mapping for converting any point in the orthogonal coordinate system 0-xyz to a point in the orthogonal coordinate system 0'-x'y'z' of the voxel space, using the coordinates (3) (xa, ya, za), (xb, yb, zb), (xc, yc, zc), and (xd, yd, zd) and the coordinates (1) (xa', ya', za'), (xb', yb', zb'), (xc', yc', zc'), and (xd', yd', zd'). The first mapping and first conversion equation are determined in the following manner.

The matching circuit 51 uses the xiphoid process, the left anterior superior iliac spine, the right anterior superior iliac spine, and the spinous process of vertebral body which are the body surface characteristic points to virtually set up an un-orthogonal coordinate system made up of three basis vectors which point from the xiphoid process towards the other points, both on the test subject 37 and in the voxel space (in FIG. 8 the reference image data is shown but the voxel space referred to here is the data space which includes the data obtained by interpolating between the reference image data) as shown in FIG. 8.

The first mapping is a mapping from the test subject 37 to the voxel space so that "coordinates, expressed using the un-orthogonal reference frame on the test subject 37, of a given point in the orthogonal coordinate system 0-xyz" are the same as "coordinates, expressed using the un-orthogonal reference frame in the voxel space, of a point in the orthogonal coordinate system 0'-x'y'z' resulting from mapping the given point".

Further, the first conversion equation is a method for converting "coordinates of a given point in the orthogonal coordinate system 0-xyz" to "coordinates in the orthogonal coordinate system 0'-x'y'z' of the given point after the first mapping to voxel space".

For instance, the position of the image position and orientation detecting coil 31, which is the center 0'' of the radial scan and the ultrasound tomographic image, may be mapped to a point Q' under the first mapping as shown in FIG. 8.

Let it be assumed that the coordinates of the point Q' in the orthogonal coordinate system 0'-x'y'z' are (x0', y0', z0'). When the first conversion equation is applied, the coordinates (x0, y0, z0) of the point 0'' in the orthogonal coordinate system 0-xyz are then converted to the coordinates (x0', y0', z0') of the point Q' in the orthogonal coordinate system 0'-x'y'z'.

Next, in the step S3-9, the matching circuit 51 maps the body cavity characteristic point P to the voxel space point P' using the first conversion equation as shown in FIG. 9. The coordinates of the body cavity characteristic point P in the orthogonal coordinate system 0-xyz are (xp, yp, zp). Here, the coordinates in the orthogonal coordinate system 0'-x'y'z' of the point P' which result from the first mapping are defined as (xp', yp', zp').

Next, in step S3-10, the matching circuit 51 calculates, in the manner described below, a vector P'P''' from the coordinates (xp', yp', zp') of the point P' in the voxel-space orthogonal coordinate system 0'-x'y'z' and the coordinates (xp'', yp'', zp'') of the point P''' in the voxel-space orthogonal coordinate system 0'-x'y'z' which corresponds to the body cavity characteristic point specified in step S1.

$$P'P'''=(xp'',yp'',zp'')-(xp',yp',zp')=(xp''-xp',yp''-yp',zp''-zp')$$

Next, in step S3-11, the matching circuit 51 stores the vector P'P'''. The vector P'P''' acts as correction values for correcting the first conversion equation and generating a second conversion equation. When step S3-11 has been completed, the processing proceeds to step S4 of FIG. 17.

The following describes the processing of step S4 of FIG. 17 for generating and displaying the ultrasound tomographic image and the 3-dimensional guide image. FIG. 21 is a low chart showing details of the processing in step S4 of FIG. 17 for generating and displaying the actual ultrasound tomographic image of the test subject 37 and the 3-dimensional guide image of the subject.

Firstly, in step S4-1, the operator presses the display switching key 13γ. The control circuit 63 then issues an instruction to the display circuit 62. The switch 62a of the display circuit 62 switches to the input terminal γ on receiving the instruction from the control circuit 63.

Next, in step S4-2, the operator presses the scan controlling key 66.

Next, in step S4-3, the control circuit 63 outputs the scan controlling signal to the ultrasound observation apparatus 4. As a result, the ultrasound transducer array 29 begins the radial scan.

Next, in step S4-4, the control circuit 63 issues an instruction to the mixing circuit 61. Based on the instruction, the mixing circuit 61 sequentially acquires ultrasound tomographic image data inputted based on the radial scan from the ultrasound observation apparatus 4.

Next, in step S4-5, the control circuit 63 issues an instruction to the matching circuit 51. Based on the instruction from the control circuit 63, the matching circuit 51 acquires the position and orientation data and the detection state data from the position and orientation calculating apparatus 5, and stores the acquired data. Note that the acquisition operation is performed instantaneously. Thus, the matching circuit 51 acquires the position and orientation data which includes the data described below and the detection state data, at the instant of acquisition of the ultrasound tomographic image data by the mixing circuit 61 in the step S4-4.

More specifically, when one or more of the five coils composed of the image position and orientation detecting coil 31 and the four body surface detecting coils 7 have been judged to be "undetectable", the matching circuit 51 acquires the latest position and orientation data at the time the detection for the one or more coils was last judged to be "low accuracy" or "normal".

The position of the image position and orientation detecting coil 31 in the orthogonal coordinate system 0-xyz (i.e. the directional components of the position vector 00" of the center 0" of the radial scan and the ultrasound tomographic image) is:

(x0, y0, z0)

The orientation of the image position and orientation detecting coil 31 in the orthogonal coordinate system 0-xyz (i.e. the angular components of the Eulerian angle indicating the orientation of the ultrasound tomographic image) is:

($\phi$, $\theta$, $\phi$)

The directional components of the position vectors of each of the plurality of insertion shape detecting coils 32 in the orthogonal coordinate system 0-xyz are: (xi, yi, zi) where "i" is a natural number from 1 to 5.

The directional components of the position vectors of the four body surface detecting coils 7 in the orthogonal coordinate system 0-xyz are:

(xa, ya, za), (xb, yb, zb), (xc, yc, zc), (xd, yd, zd)

Next, in step S4-6, the matching circuit 51 uses, from among the position and orientation data acquired in step S4-5, the directional components (xa, ya, za), (xb, yb, zb), (xc, yc, zc) and (xd, yd, zd) of the position vectors of the four body surface detecting coils 7 in the orthogonal coordinate system 0-xyz to update the first conversion equation stored in step S3.

Next, the matching circuit 51 newly generates a second conversion equation which expresses the second mapping by combining a parallel translation by the vector P'P" stored in step S3 with the updated first conversion equation.

Also, the matching circuit 51 combines the first conversion equation with the parallel translation by the vector P'P" to generate the second conversion equation which expresses the second mapping. The concept behind of the second mapping is as follows:

second mapping=first mapping+parallel translation by the vector P'P".

The parallel translation by the vector P'P" has a correcting effect which is described below. The vector P'P" works as correction values.

As mentioned above, the first mapping is a mapping from the test subject 37 to the voxel space so that "coordinates, expressed using the un-orthogonal reference frame on the test subject 37, of a given point in the orthogonal coordinate system 0-xyz" are the same as "coordinates, expressed using the un-orthogonal reference frame in the voxel space, of a point in the orthogonal coordinate system 0'-x'y'z' resulting from mapping the given point".

Ideally, the mapped point P' resulting from the mapping of the body cavity characteristic point P to the voxel space would match the point P'" corresponding to the body cavity characteristic point specified in step S1. However, in practice it is difficult to make the two points match.

This difficulty is a consequence of the fact that a "spatial positional relationship between the given point in the orthogonal coordinate system 0-xyz and the un-orthogonal reference frame on the test subject 37" does not, for a variety of reasons, perfectly match the "spatial positional relationship between the point, in the orthogonal coordinate system 0'-x'y'z', that anatomically corresponds to the given point and un-orthogonal reference frame in the voxel space".

In the present embodiment, for instance, the first mapping and the first conversion equation were found using coordinates of the body surface characteristic points on the pelvis, but the duodenal papilla P that is the body cavity characteristic point may not always maintain the same positional relationship with the body surface characteristic points on the pelvis.

One of the main causes for this phenomenon is the difference between body position during the test using the X-ray 3-dimensional helical computer tomography system 15 or the 3-dimensional magnetic resonance imaging system 16 and body position during the test using the ultrasound endoscope 2. Specifically, the test subject 37 generally assumes the supine position during tests using the X-ray 3-dimensional helical CT system 15 and the 3-dimensional MRI system 16 while assuming the left lateral position during tests using the ultrasound endoscope 2, and the difference in the body positions means that the organs within the test subject 37 are displaced differently by gravity.

However, by combining the parallel translation by the vector P'P", which forms correction values, with the first mapping to form a second mapping, the mapped point of the body cavity characteristic point P is matched to the point P'" which is the body cavity characteristic point in the voxel space. It is then possible, by applying the second mapping to the other points of the test subject 37, such as the center 0" of the ultrasound tomographic image, to achieve a higher degree of matching between anatomical positions.

Next, in step S4-7, the matching circuit 51 converts, from among the position and orientation data acquired in step S4-5, the directional components (x0, y0, z0) of the position vector 00" of the center 0" of the ultrasound tomographic image in the orthogonal coordinate system 0-xyz, the angular components ($\phi$, $\theta$, $\phi$) of the Eulerian angle which indicates the orientation of the image position and orientation detecting coil 31 in the orthogonal coordinate system 0-xyz, and the directional components (xi, yi, zi) (where i is a natural number from 1 to 5) of the position vectors of the plurality of insertion shape detecting coils 32 in the orthogonal coordinate system 0-xyz to position and orientation mapped data using the newly generated second conversion equation.

As shown in FIG. 8, the center 0" of the ultrasound tomographic image is mapped to the point Q' in the voxel space using the first conversion equation. Then, in the same step, the center 0" of the ultrasound tomographic image is mapped to the point Q" in the voxel space using the newly generated second conversion equation, as shown in FIG. 9. Note that the vector Q'Q" which is the difference between Q' and Q" matches the amount of correction by the parallel translation in the second mapping, and is therefore the same as the vector P'P". In other words, the follow equation holds true.

$$Q'Q''=P'P''$$

Next, in the step S4-8, the image indicator data is generated by the image indicator generating circuit 52, the insertion shape data is generated by the insertion shape generating circuit 53, and the detection state image data is generated by the detection state image generating circuit 64.

The synthesizing circuit 58 then synthesizes the 3-dimensional body image data, the image indicator data and the insertion shape data to generate the synthesized 3-dimensional data.

The rotating conversion circuit 59 performs rotation processing on the synthesized 3-dimensional data.

The 3-dimensional guide image generating circuit A and the 3-dimensional guide image generating circuit B each generate 3-dimensional guide image data.

Note that the processing performed by the 3-dimensional guide image generating circuit A and the 3-dimensional guide image generating circuit B is the same as the above-described processing.

Next, in step S4-9, the mixing circuit 61 generates mixed data for display by combining the ultrasound tomographic image data, the 3-dimensional guide image data, and the detection state image data.

The display circuit 62 converts the mixed data to an analog video signal.

Based on the analog video signal, the display apparatus 14 displays the ultrasound tomographic image, the 3-dimensional guide image showing the test subject 37 from the ventral side, the 3-dimensional guide image showing the test subject 37 from the caudal side, and the detection state image adjacent to one another, in the manner shown in FIG. 16 for instance.

Note that the processing to obtain the images is that described in an earlier section.

Next, in step S4-10, the control circuit 63 checks whether the operator has pressed the scan controlling key 66 a second time between step S4-4 and S4-9.

When the scan controlling key 66 has been pressed a second time by the operator, the control circuit 63 ends the processing and outputs to the ultrasound observation apparatus 4 a scan controlling signal to instruct the radial scan to stop. On receiving the controlling signal, the ultrasound transducer array 29 ends the radial scan. When, on the other hand, the scan controlling key 66 has not been pressed a second time by the operator, the processing from step S4-4 to step S4-9 is performed a second time.

Repetition of the processing from step S4-4 to step S4-9 in this way causes the ultrasound observation apparatus 4 to generate an ultrasound tomographic image data based on the repeated radial scans by the ultrasound transducer array 29. Moreover, every time the ultrasound tomographic image data is inputted to the mixing circuit 61 from the ultrasound observation apparatus 4, two new 3-dimensional guide images are generated, and the ultrasound tomographic image and the 3-dimensional guide images are updated in real time and displayed on the display screen of the display apparatus 14.

Thus, as shown in FIG. 16, as the radial scanning plane is moved by the operator moving the flexible portion 22 and the rigid portion 21 by hand, the ultrasound tomographic image marker Mu, the distal end direction marker Md and the 6 o'clock direction marker Mt of the image indicator data, and the insertion shape marker Ms and the coil position marker Mc of the insertion shape data move or change shape on the 3-dimensional body image data. At the same time, the colors of the markers of the detection state image and the colors of the markers of the 3-dimensional guide image change according to detection states of the coils.

Note that the body cavity probe apparatus 1 of the present embodiment is not limited to performing processing to change the color of the coil position markers Mc themselves according to the detection states, and may, for instance, perform processing to change the color of the insertion shape maker Ms at the positions near the coil position markers Mc.

As described above, the body cavity probe apparatus 1 of the present embodiment has a configuration which allows visual notification of the detection state information of the coils provided to acquire information relating to the position and/or orientation of medical images by changing the colors of markers. The detection state information is information used when guide image is generated. Hence, the body cavity probe apparatus 1 of the present embodiment is capable of notifying an operator of information required to judge the reliability of information relating to the anatomical position and/or orientation of the acquired medical images to prevent misinterpretation of the position and orientation information by the operator.

Moreover, as described above, the body cavity probe apparatus 1 of the present invention is able to make use of markers in the detection state image as well as the markers in the guide image to provide visual notification of the detection states of the coils provided to acquire information relating to the position and/or orientation of the medical images. Thus, the body cavity probe apparatus 1 of the present embodiment allows detection states of the coils to be checked in the detection state image under conditions in which the coils provided to acquire information relating to the position and/or orientation of the medical image are hidden behind organs or the like in the guide image.

Further, as described above, the body cavity probe apparatus 1 of the present embodiment is configured to enable the insertion shape marker and the coil position markers to be generated even when there are coils, among the plurality of coils included in the ultrasound endoscope, for which the information relating to the position and/or orientation cannot be acquired. When such coils exist, the insertion shape marker and coil position markers are generated by estimating the positions of the coils while compensating for information on the coil. Hence, the body cavity probe apparatus 1 of the present embodiment is capable of preventing circumstances, for instance, in which a portion of the insertion shape marker is not displayed as a result of the existence of coils for which the information relating to position and/or orientation cannot be acquired, and consequently the load on the operator is lightened.

According to the above-described configuration and operations, the body cavity probe apparatus 1 of the present embodiment is able to detect the insertion shape of the rigid portion 21 and the flexible portion 22 of the ultrasound endoscope 2 and the orientation of the ultrasound tomographic image without exposing the test subject 37 to radiation, and generate a 3-dimensional guide image which includes both the insertion shape and the image orientation.

According to the above-described configuration and operations, the body cavity probe apparatus 1 of the present embodiment is able to provide guide information about the relative positions of the ultrasound tomographic image and the region of interest, which may be the pancreas or the like, and to provide guide information about the shape and orientation of the radial scanning plane of the ultrasound endoscope 2, the flexible portion 22 and the rigid portion 21 with respect to the walls of the body cavity, which may be the alimentary tract or the like. Hence, the operator is able to visually confirm the relative positions and easily perform diagnosis and treatment on the region of interest.

According to the above-described configuration and operations, the body cavity probe apparatus 1 of the present embodiment provides 3-dimensional guide images in which the positions of the ultrasound tomographic image marker Mu, the distal end direction marker Md, the 6 o'clock direction marker Mt and the insertion shape marker Ms anatomically match the actual positions of the ultrasound tomographic image, the flexible portion 22 and the rigid portion 21 with high accuracy, even when the body position of the test subject 37 changes during the test with the ultrasound endoscope 2 (provided there is no change in the relative positions of the body surface characteristic points and the organs).

According to the above-described configuration and operations, the body cavity probe apparatus 1 of the present embodiment is capable of maintaining the high accuracy of matching of the anatomical positions even when the amounts of displacement due to gravity in the organs of the test subject 37 differ in the test using the X-ray 3-dimensional helical computer tomography system 15 or the 3-dimensional magnetic resonance imaging system 16 and the test using the ultrasound endoscope 2 due to differences in the body position assumed by the test subject 37. The high accuracy of matching is achieved by applying the second mapping to points in the body of the test subject 37, such as the center 0″ of the ultrasound tomographic image. Hence, the body cavity probe apparatus 1 of the present embodiment provides a 3-dimensional guide image which allows the ultrasound tomographic image to be guided more accurately.

According to the above-described configuration and operations, in the body cavity probe apparatus 1 of the present embodiment the 3-dimensional guide image can, for instance, be displayed with an orientation that matches the left lateral position which is the body position generally used in tests with the ultrasound endoscope 2. Hence, the test subject 37 and the 3-dimensional guide image can be easily compared. As a result, the body cavity probe apparatus 1 of the present embodiment improves operability and suitably assists the operator to make diagnoses, perform treatments and the like.

Further, according to the above-described configuration and operations, the body cavity probe apparatus 1 of the present embodiment is capable of generating 3-dimensional guide images corresponding to differing viewing directions. As a result, the body cavity probe apparatus 1 of the present embodiment can provide guiding information from multiple directions about the relative positions of the ultrasound tomographic image and the region of interest such as the pancreas or the like, and provide guiding information from multiple directions about the orientation and shape of the ultrasound tomographic image and the flexible portion 22 and rigid portion 21 of the ultrasound endoscope 2 with respect to the walls of the body cavities such as the alimentary tract.

Modifications

The body cavity probe apparatus 1 of the present embodiment is not limited to a configuration that includes the ultrasound endoscope 2 having the treatment instrument channel 46 and the body cavity contacting probe 8 which is passed through the treatment instrument channel 46.

When the body cavity probe apparatus 1 of the present embodiment has a configuration in which the object lens 25 is focused through the optical observation window 24 on the body cavity characteristic point and the rigid portion 21 itself can accurately contact the body cavity characteristic point without use of the body cavity contacting probe 8, the image position and orientation detecting coil 31 fixed to the rigid portion 21 may be used in place of the body cavity detecting coil 42 of the body cavity contacting probe 8. In this case, the image position and orientation detecting coil 31 operates both as the body cavity detecting element and as the image position and orientation detecting element.

In the present embodiment, there are no limits on the method used to perform the ultrasound scanning, and use of the electronic radial scanning-type ultrasound endoscope 2 is not required. For instance, it is possible to use any of a mechanical scanning ultrasound endoscope, an electronic convex scanning ultrasound endoscope equipped with a group of ultrasound transducers which fan out along the insertion axis, an ultrasound probe without an optical observation window 24, and a capsular ultrasound element.

The body cavity probe apparatus 1 of the present embodiment has a configuration in which the ultrasound transducers on the rigid portion 21 of the ultrasound endoscope 2 are finely divided into rectangular sections which form a ring array around the insertion axis. The ultrasound transducer array 29 which forms the ring array may be provided so as to cover 360° of the circumference or provided so as to cover a 270° or 180° portion of the circumference.

The body cavity probe apparatus 1 of the present embodiment has a configuration and operations in which the transmission antenna 6 transmits and the various coils receive in a position detecting portion to detect positions and orientation of the coils in the magnetic field. However, the transmitting and receiving roles may be reversed. In the case of such a role reversal, the positions and orientations are detectable using the magnetic field and so the position (and orientation) detecting portion can be formed using a simple configuration, at low cost, and with a smaller size. Moreover, the position (and orientation) detecting portion is not limited to a configuration which utilizes magnetic fields, and may detect position and orientation by measuring acceleration or by some other means.

In the present embodiment, the origin 0 was set at a specific position on the transmission antenna 6, but the origin 0 can be set in another location which has the same relative position as the transmission antenna 6.

In the present embodiment, the image position and orientation detecting coil 31 is fixed within the rigid portion 21. However, the image position and orientation detecting coil 31 may be provided in another location which maintains a fixed (defined) position relative to the rigid portion 21.

In the present embodiment, the organs in the 3-dimensional guide image data are displayed in different colors. However, rather than being shown in different colors (changing the displayed colors), the different organs may be shown with different brightness, contrast or shading. For instance, each organ may be given a different brightness value.

The present embodiment is configured to make use of a plurality of 2-dimensional CT images picked up using the X-ray 3-dimensional helical computer tomography system 15 or a plurality of 2-dimensional MRI images picked up using the 3-dimensional magnetic resonance imaging system 16. However, the present invention is not limited to this arrangement, and 3-dimensional image data acquired in advance in a different modality, such as by using PET (Positron Emission Tomography) system or the like, may be used. Further, 3-dimensional image data may be used which has been acquired in advance by exposing the subject to ultrasound from outside the body using an external-type body cavity probe apparatus.

The present embodiment has a configuration which makes use of image data picked up by the X-ray 3-dimensional helical computer tomography system 15 from the test subject 37 as the reference image data. However, the invention is not limited to this configuration, and prepared image data of a different person of the same sex and similar build may be used.

Further, the present embodiment has a configuration in which the body surface detecting coils 7 includes four coils each wound around a single axis direction and removably fixed to a different one of the body surface characteristic points on the body surface of the test subject using tape, a belt, bands or the like, and the position and orientation data of the body surface characteristic points are acquired simultaneously. However, the invention is not limited to this configuration, and a configuration may be used in which a single coil, such as the body cavity detecting coil 42 is used in place of the body surface detecting coils 7. In this case, prior to the test using the ultrasound endoscope 2, the test subject 37 is made to assume the left lateral position and the tip of the body cavity contacting probe 8 is sequentially touched against each of the plurality of body surface characteristic points in order to sequentially obtain the position and orientation data for each of the body surface characteristic points.

Further, although in the present embodiment, the position and orientation calculating portion calculates the positions of the body surface detecting coils 7 as the position and orientation data, orientations of the winding axes may be calculated instead of the positions of the coils. Alternatively, both the positions of the coils and orientations of the winding axes may be calculated. By increasing the number of degrees of freedom calculated by the position and orientation calculating apparatus 5 for a single body surface detecting coil 7, it is possible to reduce the required number of body surface detecting coils 7, and reduce the load on the operator and the test subject 37 when fixing the body surface detecting coils 7 are fixed to the test subject 37 and during the ultrasound endoscope test.

In the present embodiment, the xiphoid process, the left anterior superior iliac spine, the right anterior superior iliac spine and the spinous process of vertebral body on the surface of the ventral portion were described as the body surface characteristic points and the duodenal papilla was described as the body cavity characteristic point, but the invention is not limited to this example, and the other characteristic points such as on the surface of the chest portion and within body cavities in the chest portion may be used.

In the present embodiment, an example was described in which 3-dimensional guide image data showing the test subject from the caudal side was generated based on operator input from the mouse 12 or the keyboard 13. However, the present invention is not limited to this example and a configuration may be used in which the 3-dimensional guide image can be rotated in real time on any desired axis to any desired angle in response to the operator input.

Second Embodiment

The following describes a second embodiment of the present invention. Note that the present embodiment is the same as the first embodiment except in the operations of the 3-dimensional guide image generating circuit B. For this reason, descriptions of portions of the configuration and operations which are identical to those of the first embodiment are omitted.

The following describes operations of the present embodiment.

As described above, the present embodiment only differs from the first embodiment in the operations of the 3-dimensional guide image generating circuit B.

As shown in FIG. 15, the 3-dimensional guide image generating circuit B in the first embodiment generates 3-dimensional guide image data showing the test subject from the caudal side, and outputs the result to the mixing circuit 61. The first embodiment has a configuration in which when the radial scanning plane moves according to the operator's hand operations of the flexible portion 22 and the rigid portion 21, the various markers in the 3-dimensional body image data move or change shape. Specifically, the ultrasound tomographic image marker Mu, the distal end direction marker Md and the 6 o'clock direction marker Mt of the image indicator data, and the insertion shape marker Ms and the coil position markers Mc of the insertion shape data move or change shape in the 3-dimensional body image data.

Figure 22:
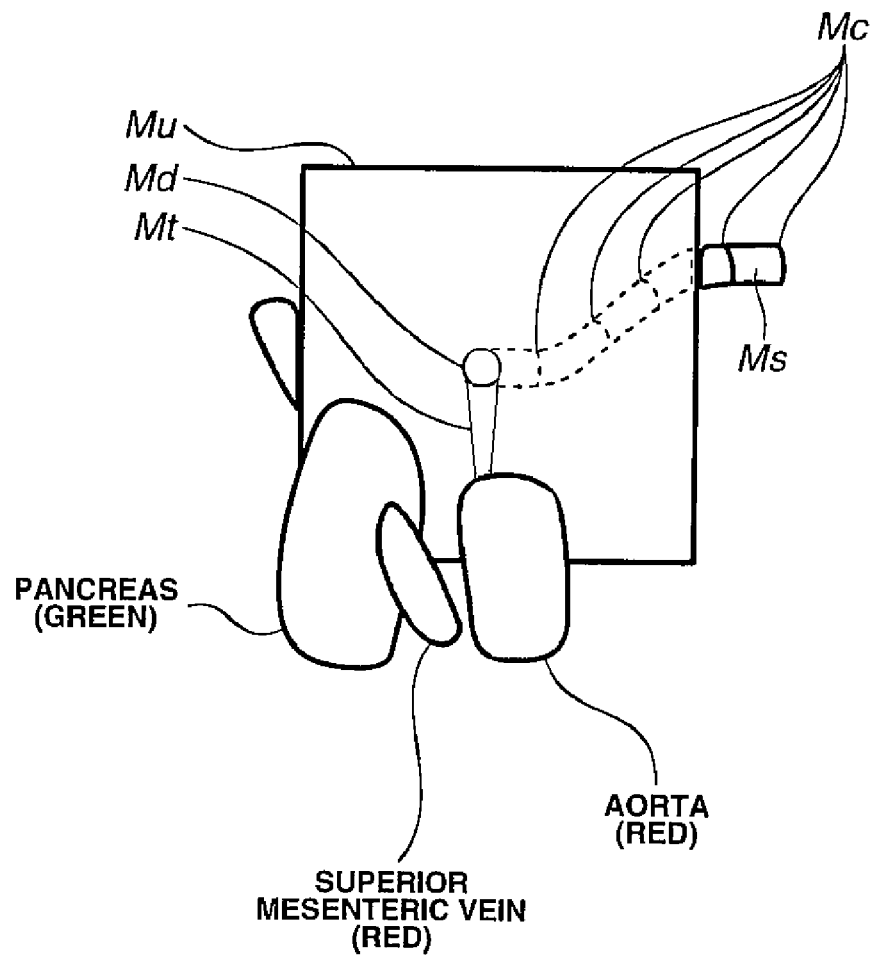
FIG. 22 is a diagram for explanation showing the 3-dimensional guide image data of a second embodiment of the invention.

As shown in FIG. 22, the 3-dimensional guide image generating circuit B in the present embodiment generates guide images in which a normal to the ultrasound tomographic image marker Mu matches an observation direction (i.e. a normal to the screen of the display apparatus 14) to give a full-frontal (squarely-face) view based on position and orientation mapped data, and the 6 o'clock direction marker Mt is set to point downwards on the screen of the display apparatus 14.

With regard to the 3-dimensional guide image data of FIG. 22, it is to be noted that when the radial scanning plane moves according to the operator's hand operations of the flexible portion 22 and the rigid portion 21, the various markers maintain fixed positions on the screen of the display apparatus 14 while the 3-dimensional body image data moves. Here, the various markers are the ultrasound tomographic image marker Mu, the distal end direction marker Md and the 6 o'clock direction marker Mt of the image indicator data, and the insertion shape marker Ms and the coil position markers Mc of the insertion shape data.

In the 3-dimensional guide image shown in FIG. 22, the ultrasound tomographic image marker Mu of the image indicator data is made semi-transparent to allow the 6 o'clock direction marker Mt and the distal end direction marker Md of the image indicator data and the insertion shape marker Ms and the coil position markers Mc of the insertion shape data to be seen through the ultrasound tomographic image marker Mu. Further, the ultrasound tomographic image marker Mu is made non-transparent to the other organs so that portions of the organs which are located behind the ultrasound tomographic image marker Mu cannot be seen.

The other operations of the second embodiment are the same as those of the first embodiment.

The present embodiment has the following advantage.

According to the present embodiment, the 3-dimensional guide image generating circuit B generates a 3-dimensional guide image in which the normal to the ultrasound tomographic image marker Mu matches the observation direction (i.e. the normal to the screen of the display apparatus 14) to give a full-frontal (squarely-face) view based on position and orientation mapped data, and the 6 o'clock direction marker Mt is set to point in the downwards direction on the screen of the display apparatus 14. Hence, the orientation of the 3-dimensional guide image matches the orientation of the ultrasound tomographic image which is displayed in real time next to the 3-dimensional guide image on the screen of the display apparatus 14. Thus, the operator is able to compare the 3-dimensional guide image and the ultrasound tomographic image easily, and it is easy to make an anatomical interpretation of the ultrasound tomographic image.

The other advantages of the second embodiment are the same as those of the first embodiment.

Modifications

The modifications described for the first embodiment can also be applied to the present embodiment.

Third Embodiment

The following describes a third embodiment of the invention.

Note that the present embodiment is the same as the second embodiment except in the operations of the 3-dimensional guide image generating circuit B. For this reason, descriptions of portions of the configuration and operations which are identical to those of the second embodiment are omitted.

The following describes operations of the present embodiment.

As described above, the present embodiment only differs from the second embodiment in the operations of the 3-dimensional guide image generating circuit B.

In the second embodiment, the 3-dimensional guide image generating circuit B generates the 3-dimensional guide image data shown in FIG. 22 in which the ultrasound tomographic image marker Mu of the image indicator data is made semi-transparent to allow the 6 o'clock direction marker Mt and the distal end direction marker Md of the image indicator data and the insertion shape marker Ms and the coil position markers Mc of the insertion shape data to be seen through the ultrasound tomographic image marker Mu and the ultrasound tomographic image marker Mu is made non-transparent to the other organs so that portions of the organs which are located behind the ultrasound tomographic image marker Mu cannot be seen. The 3-dimensional guide image generating circuit then outputs the generated data to the mixing circuit 61.

Figure 23:
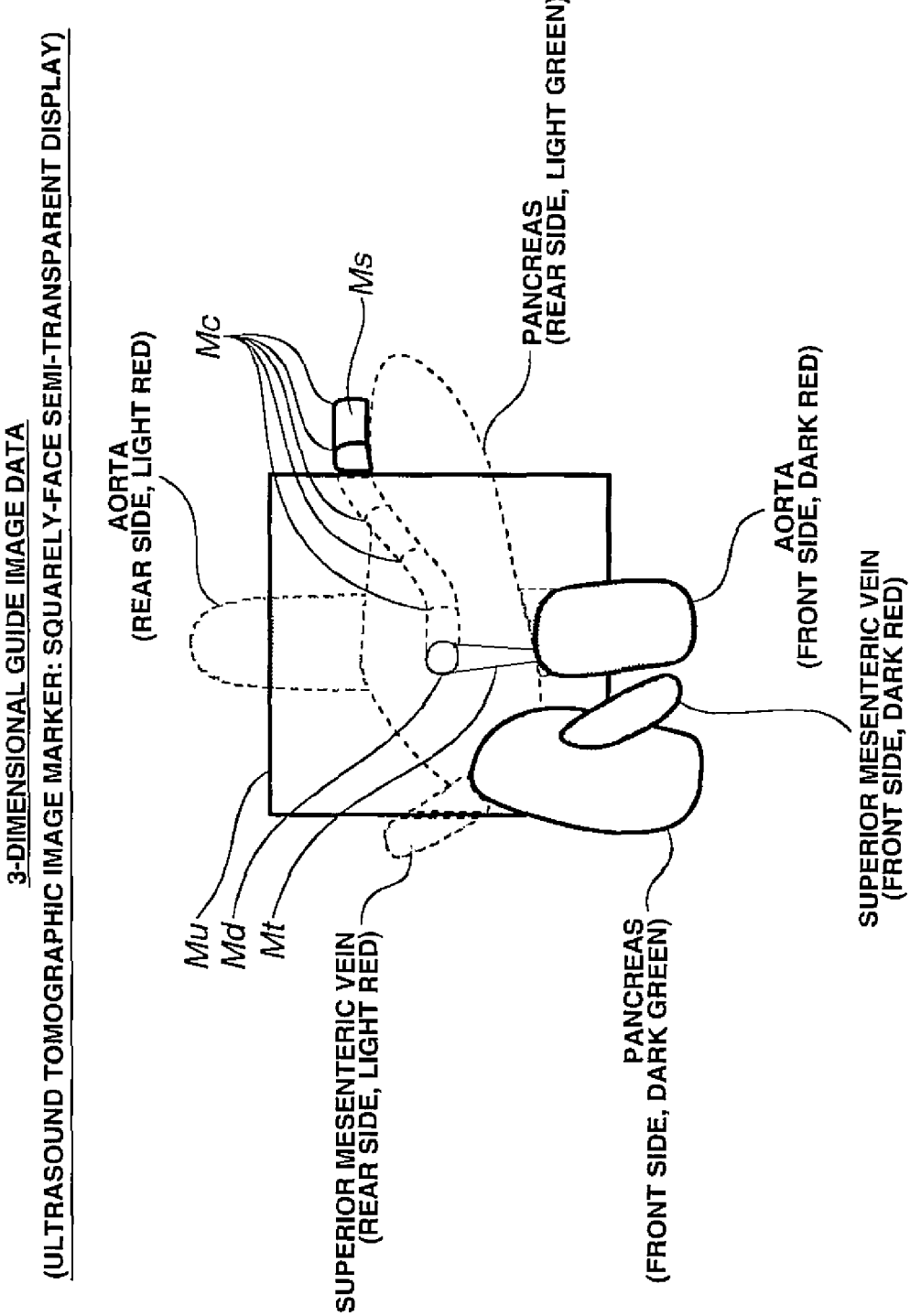
FIG. 23 is a diagram for explanation showing the 3-dimensional guide image data of a third embodiment of the invention.

In the present embodiment, the 3-dimensional guide image generating circuit B makes the ultrasound tomographic image marker Mu of image indicator data semi-transparent as shown in FIG. 23. Thus, the 3-dimensional guide image generating circuit B generates 3-dimensional guide image data in which it is possible to see the portions of the other organs behind the ultrasound tomographic image marker Mu as well as the 6 o'clock direction marker Mt and the distal end direction marker Md of the image indicator data and the insertion shape marker Ms and the coil position markers Mc of the insertion shape data, and outputs the result to the mixing circuit 61. In the 3-dimensional guide image data, the portion in front of the ultrasound tomographic image marker Mu is assigned different brightness from that assigned to the portion behind the same marker.

In the case of the pancreas, for instance, the portion in front (front side) of the ultrasound tomographic image marker Mu is generated in dark green and the portion behind the same marker is generated in light green. In the case of the blood vessels, for instance, the portion in front of (on a near side of) the ultrasound tomographic image marker Mu is generated in dark red and the portion behind the same marker is generated in light red.

Note also that the markers and organs in FIG. 23 which are located behind and overlapped by the ultrasound tomographic image marker Mu are shown using broken lines.

The other operations of the third embodiment are the same as those of the second embodiment.

The present embodiment has the following advantage.

According to the present embodiment, the 3-dimensional guide image generating circuit B generates the 3-dimensional guide image data in which the ultrasound tomographic image marker Mu of the image indicator data is semi-transparent so that it is possible to see the portions of the other organs behind the ultrasound tomographic image marker Mu as well as the 6 o'clock direction marker Mt and the distal end direction marker Md of the image indicator data and the insertion shape marker Ms and the coil position markers Mc of the insertion shape data. Further, the portions in front of and behind the ultrasound tomographic image marker Mu are assigned different brightness.

Hence, according to the present embodiment, it is easier to understand how to move the flexible portion 22 and the rigid portion 21 so that the region of interest in the diseased portion is displayed in the ultrasound tomographic image. Consequently, it becomes easier to operate the flexible portion 22 and the rigid portion 21 of the ultrasound endoscope 2.

In particular, organs which are soft and move easily within the test subject 37, such as the gall bladder, may show up at the ultrasound tomographic image marker Mu in the 3-dimensional body image but not in the ultrasound tomographic image. The 3-dimensional guide image of the present embodiment, however, acts as a marker to allow the gall bladder to be picked out in the ultrasound tomographic image. As a result it is easier to direct the rigid portion 21 and the flexible portion 22 towards the gall bladder.

The other advantages of the third embodiment are the same as those of the second embodiment.

Modification

According to the configuration and operations of the present embodiment, the ultrasound tomographic image marker Mu of the image indicator data is made semi-transparent so that it is possible to see the other organs behind the ultrasound tomographic image marker Mu as well as the 6 o'clock direction marker Mt and the distal end direction marker Md of the image indicator data, and the insertion shape marker Ms and the coil position markers Mc of the insertion shape data. However, the embodiment is not limited to this arrangement and may be modified so that the degree of transparency of the ultrasound tomographic image marker Mu can be freely changed by selective input from the mouse 12 or keyboard 13.

The modifications of the second embodiment can also be applied to the present embodiment.

Fourth Embodiment

The following describes a fourth embodiment of the invention.

Note that the present embodiment is the same as the third embodiment except in the operations of the 3-dimensional guide image generating circuit B. For this reason, descriptions of portions of the configuration and operations which are identical to those of the third embodiment are omitted.

The following describes operations of the present embodiment.

As described above, the present embodiment only differs from the third embodiment in the operations of the 3-dimensional guide image generating circuit B.

As shown FIG. 23, in the third embodiment, the 3-dimensional guide image generating circuit B generates the 3-dimensional guide image data in which the ultrasound tomographic image marker Mu of the image indicator data is semi-transparent so that the portions of the other organs behind the ultrasound tomographic image marker Mu can be seen as well as the 6 o'clock direction marker Mt and the distal end direction marker Md of the image indicator data, and the insertion shape marker Ms and the coil position markers Mc of the insertion shape data. Further, the portions in front of and behind the ultrasound tomographic image marker Mu are assigned different brightness. The 3-dimensional guide image generating circuit B outputs the generated 3-dimensional guide image data to the mixing circuit 61.

In the third embodiment, in the case of the pancreas, for instance, the portion in front of (on the near side of) the ultrasound tomographic image marker Mu is generated in dark green and the portion behind the same marker is generated in light green. In the third embodiment, in the case of the blood vessels, for instance, the portions in front of (on the near side of) the ultrasound tomographic image marker Mu are generated in dark red and the portions behind the same marker are generated in light red.

Figure 24:
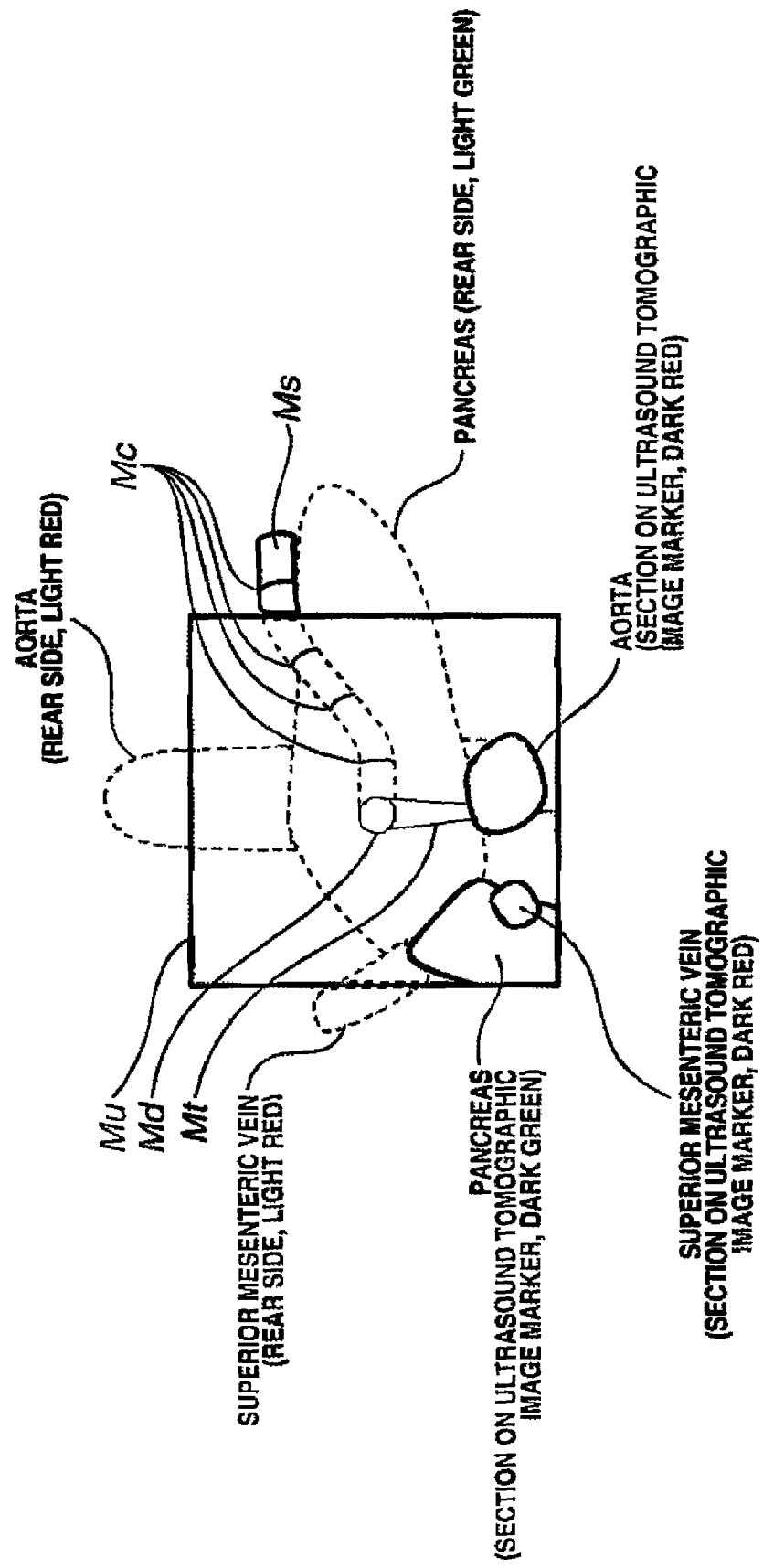
FIG. 24 is a diagram for explanation showing the 3-dimensional guide image data of a fourth embodiment of the invention.

As shown in the FIG. 24, in the present embodiment, the 3-dimensional guide image generating circuit B generates 3-dimensional guide image data which is divided into two regions by the ultrasound tomographic image marker Mu. The first region includes the distal end side of the flexible portion 22 (i.e. near side of the screen of the display apparatus 14) and the second region includes the ultrasound tomographic image marker Mu and a portion behind the ultrasound tomographic image marker Mu. In the first region nothing is displayed. In the second region, a section on the ultrasound tomographic image marker Mu and the portion behind the ultrasound tomographic image marker Mu are given different brightness. The generated 3-dimensional guide image data is then outputted to the mixing circuit 61.

In the case of the pancreas, for instance, the section on the ultrasound tomographic image marker Mu is generated in dark green and the portion behind the same marker is generated in light green. In the case of the blood vessels, the section on the ultrasound tomographic image marker Mu is generated in dark red and the portion behind the same marker is generated in light red.

The other operations of the fourth embodiment are the same as those of the third embodiment.

The present embodiment has the following advantage.

In the present embodiment, the 3-dimensional guide image generating circuit B generates 3-dimensional guide image data which is divided into two regions by the ultrasound tomographic image marker Mu. In the first region on the distal end side of the flexible portion 22 (i.e. the region towards the screen of the display apparatus 14) nothing is displayed. In the second region, the section on the ultrasound tomographic image marker Mu and the portion behind the ultrasound tomographic image marker Mu are given different brightness.

Thus, in the present embodiment, the organs in the first region of the 3-dimensional image data do not obstruct the view of the operator. As a result, it is easier for the operator to compare the 3-dimensional guide image and the ultrasound tomographic image displayed adjacent to the 3-dimensional guide image on the screen of the display apparatus 14 and anatomically interpret the ultrasound tomographic image.

The other advantages of the fourth embodiment are the same as those of the third embodiment.

Modifications

The modifications described for the third embodiment can also be applied to the present embodiment.

Fifth Embodiment

The following describes a fifth embodiment of the invention.

Note that the present embodiment is the same as the first embodiment except in the operations of the 3-dimensional guide image generating circuit B. For this reason, descriptions of portions of the configuration and operations which are identical to those of the first embodiment are omitted.

The following describes operations of the present embodiment.

As described above, the present embodiment only differs from the first embodiment in the operations of the 3-dimensional guide image generating circuit B.

As shown in FIG. 15, in the first embodiment, the 3-dimensional guide image generating circuit B generates the 3-dimensional guide image data in which the ultrasound tomographic image marker Mu of the image indicator data is semi-transparent so that it is possible to see the 6 o'clock direction marker Mt and the distal end direction marker Md of the image indicator data and the insertion shape marker Ms and the coil position markers Mc of the insertion shape data. However, the ultrasound tomographic image marker is made non-transparent to the other organs so that portions of organs behind the ultrasound tomographic image marker Mu cannot be seen. The generated 3-dimensional guide image data is outputted to the mixing circuit 61.

Figure 25:
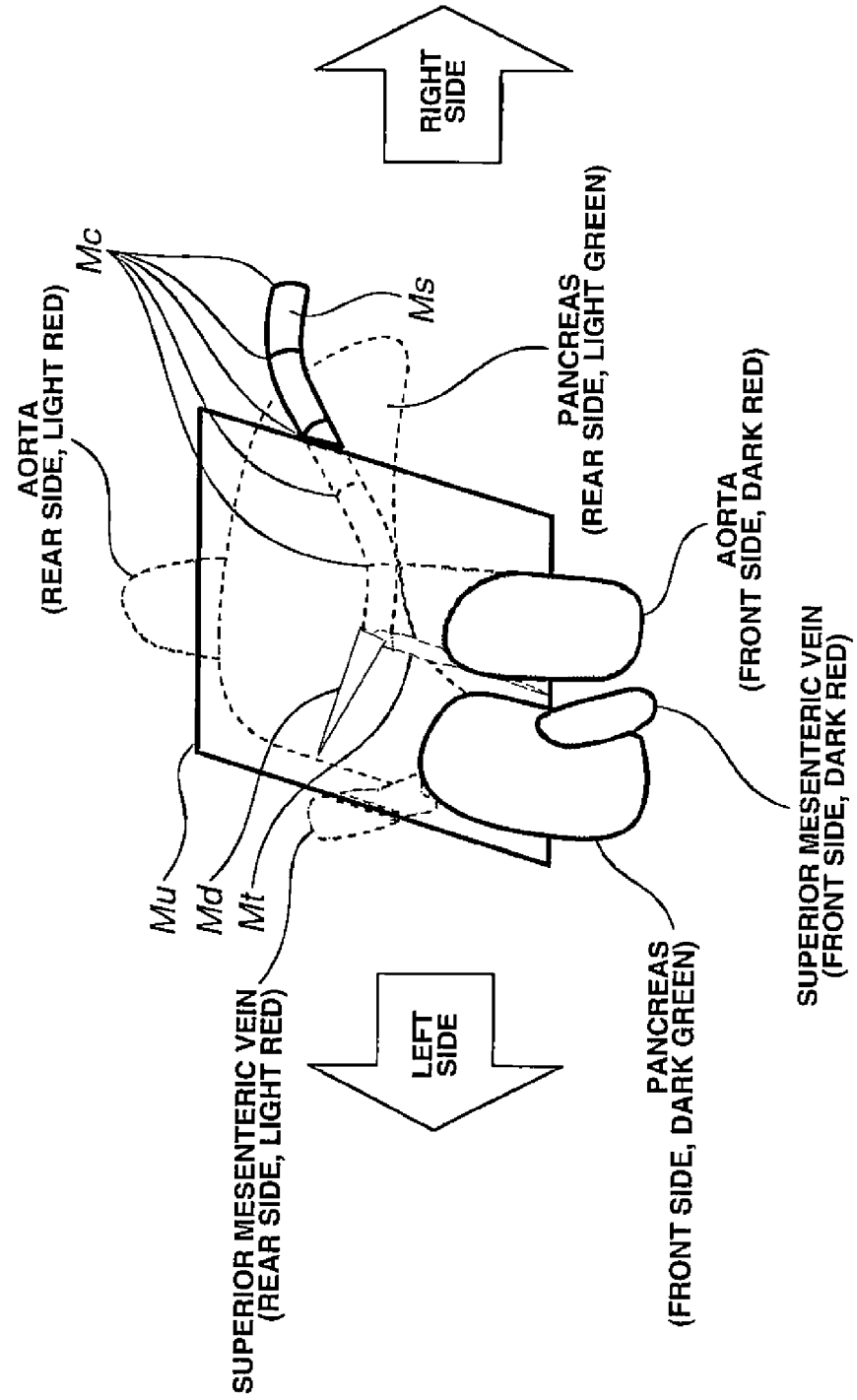
FIG. 25 is a diagram for explanation showing 3-dimensional guide image data of a fifth embodiment of the invention.

As shown in FIG. 25, in the present embodiment, the 3-dimensional guide image generating circuit B generates the 3-dimensional guide image data in which the ultrasound tomographic image marker Mu of the image indicator data is semi-transparent so that the portions of the other organs behind the ultrasound tomographic image marker Mu can be seen as well as the 6 o'clock direction marker Mt and the distal end direction marker Md of the image indicator data, and the insertion shape marker Ms and the coil position markers Mc of the insertion shape data. In the 3-dimensional guide image, the portions in front of and behind the ultrasound tomographic image marker Mu are assigned different brightness. The 3-dimensional guide image generating circuit B then outputs the generated 3-dimensional guide data to the mixing circuit 61.

In the case of the pancreas, for instance, the portion on the distal end direction marker Md side of tomographic image marker Mu is generated in dark green and the portion on the opposing side of the same marker is generated in light green. In the case of the blood vessels, the portion on the distal end direction marker Md side of the ultrasound tomographic image marker Mu is generated in dark red and the portion on the opposing side of the same marker is generated in light red.

The other operations of the fifth embodiment are the same as those of the first embodiment.

The present embodiment has the following advantage.

According to the present embodiment, the 3-dimensional guide image generating circuit B generates the 3-dimensional guide image data in which the ultrasound tomographic image marker Mu of the image indicator data is semi-transparent so that the portions of the other organs behind the ultrasound tomographic image marker Mu can be seen as well as the 6 o'clock direction marker Mt and the distal end direction marker Md of the image indicator data, and the insertion shape marker Ms and the coil position markers Mc of the insertion shape data. In the 3-dimensional guide image, the portions in front of and behind the ultrasound tomographic image marker Mu are assigned different brightness.

Hence, according to the present embodiment, it is easier to understand bow to move the flexible portion 22 and the rigid portion 21 so that the region of interest, such as the diseased portion, is displayed on the ultrasound tomographic image. As a result, it is easier to operate the ultrasound endoscope 2.

In particular, organs which are soft and move easily within the test subject 37, such as the gall bladder, may show up at the ultrasound tomographic image marker Mu in the 3-dimensional body image but not in the ultrasound tomographic image. The 3-dimensional guide image of the present embodiment, however, acts as a marker to allow the gall bladder to be picked out in the ultrasound tomographic image. As a result, it is easier to direct The rigid portion 21 and the flexible portion 22 towards the gall bladder.

The other advantages of the fifth embodiment are the same as those of the first embodiment.

Modification

According to the present embodiment, the ultrasound tomographic image marker Mu of the image indicator data is made semi-transparent so that it is possible to see portions of the other organs behind the ultrasound tomographic image marker Mu as well as the 6 o'clock direction marker Mt and the distal end direction marker Md of the image indicator data, and the insertion shape marker Ms and the coil position markers Mc of the insertion shape data. However, the embodiment is not limited to this arrangement and may be modified so that the degree of transparency of the ultrasound tomographic image marker Mu can be freely changed by selective input from the mouse 12 or the keyboard 13.

The modifications of the first embodiment can further be applied to those of the present embodiment.

Sixth Embodiment

The following describes a sixth embodiment of the invention. The description of the present embodiment mainly deals with points which differ from the first embodiment.

The rigid portion 21 of the first embodiment includes the image position and orientation detecting coil 31 which is fixed in proximity to the center of the ring formed by the ultrasound transducer array 29.

The rigid portion 21 of the present embodiment includes an image and orientation detecting coil 31 which is fixed in proximity to the CCD camera 26.

The orientation of the fixed image position and orientation detecting coil 31 is the same as that of the first embodiment. The optical axis of the CCD camera 26 is set at a known angle relative to the vector V in the plane of FIG. 1 that includes the vectors V and $V_{12}$.

Figure 26:
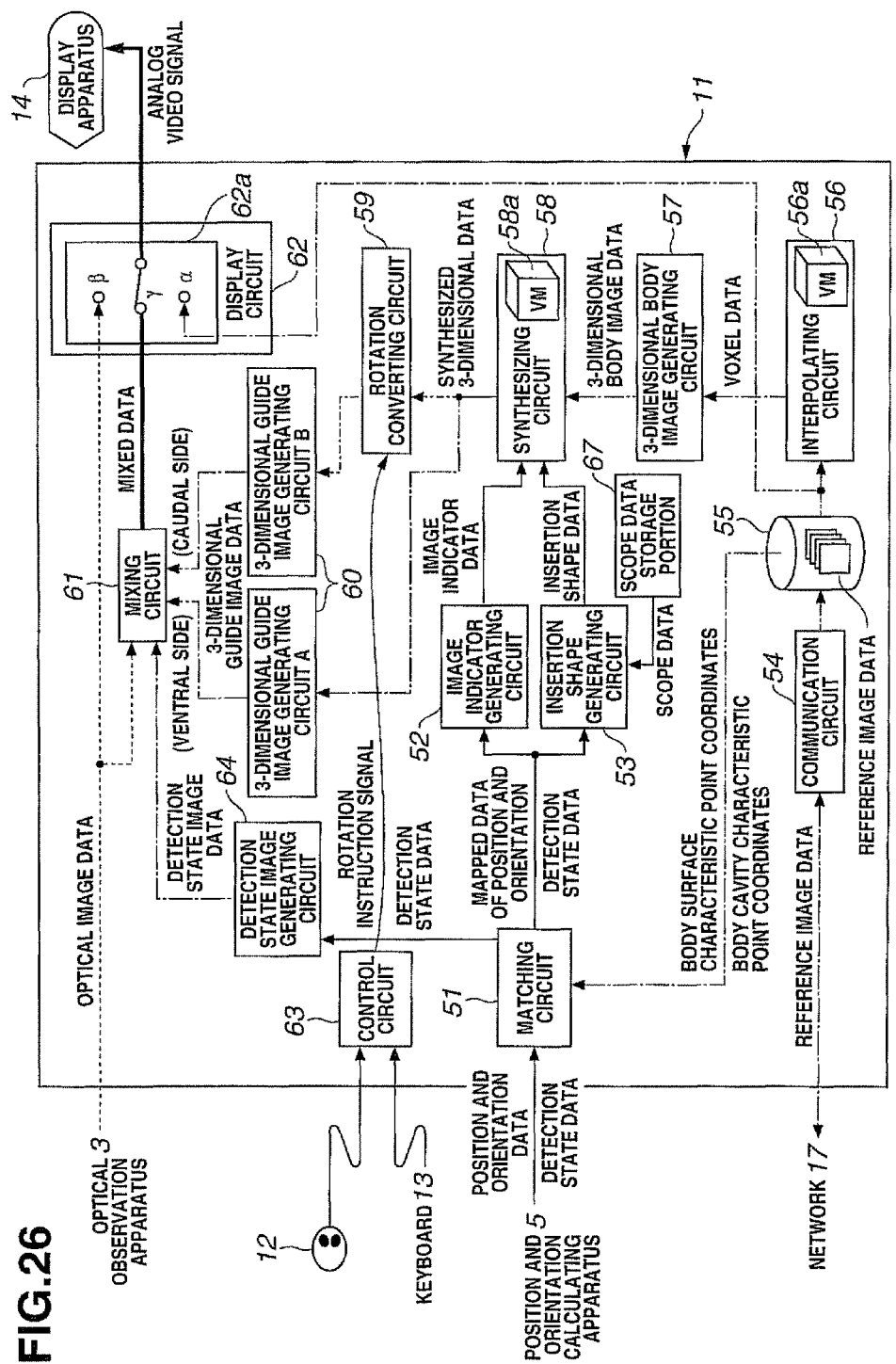
FIG. 26 is a block diagram showing a configuration of an image processing apparatus of a sixth embodiment of the invention.

FIG. 26 shows the image processing apparatus 11 of the present embodiment. The mixing circuit 61 in the image processing apparatus 11 of the first embodiment was connected to the ultrasound observation apparatus 4. In the present embodiment, on the other hand, the mixing circuit 61 is connected to the optical observation apparatus 3 instead of the ultrasound observation apparatus 4.

Otherwise, the sixth embodiment is configured in the same way as the first embodiment.

The following describes operations of the present embodiment.

According to the operations of the image processing apparatus 11 of the first embodiment, the operator selects the X-ray 3-dimensional helical computer tomography system 15 as the acquisition source, and the communication circuit 54 acquires a plurality of 2-dimensional CT images as the reference image data and stores the reference image data of the type shown in FIG. 5 in the reference image storage portion 55. In the reference images, the blood vessels such as the aorta and the superior mesenteric vein have high brightness, the organs having a large number of peripheral blood vessels, such as the pancreas, have a medium brightness, and the duodenum and the like have a low brightness due to the actions of the X-ray contrast medium.

For the present embodiment, an example is described in which a chest, and trachea, bronchus, and bronchial branches in particular, have been imaged without a contrast medium by the X-ray 3-dimensional helical CT system 15. The example deals with a case in which the ultrasound endoscope 2 is inserted into a bronchial branch "a" at a point where the bronchial branches into the bronchial branch "a" and a bronchial branch "b".

The optical observation apparatus 3 generates optical image data in such a way that the 12 o'clock direction (upwards direction) of the optical image is maintained in direct opposition to the projection direction of the vector $V_{12}$ onto the plane that includes V and $V_{12}$ in FIG. 1.

The 3-dimensional body image generating circuit 57 extracts voxels with high brightness values (which mainly correspond to walls of the trachea, the bronchia, and the bronchial branches) from the interpolating circuit 56 and assigns colors to the extracted voxels. The 3-dimensional body image generating circuit 57 also embeds the extracted voxels as 3-dimensional body image data in the voxel space of the synthesizing memory 58a of the synthesizing circuit 58.

At this point, the 3-dimensional body image generating circuit 57 embeds the extracted voxels so that the addresses in the voxel space of the interpolating memory 56a are the same as the addresses in the voxel space in the synthesizing memory. Specifically, in the generated 3-dimensional body image data, the trachea walls, the bronchia walls and the bronchial branch walls with a high brightness are extracted and each wall is assigned a light-pink color. Moreover, the cranial side of the test subject 37 is assigned to the right-hand side and the caudal side of the test subject assigned to the left-hand side so that the 3-dimensional image data is a view from the ventral side.

The image indicator generating circuit 52 generates image indicator data based on position and orientation mapped data and the detection state data, and outputs the generated image indicator data to the synthesizing circuit 58. Here, the position and orientation mapped data includes the directional components (x0, y0, z0) of the position vector 00" of the position 0" of the image position and orientation detection coil 31 in the orthogonal coordinate system 0-xyz and the angular components ($\psi$, $\theta$, $\phi$) of the Euler angular indicating the orientation of the image position and orientation detection coil 31 in the orthogonal coordinate system 0-xyz and therefore has six degrees of freedom.

The image indicator data is image data in the orthogonal coordinate system 0'-x'y'z' synthesized from an optical image field direction marker which indicates an optical axis direction and an optical image up-direction marker which indicates the 12 o'clock direction in the optical image.

The optical image field direction marker and the optical image up-direction marker are colored based on the detection state data of the image position and orientation detecting coil 31. Specifically, when the detection state data of the image position and orientation detecting coil 31 indicates "normal" detection, the optical image field direction marker is colored orange and the optical image up-direction marker is colored light green. Further, when the detection state data of the image position and orientation detecting coil 31 indicates "low accuracy" detection, the optical image field direction marker and the optical image up-direction marker are both colored yellow. Further, when the detection state data of the image position and orientation detecting coil 31 indicates "undetectable", the optical image field direction marker and the optical image up-direction marker are both colored red.

The insertion shape generating circuit 53 generates insertion shape data based on the position and orientation mapped data and the detection state data in the same way as the first embodiment, and outputs the generated insertion shape data to the synthesizing circuit 58. Here the position and orientation mapped data is made up of the directional components (x0, y0, z0) of the position vector 00" of the position 0" of the image position and orientation detecting coil 31 and the directional components (xi, yi, zi) of the position vector of each of the plurality of insertion shape detecting coils 32 in the orthogonal coordinate system 0-xyz. Note that the generation process is illustrated in FIG. 11A. The insertion shape data is image data in the orthogonal coordinate system 0'-x'y'z' synthesized from the interpolated string-like insertion shape marker Ms and the coil position markers Mc which indicate the positions of the coils. Note that the insertion shape marker Ms is generated by sequentially connecting the respective positions of the position and orientation detection coils 31 and the five insertion shape detecting coils 32.

The synthesizing circuit 58 then embeds the image indicator data and the insertion shape data in the voxel space of the synthesizing memory 58a. Thus, the synthesizing circuit 58, embeds the 3-dimensional body image data, the image indicator data, and the insertion shape data in the same voxel space in the synthesizing memory 58a to synthesize 3-dimensional data.

The rotation converting circuit 59 reads the synthesized 3-dimensional data and then performs rotation processing on the synthesized 3-dimensional data in accordance the rotation instruction signal from the control circuit 63.

The 3-dimensional guide image generating circuit A performs rendering processing for hidden surface removal and shading on the synthesized 3-dimensional data to generate 3-dimensional guide image data which can be displayed on the screen. Note that the default orientation of the 3-dimensional guide image data is a view from the ventral side of the body.

Figure 27:
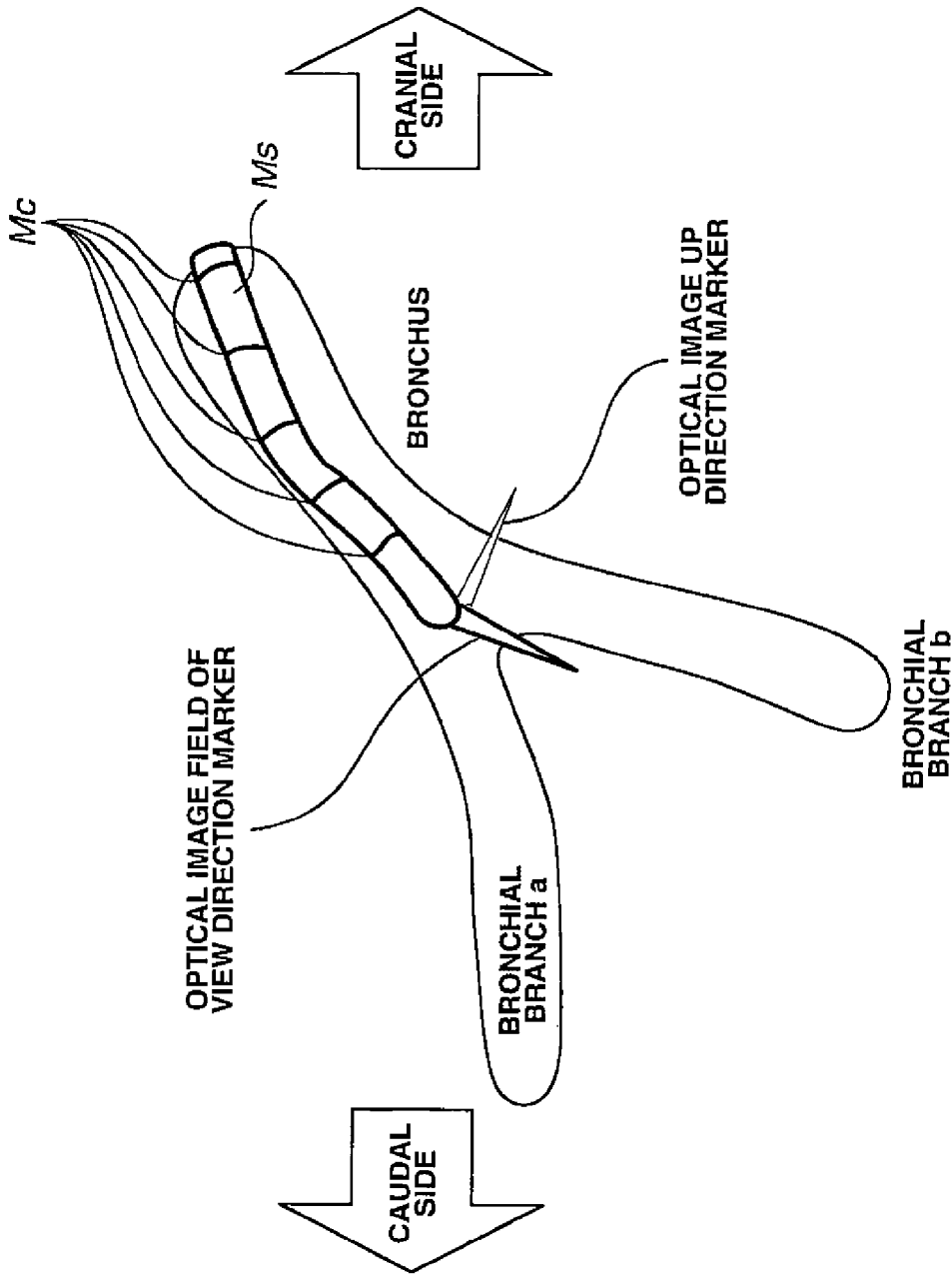
FIG. 27 is a diagram for explanation showing the 3-dimensional guide image data generated by a 3-dimensional guide image generating circuit A.

Hence, the 3-dimensional guide image generating circuit A generates the 3-dimensional guide image data as a view from the ventral side of the test subject 37. The 3-dimensional guide image generating circuit A then outputs the 3-dimensional guide image data showing the test subject 37 from the ventral side to the mixing circuit 61. An example of the 3-dimensional guide image data is shown in FIG. 27. In FIG. 27, the cranial side of the test subject 37 is on the right-hand side and the caudal side of the test subject 37 is on the left-hand side.

In the 3-dimensional guide image data of FIG. 27, the walls of a bronchus, and, the walls of the bronchial branch "a" and bronchial branch "b" are semi-transparent to allow the optical image field direction marker, the optical image up-direction marker of the image indicator data and the insertion shape marker Ms and the coil position markers Mc of the insertion shape data to be seen.

The 3-dimensional guide image generating circuit B performs rendering processing for hidden surface removal and shading on the synthesized 3-dimensional data which has undergone rotation processing to generate 3-dimensional guide image data which can be displayed on the screen.

In the present embodiment, as an example, the instruction based on input from the mouse 12 and the keyboard 13 is for the view from the caudal side of the test subject 37, which is a view in which the 3-dimensional guide image data has been rotated by 90 according to a rotation instruction signal from the control circuit 63.

Figure 28:
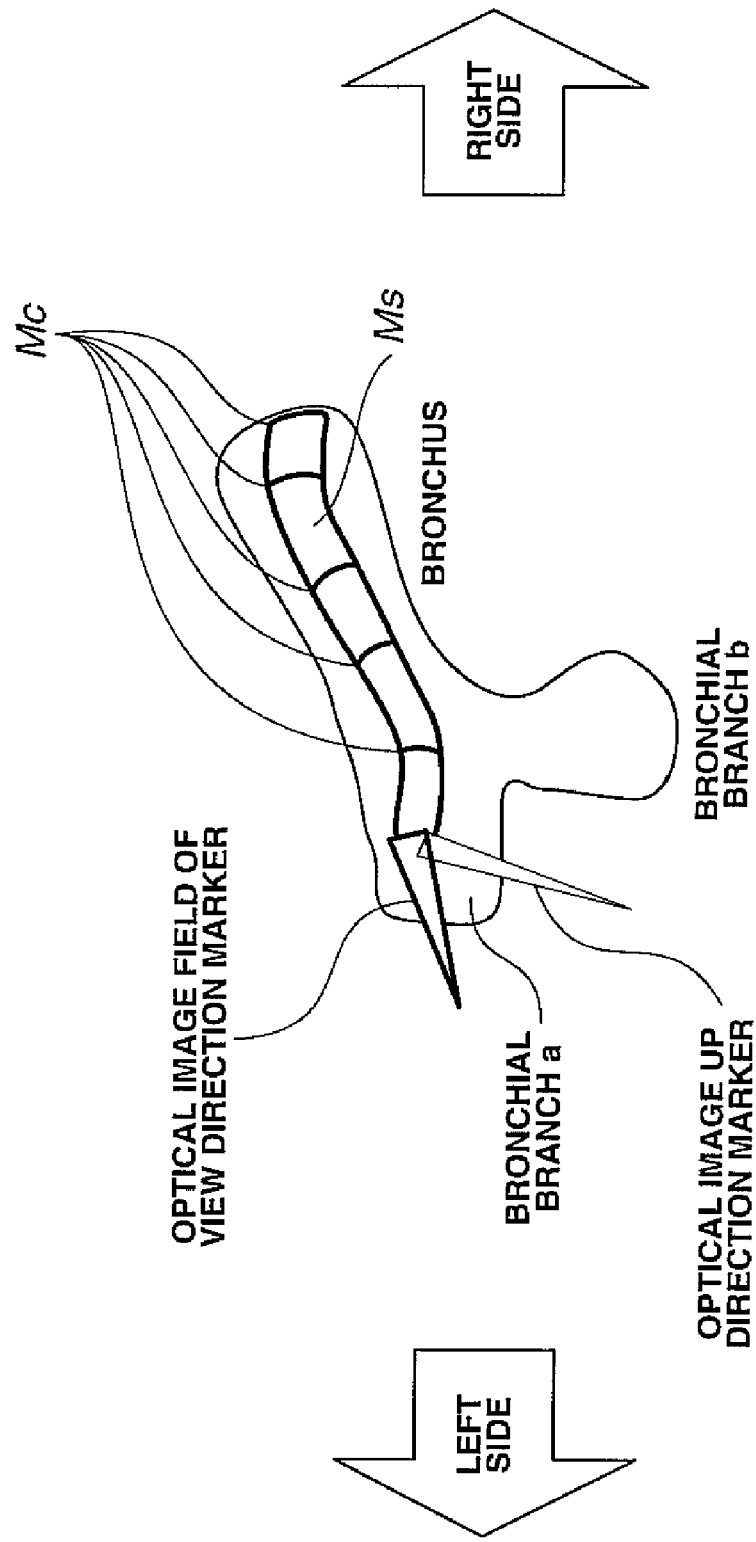
FIG. 28 is a diagram for explanation showing the 3-dimensional guide image data generated by a 3-dimensional guide image generating circuit B.

Hence, the 3-dimensional guide image generating circuit B generates the 3-dimensional guide image data as a view from the caudal side of the test subject 37. The 3-dimensional guide image generating circuit B then outputs the 3-dimensional guide image data which is the view from the caudal side of the test subject 37 to the mixing circuit 61. An example of the 3-dimensional guide image data is shown in FIG. 28. In FIG. 28, the right side of the test subject 37 is shown on the right-hand side and the left side of the test subject 37 is shown on the left-hand side.

In the 3-dimensional guide image data of FIG. 28, the walls of the bronchus, the walls of the bronchial branch "a" and the bronchial branch "b" are made semi-transparent to allow the optical image field direction marker and the optical image up-direction marker of the image indicator data, and the insertion shape marker Ms and the coil position markers Mc of the insertion shape data to be seen.

The detection state image generating circuit 64 generates a detection state image based on the detection state data, of the type shown in FIG. 11 for instance, capable of providing visual notification of the detection states at the position of the image position and orientation detecting coil 31, the positions of the five insertion shape detecting coils 32, and the positions of each of the body surface detecting coils 7. The detection state image generating circuit 64 then outputs the detection state image as detection state image data to the mixing circuit 61. Note that the detection state image data is generated in the manner described in the first embodiment.

The mixing circuit 61 generates mixed data for display by combining the optical image data from the optical observation apparatus 3, the 3-dimensional guide image showing the test subject 37 from the ventral side from the 3-dimensional guide image generating circuit A, the 3-dimensional guide image data showing the subject 37 from the caudal side from the 3-dimensional guide image generating circuit B, and the detection state image data from the detection state image generating circuit 64.

The display circuit 62 converts the mixed data to an analog video signal.

Based on the analog video signal, the display apparatus 14 displays the combination of the optical image, the 3-dimensional guide image showing the test subject 37 from the caudal side, the 3-dimensional guide image showing the test subject 37 from the ventral side, and the detection state image adjacent to each other.

Figure 29:
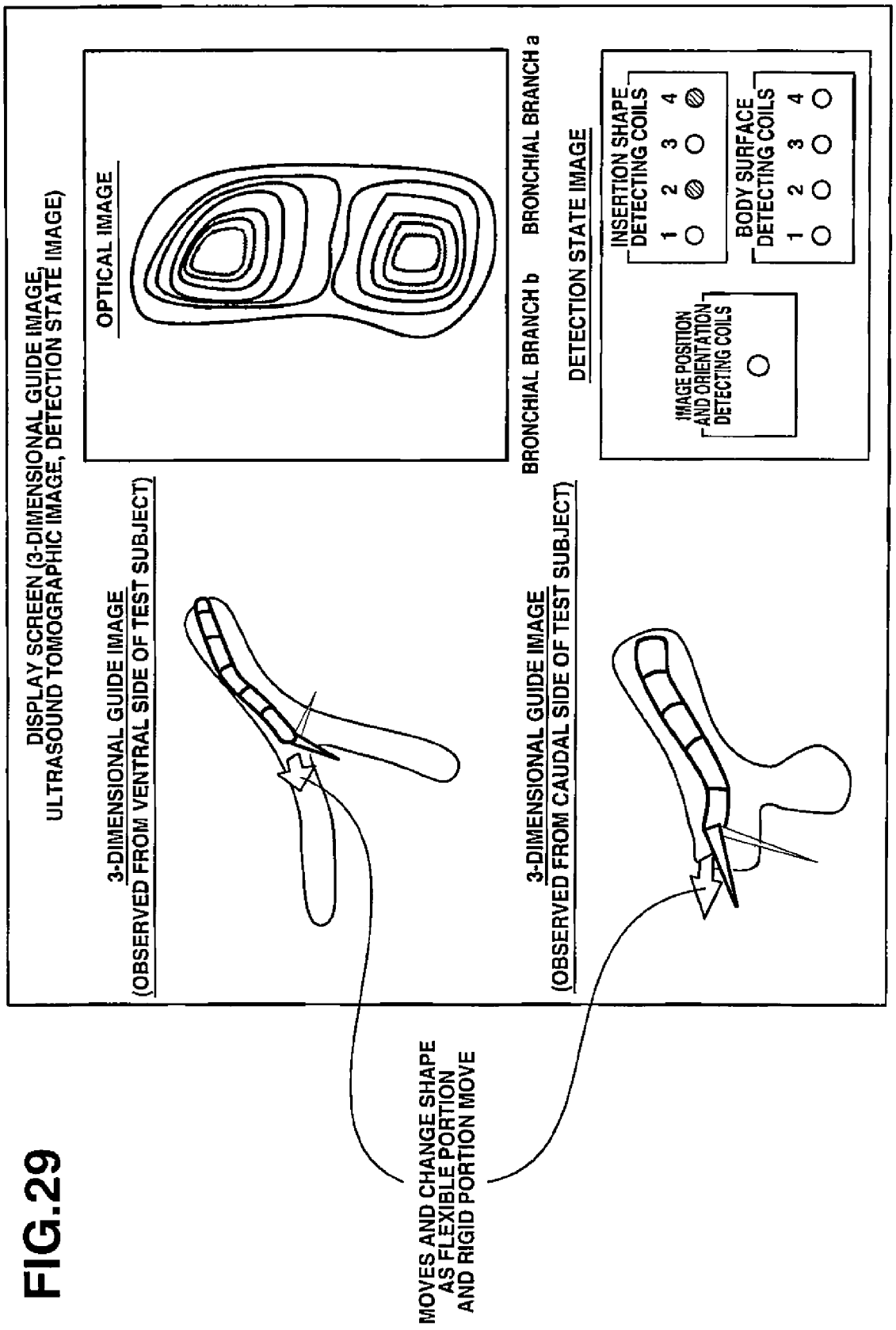
FIG. 29 is a diagram showing the 3-dimensional guide image, an optical image and the detection state image which are displayed on the display apparatus.

As shown in FIG. 29, the display apparatus 14 displays the walls of the bronchus and the walls of the bronchial branches in light pink in the 3-dimensional guide image.

In the present embodiment, the optical image is processed as a real-time image.

Further, in the present embodiment, two new 3-dimensional guide images are generated and updated on the display screen of the display apparatus 14 in real time together with a new optical image, substantially as in the first embodiment. Thus, as shown in FIG. 29, when the flexible portion 22 and the rigid portion 21 are moved by hand along the optical axis, the various markers move and change shape on the 3-dimensional body image data. Here, the various markers are the optical image field direction marker and the optical image up-direction marker of the image indicator data and the insertion shape marker Ms and the coil position marker Mc of the insertion shape data. At the same time, the colors of markers of the detection state image and The colors of markers of the 3-dimensional guide image change with detection states of each coil.

The other operations of the present embodiment are the same as those of the first embodiment.

The present embodiment has the following advantage.

According to the present embodiment, the 3-dimensional guide image is generated in which the walls of the bronchus and the walls of the bronchial branch "a" and the bronchial branch "b" are made semi-transparent to allow the optical image field direction marker and the optical image up-direction marker of the image indicator data and the insertion shape marker Ms and the coil position markers Mc of the insertion shape data to be seen. Further, according to the embodiment, the mixing circuit 61 and the display apparatus 14 operate to display the optical image, the 3-dimensional guide image showing the test subject 37 from the caudal side, the 3-dimensional guide image showing the test subject 37 from the ventral side, and the detection state image adjacent to one another.

Thus, the present embodiment makes it possible to prevent the ultrasound endoscope 2 (or an endoscope of one of the modifications described below) from being mistakenly inserted into the bronchial branch "b" when the endoscope 2 is inserted into the bronchial branch "a".

The other advantages of the present embodiment are the same as those of the first embodiment.

In the present embodiment, the 3-dimensional guide image is generated so that the optical image field direction marker and the optical image up-direction marker of the image indicator data and the insertion shape marker Ms and the coil position markers Mc of the insertion shape data are visible. As a result, the present embodiment allows the operator to smoothly perform diagnosis and treatment not only when inserting the ultrasound endoscope 2 deeply into the bronchia, but in other situations too. Thus, according to the present embodiment, it is possible to realize a body cavity probe apparatus which allows the operator to perform treatment and diagnosis smoothly and easily.

(Modification)

Like the first embodiment, the present embodiment makes use of an electronic radial scanning ultrasound endoscope 2 equipped with an optical observation system (including the optical observation window 24, the object lens 25, the CCD camera 26, and the unshown illumination window) as the body cavity probe. However, the embodiment is not limited to such a probe, and may make use of an endoscope which is only equipped with an optical observation system as the body cavity probe.

Moreover, the modifications of the first embodiment can further be applied to the present embodiment.

Note also that an embodiment configured by combining parts of the above-described embodiments falls within the scope of the invention. Further, the configuration of the image processing apparatus 11 is not limited to that shown in FIG. 4 and may be appropriately altered.

What is claimed is:

1. A medical system comprising:
an image signal acquiring portion for acquiring a signal to generate an image corresponding to a picture of a subject within a test subject;
an image generating portion for generating a real-time image of an inside of the test subject based on the signal acquired by the image signal acquiring portion;
a detecting portion for detecting at least a position and an orientation of an image position and orientation detecting element in a position which is fixed relative to the image signal acquiring portion, and outputting a detection result as a detection value;
a reference image data storage portion for storing reference image data made up of a plurality of anatomical images of the test subject;
a guide image generating portion for generating a guide image to provide guide information about at least one of an anatomical position and orientation within the test subject of the real-time image, based on the detection value detected by the detecting portion and the reference image data; and
a detection state notification information generating portion for generating detection state notification information to notify a detection state of the detection value detected by the detecting portion.

2. The medical system of claim 1, wherein
the image signal acquiring portion is a probe having an elongated shape and one or more insertion shape detecting elements disposed in a longitudinal direction of the probe,
the detecting portion detects a position and orientation of the image position and orientation detecting element, detects a position and orientation of each insertion shape detecting element, and outputs each detection result as the detection value, and
the guide image generating portion generates an insertion shape image for providing guide information about a shape of the probe based on each detection value detected by the detecting portion and the reference image data.

3. The medical system of claim 2, wherein
the detection state notification information generating portion generates information to notify a detection state of the position and orientation of the image position and orientation detecting element and a detection state of the position and orientation of each insertion shape detecting element as the detection state notification information.

4. The medical system of claim 2, wherein
the guide image generating portion calculates, when the position and orientation of the insertion shape detecting element are undetectable by the detecting portion, estimated values for the position and orientation of the insertion shape detecting element that are undetectable by the detecting portion based on the detection values for the position and orientation of the insertion shape detecting element that are detectable by the detecting portion, and generates the insertion shape image using the estimated values.

5. The medical system of claim 1, wherein
the image signal acquiring portion is an ultrasound probe capable of transmitting and receiving ultrasound signals to generate an ultrasound tomographic image of the inside of the test subject and having an elongated shape provided with one or more insertion shape detecting elements disposed in a longitudinal direction of the ultrasound probe.

6. The medical system of claim 1, wherein
the detection state notification information includes information for visually indicating a detection accuracy of each detection value.

7. The medical system of claim 1, wherein
the guide image and the detection state notification information are combined and displayed as an image at a display portion.

8. A medical guide image generating method comprising:
acquiring a signal to generate an image corresponding to a picture of a subject within a test subject;
generating a real-time image of an inside of the test subject based on the acquired signal;

after detecting at least a position and orientation of an image position and orientation detecting element in a fixed position, outputting a detection result as a detection value;

generating a guide image to provide guide information about at least one of an anatomical position and orientation within the test subject of the real-time image based on the detection value and reference image data made up of a plurality of anatomical images of the test subject; and generating detection state notification information to notify a detection state of the detection value.

9. The medical guide image generating method of claim 8, wherein the signal is acquired by a probe having an elongated shape and one or more insertion shape detecting elements disposed in a longitudinal axis direction of the probe, after a position and orientation of the image position and orientation detecting element and a position and orientation of each insertion shape detecting element are detected, each detection result is outputted as the detection value, and an insertion shape image for providing guide information about a shape of the probe is generated based on each detection value and the reference image data.

10. The medical guide image generating method of claim 9, wherein information to notify a detection state of the position and orientation of the image position and orientation detecting element and a detection state of the position and orientation of each insertion shape detecting element is generated as the detection state notification information.

11. The medical guide image generating method of claim 9, wherein when the position and orientation of the insertion shape detecting element are undetectable, the estimated values for the position and orientation of the insertion shape detecting element that are undetectable are calculated based on the detection values for the position and orientation of the insertion shape detecting element that are detectable, and the insertion shape image is then generated using the estimated values.

12. The medical guide image generating method of claim 8, wherein the signal is acquired by an ultrasound probe capable of transmitting and receiving ultrasound signals to generate an ultrasound tomographic image of the inside of the test subject, the ultrasound probe having an elongated shape provided with insertion shape detecting element disposed in a longitudinal direction of the ultrasound probe.

13. The medical guide image generating method of claim 8, wherein the detection state notification information includes information for visually indicating a detection accuracy of each detection value.

14. The medical guide image generating method of claim 8, wherein the guide image and the detection state notification information are combined and displayed as an image at a display portion.

* * * * *